United States Patent
Dobak

(10) Patent No.: US 7,937,145 B2
(45) Date of Patent: May 3, 2011

(54) DYNAMIC NERVE STIMULATION EMPLOYING FREQUENCY MODULATION

(75) Inventor: John D. Dobak, La Jolla, CA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 995 days.

(21) Appl. No.: 11/811,697

(22) Filed: Jun. 11, 2007

(65) Prior Publication Data
US 2008/0033511 A1    Feb. 7, 2008

Related U.S. Application Data

(63) Continuation-in-part of application No. 11/657,877, filed on Jan. 24, 2007, now Pat. No. 7,702,386, which is a continuation-in-part of application No. 11/338,388, filed on Jan. 24, 2006, now Pat. No. 7,689,277, which is a continuation-in-part of application No. 10/920,734, filed on Aug. 18, 2004, now Pat. No. 7,689,276, which is a continuation-in-part of application No. 10/785,726, filed on Feb. 24, 2004, now Pat. No. 7,551,964, which is a continuation-in-part of application No. 10/272,430, filed on Oct. 16, 2002, now Pat. No. 7,236,822, which is a continuation-in-part of application No. 10/243,612, filed on Sep. 13, 2002, now Pat. No. 7,239,912.

(60) Provisional application No. 60/366,750, filed on Mar. 22, 2002, provisional application No. 60/370,311, filed on Apr. 5, 2002, provisional application No. 60/379,605, filed on May 10, 2002, provisional application No. 60/384,219, filed on May 30, 2002, provisional application No. 60/386,699, filed on Jun. 10, 2002, provisional application No. 60/804,415, filed on Jun. 9, 2006.

(51) Int. Cl.
*A61N 1/36* (2006.01)
(52) U.S. Cl. ........................................................ 607/2
(58) Field of Classification Search .................. 600/373, 600/377, 593; 607/2, 115, 116, 118, 133
See application file for complete search history.

(56) References Cited

U.S. PATENT DOCUMENTS 3,911,930 A    10/1975    Hagfors et al.
(Continued)

FOREIGN PATENT DOCUMENTS

WO    WO 98/57701    12/1998
(Continued)

OTHER PUBLICATIONS

Accornero, Neri, et al., Selective Activation of Peripheral Nerve Fibre Groups of Different Diameter by Triangular Shaped Stimulus Pulses, *J. Physiol.*, 1977, 539-560, vol. 273.

(Continued)

*Primary Examiner* — Carl H Layno
*Assistant Examiner* — Frances P Oropeza
(74) *Attorney, Agent, or Firm* — Craig Hoersten; Christopher S. L. Crawford; Peter Lando

(57) ABSTRACT

Described are apparatus and methods for electrically modulating a nerve in a mammal. An electrical signal that includes a signal intensity pattern and a signal frequency pattern is delivered to a nerve. The combination of the signal intensity pattern and the signal frequency pattern is effective to result in weight loss, fat loss, and/or lean-mass gain, in a mammal. In some embodiments the nerve is modulated in response to a physiological parameter. In some embodiments, the physiological parameter is measured by a sensor.

54 Claims, 38 Drawing Sheets

U.S. PATENT DOCUMENTS

| | | |
|---|---|---|
| 4,573,481 A | 3/1986 | Bullara |
| 4,595,010 A | 6/1986 | Radke |
| 4,827,935 A | 5/1989 | Geddes et al. |
| 4,867,164 A | 9/1989 | Zabara |
| 5,095,905 A | 3/1992 | Klepinski |
| 5,107,833 A | 4/1992 | Barsness |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,251,634 A | 10/1993 | Weinberg |
| 5,263,480 A | 11/1993 | Wernicke et al. |
| 5,269,303 A | 12/1993 | Wernicke et al. |
| 5,281,581 A | 1/1994 | Cooper et al. |
| 5,299,569 A | 4/1994 | Wernicke et al. |
| 5,304,206 A | 4/1994 | Baker, Jr. et al. |
| 5,330,515 A | 7/1994 | Rutecki et al. |
| 5,335,657 A | 8/1994 | Terry, Jr. et al. |
| 5,351,394 A | 10/1994 | Weinberg |
| 5,423,872 A | 6/1995 | Cigaina |
| 5,454,840 A | 10/1995 | Krakovsky et al. |
| 5,458,626 A | 10/1995 | Krause |
| 5,531,778 A | 7/1996 | Maschino et al. |
| 5,540,730 A | 7/1996 | Terry, Jr. et al. |
| 5,540,734 A | 7/1996 | Zabara |
| 5,571,150 A | 11/1996 | Wernicke et al. |
| 5,690,691 A | 11/1997 | Chen et al. |
| 5,707,400 A | 1/1998 | Terry, Jr. et al. |
| 5,716,392 A | 2/1998 | Bourgeois et al. |
| 5,725,563 A | 3/1998 | Klotz |
| 5,755,750 A | 5/1998 | Petruska et al. |
| 5,782,798 A | 7/1998 | Rise |
| 5,836,994 A | 11/1998 | Bourgeois |
| 5,919,216 A | 7/1999 | Houben et al. |
| 5,928,272 A | 7/1999 | Adkins et al. |
| 5,995,872 A | 11/1999 | Bourgeois |
| 6,041,258 A | 3/2000 | Cigaina |
| 6,068,596 A | 5/2000 | Weth et al. |
| 6,109,269 A | 8/2000 | Rise et al. |
| 6,129,685 A | 10/2000 | Howard, III |
| 6,146,391 A | 11/2000 | Cigaina |
| 6,165,180 A | 12/2000 | Cigaina |
| 6,169,924 B1 | 1/2001 | Meloy et al. |
| 6,308,105 B1 | 10/2001 | Duysens et al. |
| 6,321,124 B1 | 11/2001 | Cigaina |
| 6,350,455 B1 | 2/2002 | Donovan |
| 6,356,786 B1 | 3/2002 | Rezai et al. |
| 6,356,787 B1 | 3/2002 | Rezai et al. |
| 6,381,495 B1 | 4/2002 | Jenkins |
| 6,438,423 B1 | 8/2002 | Rezai et al. |
| 6,497,718 B1 | 12/2002 | Dewan |
| 6,542,776 B1 | 4/2003 | Gordon et al. |
| 6,558,320 B1 | 5/2003 | Causey et al. |
| 6,587,719 B1 | 7/2003 | Barrett et al. |
| 6,721,603 B2 | 4/2004 | Zabara et al. |
| 6,885,888 B2 | 4/2005 | Rezai |
| 6,912,419 B2 | 6/2005 | Hill et al. |
| 6,922,590 B1 | 7/2005 | Whitehurst |
| 7,076,292 B2 | 7/2006 | Forsberg |
| 7,155,278 B2 | 12/2006 | King et al. |
| 2001/0014815 A1 | 8/2001 | Matsumura et al. |
| 2002/0072780 A1 | 6/2002 | Foley |
| 2002/0077675 A1 | 6/2002 | Greenstein |
| 2002/0099419 A1 | 7/2002 | Cohen et al. |
| 2003/0018367 A1 | 1/2003 | DiLorenzo |
| 2003/0045909 A1 | 3/2003 | Gross et al. |
| 2003/0144708 A1 | 7/2003 | Starkebaum |
| 2003/0181958 A1 | 9/2003 | Dobak, III |
| 2004/0230255 A1 | 11/2004 | Dobak, III |
| 2005/0065575 A1 | 3/2005 | Dobak |
| 2005/0143788 A1 | 6/2005 | Yun et al. |
| 2005/0149146 A1 | 7/2005 | Boveja et al. |
| 2010/0216709 A1* | 8/2010 | Scheule et al. ............. 514/12 |

FOREIGN PATENT DOCUMENTS

| | | |
|---|---|---|
| WO | WO 00/61223 | 10/2000 |
| WO | WO 01/52932 | 7/2001 |
| WO | WO 01/58520 | 8/2001 |
| WO | WO 01/83028 | 11/2001 |
| WO | WO 02/04068 | 1/2002 |
| WO | WO 02/26315 | 4/2002 |
| WO | WO 02/26317 | 4/2002 |
| WO | WO 02/34331 | 5/2002 |
| WO | WO 02/43467 | 6/2002 |
| WO | WO 02/062291 | 8/2002 |

OTHER PUBLICATIONS

Ahren, B., Autonomic regulation of islet hormone secretion—Implications for health and disease, Diabetologia, 2000, 393-410, vol. 43.

Ahren, B., Sympathetic Nerve Stimulation Versus Pancreatic Norepinephrine Infusion in the Dog: 1)Effects on Basal Release of Insulin and Glucagon; Endocrinology, 1987; pp. 323-331; vol. 121, No. 1.

Alamo, L..., Electrically-Evoked Catecholamine Release from Cat Adrenals; Biochemical Pharmacology, Nov. 1990, 973-978, vol. 42, No. 5.

Alvarez, et al., Sympathetic Neural Activation in Visceral Obesity, Circulation, Nov. 12, 2002, pp. 2533-2536.

Andrews, P.L.R., et al., Interactions Between Splanchnic and Vagus Nerves in the Control of Mean Intragastric Pressure in the Ferret, *J. Physiol.*, 1984, 473-490, vol. 351.

Andrews, Russell J., Neuromodulation I. Techniques—Deep Brain Stimulation, Vagus Nerve Stimulation, and Transcranial Magnetic Stimulation, Ann. N.Y. Acad. Sci., 2003, 1-13, vol. 993.

Ballard, K. et al., The Unresponsiveness of Lipid Metabolism in Canine Mesenteric Adipose Tissue to Biogenic Amines and to Sympathetic Nerve Stimulation, Acta Physiol. Scan. 1969, 442-448, vol. 77.

Barone, et al., Gastric Distension Modulates Hypothalamic Neurons Via a Sympathetic Afferent Path Through the Mesencephalic Periaqueductal Gray; Brain Research Bulletin; 1995, pp. 239-251, vol. 38, No. 3.

Becker, M.D., James M., et al., Myoelectric control of gastrointestinal and biliary motility: A review, *Surgery*, 1981, 466-477, vol. 89, No. 4.

Binks, et al., High Strength Stimulation of the Vagus Nerve in Awake Humans: A Lack of Cardiorespiratory Effects, Respiration Physiology, 2001, 125-133, vol. 127.

Birks, R.I., Regulation by Patterned Preganglionic Neural Activity of Transmitter Stores in a Sympathetic Ganglion, J. Physiol., 1978, 559-572, vol. 280.

Blackshaw, L. A., et al., Vagal and sympathetic influences on the ferret lower oesophageal sphincter, *Journal of the Autonomic Nervous System*, 1997, 179-188, vol. 66.

Bloom, S., The Andrenal Contribution to the Neuroendocrine Responses to Splanchnic Nerve Stimulation in Conscious Calves, Journal of Physiology, Jul. 1987, 513-526, vol. 397.

Bray, Reciprocal relation of food intake and sympathetic activity: experimental observations and clinical implications, International Journal of Obesity, 2000, pp. S8-S17, 24, Suppl. 2.

Brown, et al., Changes in Food Intake with Electrical Stimulation of the Ventromedial Hypothalamus in Dogs, J Neurosurg, Jun. 1984, pp. 1253-1257, vol. 60.

Buckley, N., Circulatory Effects of Splanchnic Nerve Stimulation in Developing Swine; American Journal of Physiology, Apr. 1984, pp. H69-H74, vol. 248.

Bugbee, Martin, et al., Webpage, 1996, Design of a Selective Nerve Stimulator.

Cigaina, et al., Gastric Peristalsis Control by Mono Situ Electrical Stimulation: a Preliminary Study, Obesity Surgery, 1996, 247-249, vol. 6.

Cigaina, V., Long-Term Effects of Gastric Pacing to Reduce Feed Intake in Swine, Obesity Surgery, 1996, 250-253, vol. 6.

Crago, et al., The Choice of Pulse Duration for Chronic Electrical Stimulation via Surface, Never, and Intramuscular Electrodes, Annals of Biomedical Engineering, 1974, 252-264, vol. 2.

Cummings, D., Plasma Ghrelin Levels after Diet-Induced Weight Loss r Gastric Bypass Surgery; The New England Journal of Medicine, May 2002, 1623-1630, vol. 346, No. 21.

Cuschieri, A., Bilateral Endoscopic Splanchnicectomy through a Posterior Thoracoscopic Approach; J.R. Coll. Surg. Edinb., Feb. 1994, 44-47, vol. 39.

Delbro, D., et al., Non-ganglionic cholinergic excitatory pathways in the sympathetic supply to the feline stomach, *Acta Physiol Scand.*, 1980, 137-144, vol. 110.

Deloof, S., Sympathetic control of antral and pyloric electrical activity in the rabbit, *Journal of the Autonomic Nervous System*, 1988, 1-10, vol. 22.

Dodt, C., et al., Sympathetic control of white adipose tissue in lean and obese humans, *Acta Physiol. Scand.*, 2003, 351-357, vol. 177.

Dodt, Christoph, et al., Intraneural stimulation elicits an increase in subcutaneous interstitial glycerol levels in humans, *Journal of Physiology*, 1999, 545-552, vol. 521.2.

Dodt, Christoph, et al., The Subcutaneous Lipolytic Response to Regional Neural Stimulation is Reduced in Obese Women, *Diabetes*, Nov. 2000, 1875-1879, vol. 49:1.

Dunning, et al., Pancreatic and Extrapancreatic Galanin Release During Sympathetic Neural Activiation, Am J Physiol Endocrinol Metab, Mar. 1990, 436-444, vol. 258.

Edwards, A., Adrenal Catecholamine Output in Response to Stimulation of the Splanchnic Nerve in Bursts in the Conscious Calf, Journal of Physiology, Sep. 1981, 409-419, vol. 327.

Edwards, A., Adrenal Medullary Responses to Stimulation of the Splanchnic Nerve in the Conscious Calf; Journal of Physiology, Jan. 1980, 15-27, vol. 308.

Edwards, A., The Effect of Splanchnic Nerve Stimulation on Adrenocortical Activity in Conscious Calves; Journal of Physiology, Apr. 1986, 385-396, vol. 382.

Edwards, A., The Glycogenolytic Response to Stimulation of the Splanchnic Nerves in Adrenalectomized Calves, Sheep, Dogs, Cats, and Pigs, Journal of Physiology, Nov. 1970, 741-759, vol. 213.

Edwards, A., The Sensitivity of the Hepatic Gylcogenolytic Mechanism to Stimulation of the Splanchnic Nerves, J. Physiol., 1972, 315-334, vol. 220.

Edwards, et al., The Effect of Splanchnic Nerve Stimulation on the Uptake of Atrial Natriuretic Peptide by the Adrenal Gland in Conscious Calves, J. Endocrinol. Invest., 1990, 887-892, vol. 13.

Engeland, W., Splanchnic Nerve Stimulation Modulates Steroid Secretion in Hypophysectomized Dogs; Neuroendocrinology, Agu. 1988, 124-131, vol. 50.

Fang, Zi-Ping, et al., Alternate excitation of large and small axons with different stimulation waveforms: an application to muscle activation, *Med. & Bio. Eng. & Comput.*, 1991, 543-547, vol. 29.

Fredholm, B. B., et al., Effects of Vasoactive Drugs on Circulation in Canine Subcutaneous Adiopose Tissue, Acta Physiol. Scand., 1970, 564-574, vol. 79.

Friesen , et al., Canadian Journal of Physiology and Pharmacology, The National Research Council of Canada, vol. 49, May 1971, No. 5, pp. 375-381.

Fukushima, K., et al., Differential Blocking of Motor Fibers by Direct Current, *Pflügers* Arch., 1975, 235-242, vol. 358.

Furness, J., Effects of Vagal and Splanchnic Section on Food Intake, Weight, Serum Leptin, and Hypothalamic Neuropeptide Y in Rat, Autonomic Neuroscience: Basic and Clinical, Feb. 2001; pp. 28-36; vol. 92.

Hammond, et al., Vagus Nerve Stimulation in Humans: Neurophysiological Studies and Electrophysiological Monitoring, Epilepsia, 1990, pp. S51-S59, vol. 31, Suppl. 2.

Heck, et al., Vagus Nerve Stimulation Therapy, Epilepsy, and Device Parameters, Neurology 59, Suppl 4, Sep. 2002, pp. S31-S37.

Holst, et al. Nervous Control of Pancreatic Exocrine Secretion in Pigs, Acta Physiol. Scand., 1979, 33-51, vol. 105.

Hopp, F.A., et al., Effect of anodal blockade of myelinated fibers on vagal C-fiber afferents, *The American Physiological Society*, 1980.

Itina, L.V., et al., Impulsation of the splanchnic and vagus nerves after introduction of fat into the lumen of the small intestine, Sechnov Physiological Journal of the USSR, Institute of Physiology Acad. Sci. BSSR, Minsk, 1972 (Russian text with English abstract).

Itina, L.V., Sympatho-activatory and sympatho-inhibitory afferent fibers of vagus and splanchnic nerves, Sechenov Physiological Journal of the USSR, Institute of Physiology Acad. Sci. Belorus. SSR, Minsk, 1979 (Russian text with English abstract).

Ito, Shigeo, et al., Gastric Vasodilator and Motor Responses to Splanchnic Stimulation and Tachykinins in the Dog, *Gen. Pharmac*, 1993, 291-298, vol. 24, No. 2.

Jarhult, M.D., et al., The Functional Importance of Sympathetic Nerves to the Liver and Endocrine Pancreas, Ann. Surg., Jan. 1979, 96-100, vol. 189, No. 1.

Jaw, F.-S, et al., A modified "triangular pulse" stimulator for C-fibers stimulation, *Journal of Neuroscience* Methods, 1991, 169-172, vol. 37.

Jonson, et al., Splanchnic Nerve Stimulation Inhibits Duodenal HCO3 Secretion in the Rat, American Physiological Society, 1988, pp. G709-G712.

Jorum, et al., Analgesia by low-frequency nerve stimulation mediated by low-threshold afferents in rats, Pain, 1988, 357-366, vol. 32.

Kaneto, A., et al., *Effect of splanchnic nerve stimulation on glucagons and insulin output in the dog*, Endocrinolgy, Jan. 1975, 96(1): 143-50.

Koo, et al., Human Vagus Nerve Electrophysiology, J Clin Neurophysiol, Sep. 2001, 18(5), pp. 429-433.

Kuo, D., A Wide Field Electron Microscope Analysis of the Fiber Constituents of the Major Splanchnic Nerve in Cat, The Journal of Comparative Neurology, Apr. 1982, pp. 49-58, vol. 210.

Kurose, T., Mechanism of Sympathetic Neural Regulation of Insulin, Somatostatin, and Glucagon Secretion; American Journal of Physiology, Mar. 1989, pp. E220-E227; vol. 258.

Lerman, M.D., Sheldon H., et al., Gastric Motor Response to Sympathetic Nerve Stimulation, Journal of Surgical Research, 1982, 15-23, vol. 32.

Lerman, M.D., Sheldon H., et al., Pyloric motor response to sympathetic nerve stimulation in dogs, *Surgery*, 1981, 460-465, vol. 89, No. 4.

Lockard, et al., Feasibility and Safety of Vagal Stimulation in Monkey Model, Epilepsia ,, 1990, pp. S20-S26, vol. 31, Suppl. 2.

Monroe, Mary Beth, et al., Direct Evidence for Tonic Sympathetic Support of Resting Metabolic Rate in Healthy Adult Humans, Am. J. Physiol Endocrinol Metab., 2001, pp. E740-E744, vol. 280.

Naidoo, N., *Thoracic Splanchnic Nerves: Implications for Splanchnic Denervation*, Journal of Anatomy, Jun. 2001, pp. 585-590. vol. 199.

Nakazato, Yoshikazu, et al., Atropine- and hexamethonium-resistant motor response to greater splanchnic nerve stimulation in the dog stomach, *Journal of the Autonomic Nervous System*,1987, 35-42, vol. 20.

Nakazato, Yoshikazu, et al., Gastric Motor and Inhibitor Response to Stimulation of the Sympathetic Nerve in the Dog, *Jap. J. Pharmac*, 1970, 20: 131-141.

Opsahl, Charles A., Sympathetic nervous system involvement in the lateral hypothalamic lesion syndrome, *Department of Psychology, Yale University, New Haven Connecticut* 06520, Jul. 7, 1976.

Oro, Lars, et al., Influence of Electrical Supramedullary Stimulation on the Plasma Level of Free Fatty Acids, Blood Pressure and Heart Rate in the Dog, *Acta Medica Scandinavica*, 1965, 697-711, vol. 178.

Pan, et al., Role of Summation of Afferent Input in Cardiovascular Reflexes from Splanchnic Nerve Stimulation, The American Physiological Society, 1996, pp. H849-H856.

Peterson, H., Body Fat and the Activity of the Autonomic Nervous System; The New England Journal of Medicine, Apr. 1988, 1078-1083, vol. 318, No. 17.

Rosell, Sune, Release of Free Fatty Acids from Subcutaneous Adipose Tissue in Dogs Following Sympathetic Nerve Stimulation, *Acta Physiol. Scand.*, 1966, 67:343-351.

Rozman, et al., Multielectrode Spiral Cuff for Selective Stimulation of Nerve Fibres, Journal of Medical Engineering & Technology, Sep./Oct. 1992, pp. 194-203, vol. 16, No. 5.

Rozman, J., et al., Recording of ENGs from the nerves innervating the pancreas of a dog during the intravenous glucose tolerance test, National Library of Medicine, Physiol Meas., Nov. 2002, 695-705, 23(4).

Rozman, Janez, et al., Recording of electroneurograms from the nerves innervating the pancreas of a dog, *Journal of Neuroscience Methods*, 2001, 112:155-162.

Rozman, Janez, et al., Stimulation of Nerves Innervating the Dog's Pancreas, *Artificial Organs*, 2002, 26(3):241-243.

Sato, T, et al., Novel therapeutic strategy against central baroreflex failure: a bionic baroreflex system, *National Library of Medicine*, Jul. 20, 1999, 100(3):299-304.

Shimazu, T., Central Nervous System Regulation of Liver and Adipose Tissue Metabolism, *Diabetologia*, 1981, 343-356, vol. 20.

Stoddard, et al., Adrenal Medullary Secretion with Splanchnic Stimulation in Spinal Cats, Journal of the Autonomic Nervous System, 1992, 105-116, vol. 38.

Strickland, T., Performance of Local Anesthetic and Placebo Splanchnic Blocks via Indwelling Catheters to Predict Benefit from Thoracoscopic Splanchnicectomy in a Patient with Intractable Pancreatic Pain, Anesthesiology, Jun. 1995, 980-983, vol. 84.

Sweeney, James D., et al., An Asymmetric Two Electrode Cuff for Generation of Unidirectionally Propagated Action Potentials, IEEE Transactions on Biomedical Engineering, 1986, 541-549, vol. BME-33, No. 6.

Terry, et al., An Implantable Neurocybernetic Prosthesis System, Epilepsia, 1990, pp. S33-S37, vol. 31, Suppl. 2.

Thoren, Peter, et al., Anodal block of medullated cardiopulmonary vagal afferents in cats, *J. Appl. Physiol.: Respir. Environ. Exercise Physiol.*, 1977, 461-465, vol. 42.

Tran, M.A., et al., Adrenergic Neurohumoral Influences of FFA Release From Bone Marrow Adipose Tissue, J. Pharmacol (Paris), 1985, 16, 2, 171-179.

University of Florida Research and Graduate Programs (RGP) website http://rgp.ufl.edu/otl/viewTech.html, Method and Apparatus for Allowing Selective Activity in Small Diameter Nerve Fibers.

Upton, et al., Autonomic Stimulation, PACE, Jan. 1991, 50-69, vol. 14.

Van Den Honert, et al., A Technique for Collision Block of Peripheral Nerve: Single Stimulus Analysis, IEEE Transactions on Biomedical Engineering, May 1981, 373-378, vol. BME-28, No. 5.

Van Den Honert, et al., Generation of Unidirectionally Propagated Action Potentials in a Peripheral Nerve by Brief Stimuli, Science, vol. 206, Dec. 14, 1979, pp. 1311-1312.

Wilkinson, H., Percutaneous Radiofrequency Upper Thorac Sympathectomy, Neurosugery, Aug. 1994, 715-725, vol. 38, No. 4.

Woodbury, et al., Effects of Vagal Stimulation on Experimentally Induced Seizures in Rats, Epilepsia, 1990, pp. S7-S19, vol. 31, Suppl. 2.

Xu Gy et al., Modulation of hypothalamic arcuate nucleus on gastric motility in rats, World J. Gastroenterol, 1998, http://wjgnet.com, 4(5): 426-429.

Bolte, E. et al., "Steroid Production from Plasma Cholesterol. II In Vivo Conversion of Plasma Cholesterol to Ovarian Progesterone and Adrenal C10 and C21 Steroids in Humans", JCE&M, vol. 38, No. 3,(1974), pp. 394-400.

Chen, Ke et al., "Induction of Leptin Resistance Through Direct Interaction of C-Reactive Protein with Leptin", Nature Medicine, vol. 12, No. 4,(2006), pp. 425-432

Clutter, William E., "Epinephrine Plasma Metabolic Clearance Rates and Physiologic Thresholds for Metabolic and Hemodynamic Actions in Man", Journal of Clinic Investigations, vol. 66,(1980), pp. 94-101.

Kurose, T. et al., "Glucagon, Insulin, and Somatostatin Secretion in Response to Sympathetic Neural Activation in Streptozotocin-Induce Diabetic Rats. A Study with the Isolated Perfused Rat Pancreas in Vitro", Diabetologia, vol. 35,(1992), pp. 1035-1041.

Mirkin, Bernard L., "Factors Influencing the Selective of Adrenal Medullary Hormones", Journal Pharmacol. Exp. Ther., vol. 132,(1960), pp. 218-225.

Ravussin, Eric "Reduced Rate of Energy Expenditure as a Risk Factor for Body-Weight Gain", New England Journal of Medicine, vol. 318,(1988), pp. 467-472.

Tataranni, P. "From Physiology to Neuroendocrinology: A Reappraisal of Risk Factors of Body Weight Gain in Humans", Diabetes and Metabolism, vol. 24 No. 2,(1998), pp. 108-115.

International Preliminary Report on Patentability for PCT Patent Application PCT/US2007/01847, mailed on Aug. 7, 2008., pp. 12.

Mokdad, A "The Continuing Epidemics of Obesity and Diabetes in the United States", Journal of the American Medical Association, vol. 286, No. 10, (Sep. 2001), pp. 1195-1200.

Sjostrom, L "Epinephrine Sensitivity with respect to Metabolic Rate and Other Variables in Women", American Journal of Physiology, vol. 245., (Sep. 1982), pp. E431-E442.

Staten, M "Physiolotical Increments in Epinephrine Stimulate Metabolic Rate in Humans", American Journal of Physiology, vol. 253, (Nov. 1986), pp. E322-E330.

Katzeff, H "Metabolic Studies in Human Obesity during Overnutrition and Undernutrition: Thermogenic and Hormonal Responses to Norepinephrine, Metabolism", vol. 35, No. 2., (Feb. 1986), pp. 166-175.

Leibel, R. "Changes in Energy Expenditure Resulting from Altered Body Weight", The New England Journal of Medicine, vol. 332, No. 10., (Mar. 1995), pp. 621-628.

Matthews, D. "Effect of Epinephrine on Amino Acid and Energy Metabolism in Humans", American Journal of Physiology, vol. 258., (Sep. 1989), pp. E948-E956.

Ratheiser, K. "Epinephrine Produces a Prolonged Elevation in Metabolic Rate in Humans", American Journal of Nutrition, vol. 68, (Oct. 1997), pp. 1046-1052.

"International Search Report Received for PCT Patent Application No. PCT/US2007/01847, mailed on Nov. 19, 2007", 1 page.

"International Search Report Received for PCT patent Application No. PCT/US2007/13780, mailed on Sep. 23, 2008", 1 page.

* cited by examiner

BALANCED BIPHASE WAVE FOR

ASYMMETRIC WAVE FORM ENHANCED ANODAL BLOCK

FIGURE Y-QUADRAPOLAR BLOCKING ELECTRODE

DYNAMIC NERVE STIMULATION EMPLOYING FREQUENCY MODULATION

RELATED APPLICATIONS

This application is a continuation-in-part application of U.S. patent application Ser. No. 11/657,877, now U.S. Pat. No. 7,702,386, filed Jan. 24, 2007, and entitled "Neural Stimulation for Treatment of Metabolic Syndrome and Type 2 Diabetes," which is a continuation-in-part of U.S. patent application Ser. No. 11/338,388, now U.S. Pat. No. 7,689,277, filed Jan. 24, 2006, and entitled "Neural Stimulation for Treatment of Metabolic Syndrome and Type 2 Diabetes," which is a continuation-in-part of U.S. patent application Ser. No. 10/920,734, now U.S. Pat. No. 7,689,276, filed Aug. 18, 2004, and entitled "Dynamic Nerve Stimulation for Treatment of Disorders," which is a continuation-in-part of U.S. patent application Ser. No. 10/785,726, now U.S. Pat. No. 7,551,964, filed Feb. 24, 2004, and entitled "Splanchnic Nerve Stimulation for Treatment of Obesity," which is a continuation-in-part application of U.S. patent application Ser. No. 10/272,430, now U.S. Pat. No. 7,236,822 filed Oct. 16, 2002, and entitled "Wireless Electric Modulation of Sympathetic Nervous System," which is a continuation-in-part application of U.S. patent application Ser. No. 10/243,612, now U.S. Pat. No. 7,239,912 filed Sep. 13, 2002, and entitled "Electric Modulation of Sympathetic Nervous System," which claims the priority benefit of five U.S. provisional patent applications: U.S. Provisional Patent Application No. 60/366,750, filed Mar. 22, 2002; U.S. Provisional Patent Application No. 60/370,311, filed Apr. 5, 2002; U.S. Provisional Patent Application No. 60/379,605, filed May 10, 2002; U.S. Provisional Patent Application No. 60/384,219, filed May 30, 2002; and U.S. Provisional Patent Application No. 60/386,699, filed Jun. 10, 2002; the present application also claims benefit under 35 U.S.C. §119(e) of U.S. Provisional Application No. 60/804,415, entitled "Dynamic Nerve Stimulation Employing Frequency Modulation," filed Jun. 9, 2006; the entire contents of all of which are incorporated by reference herein.

FIELD OF THE INVENTION

The invention relates to nerve stimulation for the treatment of medical conditions, which may be used together with obesity and other treatment modalities

BACKGROUND OF THE INVENTION

Metabolic syndrome, also known as Syndrome X, insulin resistance syndrome and dysmetabolic syndrome, is a conglomeration of health risks that increase the chance of developing heart disease, stroke and diabetes. Metabolic syndrome is not a disease in and of itself, but rather is a name given to a cluster of metabolic disorders including high blood pressure, high insulin levels, excess body weight and abnormal cholesterol levels. Type II diabetes includes many of the same conditions, signs and laboratory findings as metabolic syndrome, and some experts thus do not draw a distinction between these diseases or conditions, especially when frank hyperglycemia is observed in a patient. Each or these conditions is considered to be a risk factor for certain other diseases, however, combined together, these conditions indicate a significantly higher likelihood of developing a life threatening disease. According to some surveys, more than one in five Americans has metabolic syndrome with a greater preponderance of the syndrome present in people of higher age.

Some medical professionals have questioned the existence of metabolic syndrome as an adequately defined condition, citing the need for additional research in order to better quantify and define the symptoms and risks of the various components of the disease. However, a more clear definition of metabolic syndrome has emerged recently and doctors have developed guidelines for diagnosing it.

The indicators of metabolic syndrome include obesity, and particularly obesity around the waist. A waistline of 40 inches or more for men and 35 inches or more for women would qualify. Another indicator is high blood pressure such as a blood pressure of 130/85 mm Hg or greater. Yet another factor is one or more abnormal cholesterol levels including a high density lipoprotein level (HDL) less than 40 mg/dL for men and under 50 mg/dL for women. A triglyceride level above 150 mg/dL may also be an indicator. Finally, a resistance to insulin is an indicator of metabolic syndrome which may be indicated by a fasting blood glucose level greater than 100 mg/dL.

According to the American Heart Association, three groups of people are often afflicted with metabolic syndrome. The first group includes people with diabetes who can not maintain a proper glucose level. The second group includes people without diabetes who have high blood pressure and who also secrete large amounts of insulin to maintain glucose levels (hyperinsulinemia). Finally, a third group includes people who have survived a heart attack and have hyperinsulinemia without glucose intolerance.

Generally, the underlying cause of metabolic syndrome is believed to be insulin resistance, wherein cells lose their ability to respond to insulin signals to uptake glucose from the blood. When this happens, glucose levels remain high after eating and the pancreas continues to secrete insulin in an effort to return blood glucose levels to normal. This may compensate for the insulin resistance for a while, but eventually the pancreas can not keep up the levels of insulin necessary to maintain proper blood glucose levels by stimulating absorption, and glucose levels continue to increase. Chronic stimulation of insulin-producing cells of the pancreas eventually results in a significant decrease in insulin output, a condition known as Type II diabetes. In this circumstance, onset of metabolic syndrome occurs prior to the onset of Type II diabetes.

As the insulin resistance develops and glucose levels rise, the health risks associated with the high insulin levels begin to take effect. Consistently high levels of insulin and glucose may cause a variety of negative effects such as damage to the lining of arteries which can lead to heart attack or stroke. These abnormal levels can also cause changes in the ability of the kidneys to remove salt, leading to high blood pressure, heart disease and stroke. Other consequences include an increase in triglyceride levels, which can lead to an increased risk of developing cardiovascular disease as well as a slowing of insulin production, which can indicate the onset of Type II diabetes, which in turn can cause heart attack, stroke, as well as damage to the eyes, nerves or kidneys.

The cause of insulin resistance is not well understood. Some researchers believe that a combination of genetics and lifestyle including poor diet and low levels of regular exercise may contribute to the insulin resistance. As such, current treatment methods include addressing the lifestyle and diet components of the cause, primarily to prevent the onset of Type II diabetes, heart attack and stroke. Exercise and weight control, including the development of greater muscle mass helps modulate insulin/glucose levels. A diet low in carbohydrates and alcohol may also help.

Medications may also be prescribed in order to treat the individual risk factors that comprise metabolic syndrome. For example, weight loss drugs such as sibutramine and orlistat to treat obesity, insulin sensitizers such as thiazolidinediones and metformin to treat insulin resistance, aspirin to reduce the threat of heart attack, diuretics, ACE inhibitors, calcium channel and beta blockers to treat hypertension, and medications such as niacin, statins and fibrates to improve cholesterol levels may be prescribed. Unfortunately, compliance is often a major shortcoming with regard to such a treatment regimen. In general, any treatment regimen that involves dramatic lifestyle changes and daily medication runs the risk of low compliance. In addition, some of the medications discussed above may have significant side effects that pose risks to the patient taking them.

SUMMARY OF THE INVENTION

What is needed are systems and methods for the treatment of metabolic syndrome or any of its attendant or contributing components that does not generate compliance problems. What is also needed are systems and methods for treating metabolic syndrome that avoid the risk of side effects inherent in the use of any pharmaceutical.

Experimental forms of treatment for obesity involve electrical stimulation of the splanchnic nerve (sympathetic system) and the vagus nerve (parasympathetic system). These therapies use a pulse generator to stimulate electrically the splanchnic nerve or the vagus nerve via implanted electrodes. The intent of these therapies is to reduce food intake through the promotion of satiety and/or reduction of appetite, and neither of these therapies is believed to affect energy expenditure In certain embodiments, a method for treating at least one of obesity, Type II diabetes, and metabolic syndrome in a patient is disclosed. The method comprises providing a pulse generator, the pulse generator having a programmable stimulation pattern with a signal-on time that comprises a subthreshold period and a suprathreshold period. The method further comprises electrically activating a splanchnic nerve of a patient with the pulse generator, using the stimulation pattern, so as to ameliorate or eliminate an attendant condition of obesity, metabolic syndrome, and Type II diabetes in the patient. The attendant condition comprises at least one of dyslipidemia, hypertension, hyperinsulinemia, hyperglycemia, and insulin resistance, wherein the splanchnic nerve is selected from the group consisting of the greater splanchnic nerve, the lesser splanchnic nerve, and the least splanchnic nerve.

In certain embodiments, the method comprises programming the stimulation pattern so as to keep the patient's blood pressure within safe limits. In certain embodiments, the subthreshold period is zero or about zero seconds. In certain embodiments, the stimulation pattern comprises a stimulation intensity, and the stimulation intensity is between about 0.005 and about 5.0 mA-msec. In certain embodiments, the stimulation pattern comprises a frequency, a pulse width, and a current, the frequency is between about 0.1 Hz and about 50 Hz, the pulse width is between about 100 microseconds and about 1 millisecond, and the current is between about 0.1 mA and about 10 mA. In certain embodiments, the stimulation pattern comprises an signal-on time and an off time, and the off time is no less than the signal-on time. In certain embodiments, the stimulation pattern comprises a substantially continuous signal-on time, wherein the signal-on time is comprised of at least one suprathreshold period and at least one subthreshold period. In certain embodiments, the subthreshold period is no less than the suprathreshold period. In certain embodiments, the suprathreshold period is greater than the subthreshold period. In certain embodiments, the method further comprises providing a first electrical signal to the splanchnic nerve at a first stimulation intensity during a first portion of a first stimulation period, the stimulation period comprises at least one on-time, the on-time comprises at least one of a suprathreshold period and a subthreshold period; applying a second electrical signal to the splanchnic nerve at a second stimulation intensity during a second portion of the first stimulation period; ceasing or substantially reducing the applying of the second signal during a first no-stimulation period; thereafter, applying a third electrical signal to the splanchnic nerve at a third stimulation intensity during a first portion of a second stimulation period, the stimulation period comprises at least one on-time, the on-time comprises at least one of a suprathreshold period and a subthreshold period; applying a fourth electrical signal to the splanchnic nerve at a fourth stimulation intensity during a second portion of the second stimulation period; and ceasing or substantially reducing the applying of the fourth signal during a second no-stimulation period. In certain embodiments, the second stimulation intensity is greater than the first stimulation intensity. In certain embodiments, fourth stimulation intensity is greater than the third stimulation intensity. In certain embodiments, the second stimulation intensity is greater than the first stimulation intensity, and the fourth stimulation intensity is greater than the third stimulation intensity. In certain embodiments, the third stimulation intensity is approximately equal to the first stimulation intensity. In certain embodiments, the duration of the first no-stimulation period is approximately equal to the duration of the second no-stimulation period. In certain embodiments, the duration of the first stimulation period is approximately equal to the duration of the second stimulation period. In certain embodiments, the duration of the first portion of the first stimulation period is approximately equal to the duration of the second portion of the first stimulation period. In certain embodiments, the duration of the first portion of the second stimulation period is approximately equal to the duration of the second portion of the second stimulation period. In certain embodiments, the method comprises applying a first plurality of temporally sequential electrical signals during a first plurality of respective stimulation periods, each of the first plurality of signals having a stimulation intensity that is greater than the stimulation intensity of the preceding signal, each stimulation period comprises at least one on-time, the on-time comprises at least one of a suprathreshold period and a subthreshold period; thereafter, ceasing or substantially reducing electrical stimulation to the splanchnic nerve during a first no-stimulation period; thereafter, applying a second plurality of temporally sequential electrical signals during a second plurality of respective stimulation periods, each of the second plurality of signals having a stimulation intensity that is greater than the stimulation intensity of the preceding signal, each stimulation period comprises at least one on-time, the on-time comprises at least one of a suprathreshold period and a subthreshold period; and thereafter, ceasing or substantially reducing electrical stimulation to the splanchnic nerve during a second no-stimulation period. In certain embodiments, the method comprises electrically stimulating the splanchnic nerve for a first time and at a first stimulation intensity during a first stimulation period, the stimulation period comprises at least one on-time, the on-time comprises at least one of a suprathreshold period and a subthreshold period; thereafter, electrically stimulating the splanchnic nerve for a second time and at a second stimulation intensity during the first stimulation period, the second stimulation intensity being greater than the first stimulation intensity; and thereafter, providing a second period during which electrical stimulation at the splanchnic nerve is absent or substantially less than the second stimulation intensity. In certain embodiments, the attendant condition comprises dyslipidemia. In certain embodiments, the dyslipidemia comprises decreased HDL. In certain embodiments, the dyslipidemia comprises elevated triglycerides. In certain embodiments, the dyslipidemia comprises elevated LDL. In certain embodiments, the attendant condition comprises an elevated blood pressure. In certain embodiments, the attendant condition comprises hyperglycemia. In certain embodiments, the attendant condition comprises hyperinsulinemia. In certain embodiments, the attendant condition comprises insulin resistance.

In certain embodiments, a method to increase lean muscle mass of a patient is disclosed. The method comprises electrically modulating a sympathetic nerve of a patient in a stimulation pattern effective to increase a lean muscle mass of the patient, wherein the stimulation pattern comprises at least one on-time. The on-time comprises at least one of a suprathreshold period and a subthreshold period.

In certain embodiments, a splanchnic nerve of the patient comprises the sympathetic nerve, wherein the splanchnic nerve is selected from the group consisting of the greater splanchnic nerve, the lesser splanchnic nerve, and the least splanchnic nerve. In certain embodiments, the stimulation pattern comprises a frequency, a pulse width, and a current, the frequency is between about 0.1 Hz and about 50 Hz, the pulse width is between about 100 microseconds and about 1 millisecond, and the current is between about 0.1 mA and about 10 mA.

In certain embodiments, a method of stimulating a splanchnic nerve in a mammal is disclosed. The method comprises firstly (1) electrically stimulating the splanchnic nerve for a first time and at a first stimulation intensity during a first stimulation period, the stimulation period comprises at least one on-time, the on-time comprises at least one of a suprathreshold period and a subthreshold period, wherein the splanchnic nerve is selected from the group consisting of the greater splanchnic nerve, the lesser splanchnic nerve, and the least splanchnic nerve. The method further comprises secondly (2) thereafter, electrically simulating the splanchnic nerve for a second time and at a second stimulation intensity during the first stimulation period, the second stimulation intensity being greater than the first stimulation intensity. The method further comprises thirdly (3) thereafter, providing a second period during which electrical stimulation at the splanchnic nerve is less than the first stimulation intensity.

In certain embodiments, the subthreshold period is zero or about zero seconds. In certain embodiments, the method comprises repeating steps 1-3. In certain embodiments, a duration of the second period is configured to minimize weight gain or maximize weight loss in the mammal during the period. In certain embodiments, the method comprises electrically stimulating the splanchnic nerve at least one additional time between the first time and the second time during the first stimulation period. In certain embodiments, the second stimulation intensity is about 1% to about 10,000% greater than the first stimulation intensity. In certain embodiments, the second stimulation intensity is about 2% to about 1,000% greater than the first stimulation intensity. In certain embodiments, the second stimulation intensity is about 4% to about 500% greater than the first stimulation intensity. In certain embodiments, the second stimulation intensity is about 8% to about 100% greater than the first stimulation intensity. In certain embodiments, the second stimulation intensity is about 10% to about 50% greater than the first stimulation intensity. In certain embodiments, the second stimulation intensity is about 15% to about 30% greater than the first stimulation intensity. In certain embodiments, the second stimulation intensity is about 20% greater than the first stimulation intensity. In certain embodiments, the first stimulation intensity is about equal to the threshold for skeletal muscle twitch in the mammal. In certain embodiments, the mammal is a human. In certain embodiments, the first time is between about 30 seconds and about 300 days. In certain embodiments, the first time is between about one minute and about 100 days. In certain embodiments, the first time is between about five minutes and about 50 days. In certain embodiments, the first time is between about 30 minutes and about 30 days. In certain embodiments, the first time is between about one hour and about seven days. In certain embodiments, the first time is between about four hours and about four days. In certain embodiments, the first time is between about six hours and about 36 hours. In certain embodiments, the first time is between about 20 hours and about 28 hours. In certain embodiments, the first time is about 24 hours. In certain embodiments, the second time is between about 30 seconds and about 300 days. In certain embodiments, the second time is between about one minute and about 100 days. In certain embodiments, the second time is between about five minutes and about 50 days. In certain embodiments, the second time is between about 30 minutes and about 30 days. In certain embodiments, the second time is between about one hour and about seven days. In certain embodiments, the second time is between about four hours and about four days. In certain embodiments, the second time is between about six hours and about 36 hours. In certain embodiments, the second time is between about 20 hours and about 28 hours. In certain embodiments, the second time is about 24 hours. In certain embodiments, the first time is approximately equal to the second time. In certain embodiments, the second period is between about 30 seconds and about 300 days. In certain embodiments, the second period is between about one minute and about 100 days. In certain embodiments, the second period is between about five minutes and about 50 days. In certain embodiments, the second period is between about 30 minutes and about 30 days. In certain embodiments, the second period is between about one hour and about 15 days. In certain embodiments, the second period is between about one day and about ten days. In certain embodiments, the second period is between about two days and about seven days. In certain embodiments, the second period is between about three days and about five days. In certain embodiments, the second period is about four days.

In certain embodiments, an implantable pulse generator programmed to modulate electrically a splanchnic nerve in a mammal is disclosed. The implantable pulse generator comprises providing a first electrical signal to the splanchnic nerve at a first stimulation intensity during a first portion of a first stimulation period, the first stimulation period comprises at least one on-time, the on-time comprises at least one of a suprathreshold period and a subthreshold period, wherein the splanchnic nerve is selected from the group consisting of the greater splanchnic nerve, the lesser splanchnic nerve, and the least splanchnic nerve. The implantable pulse generator further comprises providing a second electrical signal to the splanchnic nerve at a second stimulation intensity during a second portion of a first stimulation period. The implantable pulse generator further comprises ceasing or substantially reducing the providing of the second signal during a first no-stimulation period. The implantable pulse generator further comprises thereafter providing a third electrical signal to the splanchnic nerve at a third stimulation intensity during a first portion of a second stimulation period, the second stimulation period comprises at least one on-time, the on-time comprises at least one of a suprathreshold period and a subthreshold period. The implantable pulse generator further comprises providing a fourth electrical signal to the splanchnic nerve at a fourth stimulation intensity during a second portion of a second stimulation period. The implantable pulse generator further comprises ceasing or substantially reducing the providing of the fourth signal during a second no-stimulation period.

In certain embodiments, the implantable pulse generator is configured such that the second stimulation intensity is greater than the first stimulation intensity, and the fourth stimulation intensity is greater than the third stimulation intensity.

In certain embodiments, an implantable pulse generator programmed to modulate electrically a splanchnic nerve in a mammal is disclosed. The implantable pulse generator comprises firstly (1) electrically stimulating the splanchnic nerve for a first time and at a first stimulation intensity during a stimulation period, the stimulation period comprises at least one on-time, the on-time comprises at least one of a suprathreshold period and a subthreshold period, wherein the splanchnic nerve is selected from the group consisting of the greater splanchnic nerve, the lesser splanchnic nerve, and the least splanchnic nerve. The implantable pulse generator further comprises secondly (2) thereafter, electrically simulating the splanchnic nerve for a second time and at a second stimulation intensity during the first stimulation period, the second stimulation intensity being greater than the first stimulation intensity. The implantable pulse generator further comprises thirdly (3) thereafter, providing a second period during which electrical stimulation at the splanchnic nerve is absent or substantially less than the second stimulation intensity.

In certain embodiments, the subthreshold period is zero or about zero seconds. In certain embodiments, the implantable pulse generator is further programmed to repeat steps 1-3. In certain embodiments, the implantable pulse generator is further programmed such that the second stimulation intensity is greater than the first stimulation intensity. In certain embodiments, the implantable pulse generator is further programmed such that the second stimulation intensity is about 20% greater than the first stimulation intensity. In certain embodiments, the implantable pulse generator is further programmed such that the first time is between about four hours and about four days. In certain embodiments, the implantable pulse generator is further programmed such that the second time is between about four hours and about four days. In certain embodiments, the implantable pulse generator is further programmed such that the period is between about two days and about seven days. In certain embodiments, the implantable pulse generator is programmed in hardware to modulate the splanchnic nerve. In certain embodiments, the implantable pulse generator is programmed in software to modulate the splanchnic nerve.

In certain embodiments, a tissue modulation device for treating at least one of obesity, metabolic syndrome, and Type II diabetes in a patient is disclosed. The device comprises a storage module having computer-readable instructions for delivering an electrical stimulation pattern to a splanchnic nerve of the patient, wherein the stimulation pattern comprises at least one on-time. The on-time comprises at least one of a suprathreshold period and a subthreshold period. The splanchnic nerve is selected from the group consisting of the greater splanchnic nerve, the lesser splanchnic nerve, and the least splanchnic nerve. The pattern is effective to ameliorate at least one attendant condition of obesity, metabolic syndrome, and Type II diabetes in the patient. The attendant condition comprises at least one of dyslipidemia, hypertension, hyperinsulinemia, hyperglycemia, and insulin resistance.

In certain embodiments, the device comprises an energy delivery module that is electrically coupled to the storage module, wherein the energy delivery module is configured to deliver electrical energy to the splanchnic nerve of the patient according to the instructions. In certain embodiments, an implantable pulse generator comprises the storage module.

In certain embodiments, a tissue modulation device is disclosed. The device comprises a storage module having computer-readable instructions for delivering an electrical stimulation pattern to a splanchnic nerve, wherein the stimulation pattern comprises at least one on-time. The on-time comprises at least one of a suprathreshold period and a subthreshold period. The splanchnic nerve is selected from the group consisting of the greater splanchnic nerve, the lesser splanchnic nerve, and the least splanchnic nerve. The pattern is effective to result in an increase in the patient's lean muscle mass.

In certain embodiments, the device comprises an energy delivery module that is electrically coupled to the storage module, wherein the energy delivery module is configured to deliver electrical energy to the splanchnic nerve of the patient according to the instructions.

In certain embodiments, a tissue modulation device for treating at least one of obesity, metabolic syndrome, and Type II diabetes in a patient is disclosed. The device comprises means for storing computer-readable instructions for delivering an electrical stimulation pattern to a splanchnic nerve of the patient, wherein the stimulation pattern comprises at least one on-time. The on-time comprises at least one of a suprathreshold period and a subthreshold period. The splanchnic nerve is selected from the group consisting of the greater splanchnic nerve, the lesser splanchnic nerve, and the least splanchnic nerve. The pattern is effective to ameliorate at least one attendant condition of obesity, metabolic syndrome, and Type II diabetes in the patient. The attendant condition comprises at least one of dyslipidemia, hypertension, hyperinsulinemia, hyperglycemia, and insulin resistance.

In certain embodiments, the device comprises means for delivering electrical energy to the splanchnic nerve of the patient in the pattern according to the instructions, the means for delivering electrical energy being electrically coupled to the storage module.

In certain embodiments, a tissue modulation device is disclosed. The device comprises means for storing computer-readable instructions for delivering an electrical stimulation pattern to a splanchnic nerve of the patient, wherein the stimulation pattern comprises at least one on-time. The on-time comprises at least one of a suprathreshold period and a subthreshold period. The splanchnic nerve is selected from the group consisting of the greater splanchnic nerve, the lesser splanchnic nerve, and the least splanchnic nerve. The pattern is effective to result in an increase in the patient's lean muscle mass.

In certain embodiments, the device comprises means for delivering electrical energy to the splanchnic nerve of the patient in the pattern according to the instructions, the means for delivering electrical energy being electrically coupled to the storage module.

In certain embodiments, a method to increase a concentration of HDL in a patient is disclosed. The method comprises electrically modulating a sympathetic nerve of a patient in a stimulation pattern, wherein the stimulation pattern comprises at least one on-time. The on-time comprises at least one of a suprathreshold period and a subthreshold period. The pattern is effective to increase the concentration of HDL of the patient.

In certain embodiments, a splanchnic nerve comprises the sympathetic nerve, wherein the splanchnic nerve is selected from the group consisting of the greater splanchnic nerve, the lesser splanchnic nerve, and the least splanchnic nerve.

In certain embodiments, a method to decrease a concentration of LDL in a patient is disclosed. The method comprises electrically modulating a sympathetic nerve of a patient in a stimulation pattern, wherein the stimulation pattern comprises at least one on-time. The on-time comprises at least one of a suprathreshold period and a subthreshold period. The pattern is effective to decrease the concentration of LDL in the patient.

In certain embodiments, a splanchnic nerve comprises the sympathetic nerve, wherein the splanchnic nerve is selected from the group consisting of the greater splanchnic nerve, the lesser splanchnic nerve, and the least splanchnic nerve.

In certain embodiments, a method to decrease a concentration of serum cholesterol in a patient is disclosed. The method comprises electrically modulating a sympathetic nerve of a patient in a stimulation pattern, wherein the stimulation pattern comprises at least one on-time. The on-time comprises at least one of a suprathreshold period and a subthreshold period. The pattern is effective to decrease the concentration of serum cholesterol in the patient.

In certain embodiments, a splanchnic nerve comprises the sympathetic nerve, wherein the splanchnic nerve is selected from the group consisting of the greater splanchnic nerve, the lesser splanchnic nerve, and the least splanchnic nerve.

In certain embodiments, a method to reduce a concentration of serum triglycerides in a patient is disclosed. The method comprises electrically modulating a sympathetic nerve of a patient in a stimulation pattern, wherein the stimulation pattern comprises at least one on-time. The on-time comprises at least one of a suprathreshold period and a subthreshold period. The pattern is effective to reduce the concentration of serum triglycerides in the patient.

In certain embodiments, a splanchnic nerve comprises the sympathetic nerve, wherein the splanchnic nerve is selected from the group consisting of the greater splanchnic nerve, the lesser splanchnic nerve, and the least splanchnic nerve.

In certain embodiments, a method to treat hypertension in a patient is disclosed. The method comprises electrically modulating a sympathetic nerve of a patient in a stimulation pattern, wherein the stimulation pattern comprises at least one on-time. The on-time comprises at least one of a suprathreshold period and a subthreshold period. The pattern is effective to lower a blood pressure in the patient.

In certain embodiments, a tissue modulation device for treating hypertension in a patient is disclosed. The device comprises means for storing computer-readable instructions for electrically modulating a splanchnic nerve of a patient in a stimulation pattern, wherein the stimulation pattern comprises at least one on-time. The on-time comprises at least one of a suprathreshold period and a subthreshold period. The splanchnic nerve is selected from the group consisting of the greater splanchnic nerve, the lesser splanchnic nerve, and the least splanchnic nerve. The pattern is effective to lower a blood pressure in the patient.

In certain embodiments, a method of treating at least one of obesity, metabolic syndrome, and Type II diabetes is disclosed. The method comprises electrically modulating a splanchnic nerve of a patient in a stimulation pattern that ameliorates or eliminates an attendant condition of obesity, metabolic syndrome, and Type II diabetes, without causing significant net weight loss in a patient. The attendant condition comprises at least one of dyslipidemia, hypertension, hyperinsulinemia, hyperglycemia, and insulin resistance. The stimulation pattern comprises at least one on-time. The on-time comprises at least one of a suprathreshold period and a subthreshold period. The splanchnic nerve is selected from the group consisting of the greater splanchnic nerve, the lesser splanchnic nerve, and the least splanchnic nerve.

In certain embodiments, the stimulation pattern is effective to result in an increase in the patient's lean muscle mass.

In certain embodiments, a tissue modulation device for treating at least one of obesity, metabolic syndrome, and Type II diabetes in a patient is disclosed. The device comprises means for storing computer-readable instructions for delivering an electrical stimulation pattern to a splanchnic nerve of the patient, wherein the stimulation pattern comprises at least one on-time. The on-time comprises at least one of a suprathreshold period and a subthreshold period. The splanchnic nerve is selected from the group consisting of the greater splanchnic nerve, the lesser splanchnic nerve, and the least splanchnic nerve. The pattern is effective to ameliorate at least one attendant condition of obesity, metabolic syndrome, and Type II diabetes in the patient, without causing significant net weight loss. The attendant condition comprises at least one of dyslipidemia, hypertension, hyperinsulinemia, hyperglycemia, and insulin resistance.

In certain embodiments, the stimulation pattern is effective to result in an increase in the patient's lean muscle mass.

In some embodiments, there is provided an implantable medical device that outputs a configured electrical signal effective to modulate a nerve in a mammal; wherein the electrical signal comprises: a stimulation intensity pattern that varies at least one of a current amplitude and a pulse width in the signal; and a stimulation frequency pattern that varies frequency in the signal; wherein the combination of the stimulation intensity pattern and the stimulation frequency pattern in the electrical signal, as applied to a nerve in the mammal, is effective to result in at least one of a loss of fat mass and a gain in lean mass of the mammal.

In some embodiments, the stimulation intensity pattern and stimulation frequency pattern are varied over time, independently of each other.

In some embodiments, the stimulation intensity pattern comprises: stimulating at a first intensity during at least a portion of a first interval; stimulating at a second intensity during at least a portion of a second interval.

In some embodiments, the device is configured to deliver the stimulation intensity pattern at least once in a 24 hour period.

In some embodiments, the first intensity comprises a current of about 2.5 mA to about 5.0 mA. In some embodiments, the second intensity comprises a current of about 0 mA to about 1.0 mA. In some embodiments, the first intensity comprises a current of about 3.5 mA and the second intensity comprises a current of about 0.5 mA.

In some embodiments, the stimulation frequency pattern comprises at least one change in frequency. In some embodiments, at least one change in frequency occurs at a constant rate. In some embodiments, the at least one change in frequency occurs by at least one increment. In some embodiments, the at least one increment of about 1 Hz to about 20 Hz. In some embodiments, the at least one increment of about 2 Hz to about 10 Hz.

In some embodiments, the stimulation frequency pattern comprises: a first stimulation frequency applied during a first portion of the stimulation frequency pattern; a second stimulation frequency applied during a second portion of the stimulation frequency pattern; and a third stimulation frequency applied during a third portion of the stimulation frequency pattern. In some embodiments, the first stimulation frequency is about 10 Hz, the second stimulation frequency is about 20 Hz, and the third stimulation frequency is about 30 Hz.

In some embodiments, the stimulation frequency pattern further comprises a fourth stimulation frequency applied during a fourth portion of the stimulation frequency pattern. In some embodiments, the fourth stimulation frequency is about 40 Hz.

In some embodiments, the device is further configured to deliver the stimulation frequency pattern at least once in a 24 hour period.

In some embodiments, the device is further configured to modulate a sympathetic nerve. In some embodiments, the device is further configured to modulate a splanchnic nerve, wherein the splanchnic nerve comprises at least one of a greater splanchnic nerve, a lesser splanchnic nerve, and a least splanchnic nerve.

In some embodiments, the nerve comprises a parasympathetic nerve. In some embodiments, the nerve comprises a vagus nerve.

In some embodiments, the device is configured to deliver the electrical signal in response to a physiological parameter. In some embodiments, the physiological parameter is at least one of eating, a blood glucose level, a blood insulin level, a blood cholesterol level, a blood HDL level, a blood LDL level, a ghrelin level, a leptin level, a catecholamine level, an adipokine level, and an arterial pressure. In some embodiments, the device further comprises a sensor configured to measure the physiological parameter, and wherein the device is configured to deliver the electrical signal in response to a signal received from the sensor.

In some embodiments, the sensor is positionable within the body of the mammal. In some embodiments, the device is configured to be implanted in a human patient. In some embodiments, the device is configured to deliver the electrical signal in response to a command from the patient.

In some embodiments there is provided a method of electrically modulating a nerve in a mammal, comprising: configuring an electrical signal to comprise: a stimulation intensity pattern that varies at least one of a current amplitude and a pulse width in the signal; and a stimulation frequency pattern that varies frequency in the signal; and applying the electrical signal to a nerve in the mammal; wherein the combination of the stimulation intensity pattern and the stimulation frequency pattern in the electrical signal, as applied to a nerve in the mammal, is effective to result in at least one of a loss of fat mass and a gain in lean mass of the mammal.

In some embodiments, the stimulation intensity pattern and stimulation frequency pattern are varied over time, independently of each other. In some embodiments, the stimulation intensity pattern comprises: stimulating at a first intensity during at least a portion of a first interval; stimulating at a second intensity during at least a portion of a second interval. In some embodiments, the stimulation intensity pattern is repeated at least once in a 24 hour period.

In some embodiments, the first intensity is about 2.5 mA to about 5 mA. In some embodiments, the second intensity is about 0 mA to about 1.0 mA. In some embodiments, the first intensity is about 3.5 mA and the second intensity is about 0.5 mA.

In some embodiments, the stimulation frequency pattern comprises at least one change in frequency. In some embodiments, the at least one change in frequency occurs at a constant rate. In some embodiments, the at least one change in frequency occurs by at least one increment. In some embodiments, the at least one increment is about 1 Hz to about 20 Hz. In some embodiments, the at least one increment is about 2 Hz to about 10 Hz.

In some embodiments of the method, the stimulation frequency pattern comprises: applying the electrical signal at a first stimulation frequency during a first portion of the stimulation frequency pattern; applying the electrical signal at a second stimulation frequency during a second portion of the stimulation frequency pattern; applying the electrical signal at a third stimulation frequency during a third portion of the stimulation frequency pattern.

In some embodiments, the first stimulation frequency is about 10 Hz, the second stimulation frequency is about 20 Hz, and the third stimulation frequency is about 30 Hz. In some embodiments, the method further comprises applying the electrical signal at a fourth stimulation frequency during a fourth portion of the stimulation frequency pattern. In some embodiments, the fourth frequency is about 40 Hz. In some embodiments, the stimulation frequency pattern is repeated at least once in a 24 hour period.

In some embodiments of the method, the nerve comprises a sympathetic nerve. In some embodiments, the nerve comprises a splanchnic nerve, wherein the splanchnic nerve comprises at least one of a greater splanchnic nerve, a lesser splanchnic nerve, and a least splanchnic nerve.

In some embodiments of the method, the nerve comprises a parasympathetic nerve. In some embodiments, the nerve comprises a vagus nerve.

In some embodiments of the method, the electrical signal is applied in response to a physiological parameter. In some embodiments, the physiological parameter comprises at least one of eating, a blood glucose level, a blood insulin level, a blood cholesterol level, a blood HDL level, a blood LDL level, a ghrelin level, a leptin level, a catecholamine level, an adipokine level, and an arterial pressure.

In some embodiments of the method, the electrical signal is applied in response to a signal from a sensor configured to measure the physiological parameter. In some embodiments, the sensor is positionable within the body of the mammal. In some embodiments, the mammal is a human patient. In some embodiments, the electrical signal is applied in response to a command from the patient.

These features of embodiments will become more apparent from the following detailed description when taken in conjunction with the accompanying exemplary drawings.

DETAILED DESCRIPTION OF THE INVENTION

Figure 1:
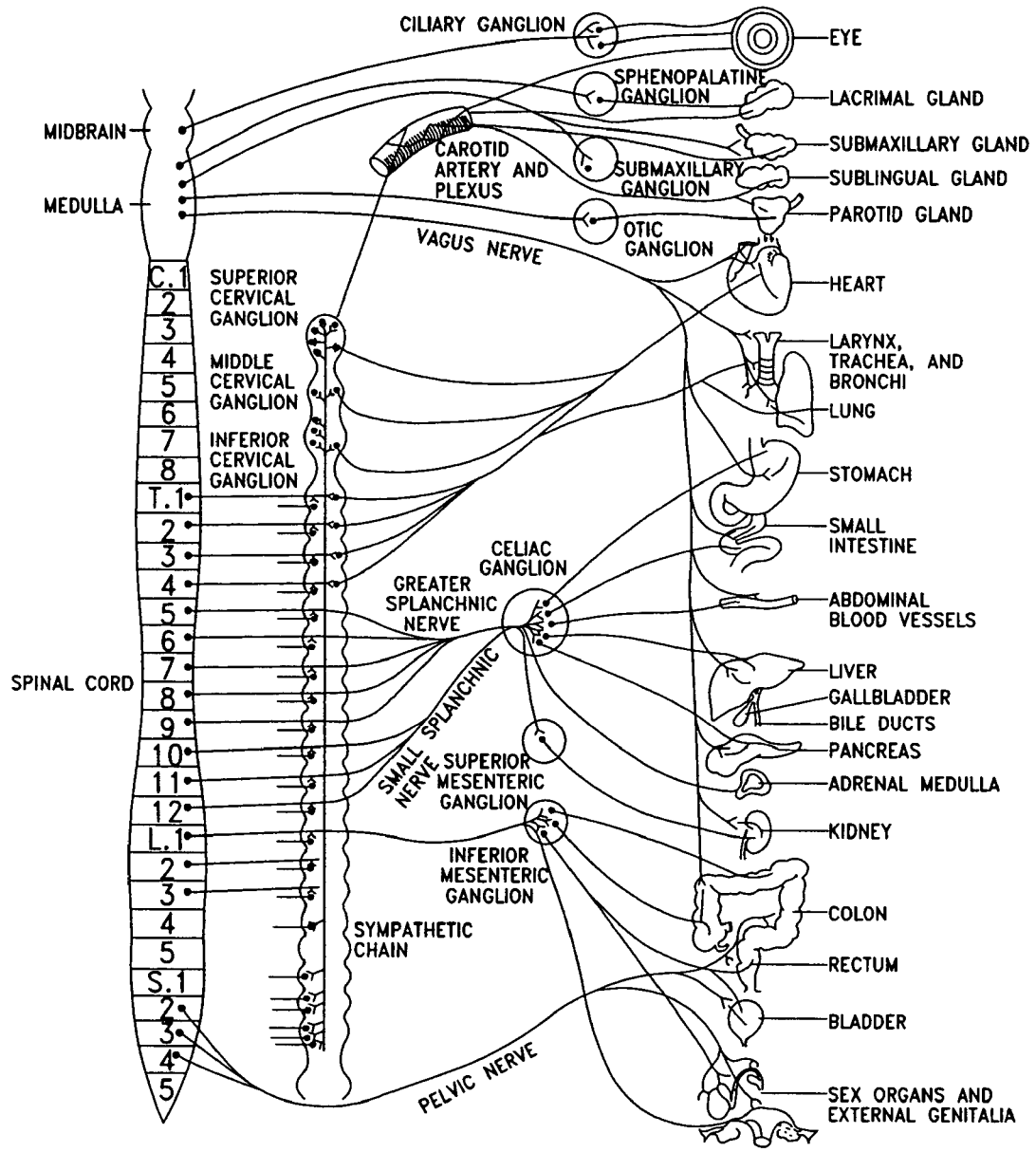
FIG. 1 is a diagrammatic view of an efferent autonomic nervous system of a human.

The invention includes a method for treating obesity, metabolic syndrome, Type II diabetes, or other disorders by electrically activating the sympathetic nervous system with an electrode on or near a nerve, or with a wireless electrode inductively coupled with a radiofrequency field. In some embodiments, obesity (or the other disorders mentioned above) can be treated by activating the efferent sympathetic nervous system, thereby increasing energy expenditure and reducing food intake. Stimulation can be accomplished using a radiofrequency pulse generator and electrodes implanted near, or attached to, various areas of the sympathetic nervous system, such as the sympathetic chain ganglia, the splanchnic nerves (greater, lesser, least), or the peripheral ganglia (e.g., celiac, mesenteric). In some embodiments, the obesity therapy will employ electrical activation of the sympathetic nervous system that innervates the digestive system, adrenals, and abdominal adipose tissue, such as the splanchnic nerves or celiac ganglia. Afferent stimulation can also be accomplished to provide central nervous system satiety. Afferent stimulation can occur by a reflex arc secondary to efferent stimulation. In some embodiments, both afferent and efferent stimulation can be achieved.

This method of obesity treatment may reduce food intake by a variety of mechanisms, including, for example, general increased sympathetic system activation and increasing plasma glucose levels upon activation. Satiety may be produced through direct effects on the pylorus and duodenum that cause reduced peristalsis, stomach distention, and/or delayed stomach emptying. In addition, reducing ghrelin secretion and/or increasing PYY secretion may reduce food intake. The method can also cause weight loss by reducing food absorption, presumably through a reduction in secretion of digestive enzymes and fluids and changes in gastrointestinal motility. Increased stool output, increased PYY concentrations (relative to food intake), and decreased ghrelin concentrations (relative to food intake) may be the result of splanchnic nerve stimulation according to the stimulation parameters disclosed herein.

This method of obesity treatment may also increase energy expenditure by causing catecholamine, cortisol, and dopamine release from the adrenal glands. The therapy can be titrated to the release of these hormones. Fat and carbohydrate metabolism, which are also increased by sympathetic nerve activation, may accompany the increased energy expenditure. Other hormonal effects induced by this therapy may include reduced insulin secretion. Alternatively, this method may be used to normalize catecholamine levels, which are reduced with weight gain.

Electrical sympathetic activation for treating obesity may be accomplished without causing a rise in mean arterial blood pressure (MAP). This can be achieved by using an appropriate stimulation pattern with a relatively short signal-on time (or "on period") followed by an equal or longer signal-off time (or "off period"). In certain embodiments, this may be achieved by using an appropriate stimulation pattern with a continuous signal-on time, wherein the signal-on time is comprised of a relatively short suprathreshold period, during which the energy delivered to a nerve or nerve fiber group meets or exceeds a threshold for exciting that nerve or nerve fiber group, followed by an equal or longer subthreshold period, during which the energy delivered to the nerve or nerve fiber is below the threshold. During activation therapy, a sinusoidal-like fluctuation in the MAP can occur with an average MAP that is within safe limits. Alternatively, an alpha sympathetic receptor blocker, such as prazosin, can be used to blunt the increase in MAP.

Electrical sympathetic activation for treating obesity may be accomplished without permitting a regain of the previously lost weight during the period in which the stimulator is turned off. This can be achieved by using a stimulation time period comprising consecutive periods in which each period has a stimulation intensity greater than the preceding stimulation period. In some embodiments, the stimulation intensity during the first stimulation period is set at about the muscle-twitch threshold. The consecutive stimulation periods are followed by a no-stimulation time period in which the stimulator remains off. Subjects following treatment cycles described by the above pattern have been found to exhibit continued weight loss during the no-stimulation time period in which the stimulator is dormant.

Electrical sympathetic activation for treating obesity may also be accomplished without permitting a regain of the previously lost weight during a subthreshold period. This may be achieved by using a stimulation time period comprising consecutive suprathreshold periods in which each period has a stimulation intensity greater than the preceding suprathreshold stimulation period. In some embodiments, the stimulation intensity during the first suprathreshold stimulation period is set slightly above the muscle-twitch threshold. The consecutive suprathreshold stimulation periods are followed by a subthreshold time period.

Weight loss may be increased if the stimulation patterns are adjusted to prevent the body from compensating for the stimulation. In certain embodiments, this can be achieved by changing the maximum stimulation intensity reached during consecutive groups of stimulation periods, even in the absence of a no-stimulation time period.

A dynamic stimulation technique using ramp-cycling can be used on cranial nerves, the spinal cord, and/or other peripheral nerves, including those in the autonomic system and other motor and sensory nerves.

Electrical sympathetic activation can be titrated to the plasma level of catecholamines achieved during therapy. This would allow the therapy to be monitored and safe levels of increased energy expenditure to be achieved. The therapy can also be titrated to plasma ghrelin levels or PYY levels.

As used herein, electrical "modulation" of a nerve (or nerve fiber) can include excitation (elicitation of one or more action potentials), inhibition, or a combination of these. Electrical "activation" generally includes excitation, but can also include inhibition and/or periods of little or no energy delivery to the nerve (or nerve fiber). Electrical modulation (inhibition or activation) of the sympathetic nerves can also be used to treat other eating disorders such as anorexia or bulimia. For example, inhibition of the sympathetic nerves can be useful in treating anorexia. Electrical modulation of the sympathetic nerves may also be used to treat gastrointestinal diseases such as peptic ulcers, esophageal reflux, gastroparesis, and irritable bowel. For example, stimulation of the splanchnic nerves that innervate the large intestine may reduce the symptoms of irritable bowel syndrome, characterized by diarrhea. Pain may also be treated by electric nerve modulation of the sympathetic nervous system, as certain pain neurons are carried in the sympathetic nerves. This therapy may also be used to treat type II diabetes. These conditions can require varying degrees of inhibition or stimulation.

Attendant or contributing conditions of obesity, metabolic syndrome, and Type II diabetes can include, but are not limited to, obesity, dyslipidemia, hypertension, hyperinsulinemia, elevated plasma glucose levels, hyperglycemia, insulin resistance, a decreased lean muscle mass fraction of total body mass, an increased visceral or abdominal fat fraction of total body mass, or high blood pressure. Dyslipidemia can include, but is not limited to, elevated levels of total cholesterol, elevated levels of triglycerides, elevated levels of LDL, or decreased levels of HDL. One of ordinary skill in the art will understand that ameliorating or treating an attendant or contribution condition of Type II diabetes can be equivalent to ameliorating or treating an attendant condition of metabolic syndrome.

As discussed above, the indicators or attendant or contributing conditions of metabolic syndrome include obesity, and particularly obesity around the waist. A waistline of 40 inches or more for men and 35 inches or more for women would qualify. Another attendant or contributing condition is high blood pressure such as a blood pressure of 130/85 mm Hg or greater. Yet another attendant or contributing condition is one or more abnormal cholesterol levels including a high density lipoprotein level (HDL) less than 40 mg/dl for men and under 50 mg/dl for women. A triglyceride level above 150 mg/dl may also be an indicator. Finally, a resistance to insulin is an indicator of metabolic syndrome which may be indicated by a fasting blood glucose level greater than 100 mg/dl. As such, treatment of one, two, three or more of these indicators of metabolic syndrome may be effective in treatment of metabolic syndrome as it is the conglomeration of several or all of these conditions that results in metabolic syndrome.

Neural stimulation has been used for treatment of various medical conditions including pain management, tremor and the like. Neural stimulation has also been shown to be useful in treating obesity in mammals as well as for regulating certain hormone levels. Embodiments are directed to systems and methods of neural stimulation or modulation including activation and inhibition for treating metabolic syndrome or its attendant or contributing conditions either individually or in combination. Certain embodiments disclosed herein are directed to systems and methods of neural stimulation or modulation. The modulation of nerve tissues such as autonomic nerve tissue including central and peripheral, sympathetic and parasympathetic, may be used to achieve a desired physiological result or treatment of various medical conditions. Specific nerve tissue such as the splanchnic nerve, vagus nerve, stellate ganglia and the like may be modulated in order to achieve a desired result.

The human nervous system is a complex network of nerve cells, or neurons, found centrally in the brain and spinal cord and peripherally in the various nerves of the body. Neurons have a cell body, dendrites and an axon. A nerve is a group of neurons that serve a particular part of the body. Nerves can contain several hundred neurons to several hundred thousand neurons. Nerves often contain both afferent and efferent neurons. Afferent neurons carry signals back to the central nervous system and efferent neurons carry signals to the periphery. A group of neuronal cell bodies in one location is known as a ganglion. Electrical signals are conducted via neurons and nerves. Neurons release neurotransmitters at synapses (connections) with other nerves to allow continuation and modulation of the electrical signal. In the periphery, synaptic transmission often occurs at ganglia.

The electrical signal of a neuron is known as an action potential. Action potentials are initiated when a voltage potential across the cell membrane exceeds a certain threshold. This action potential is then propagated down the length of the neuron. The action potential of a nerve is complex and represents the sum of action potentials of the individual neurons in it.

Neurons can be myelinated and unmyelinated and of large axonal diameter and small axonal diameter. In general, the speed of action potential conduction increases with myelination and with neuron axonal diameter. Accordingly, neurons are classified into type A, B and C neurons based on myelination, axon diameter, and axon conduction velocity. In terms of axon diameter and conduction velocity, A is greater than B which is greater than C.

The autonomic nervous system is a subsystem of the human nervous system that controls involuntary actions of the smooth muscles (blood vessels and digestive system), the heart, and glands, as shown in FIG. 1. The autonomic nervous system is divided into the sympathetic and parasympathetic systems. The sympathetic nervous system generally prepares the body for action by increasing heart rate, increasing blood pressure, and increasing metabolism. The parasympathetic system prepares the body for rest by lowering heart rate, lowering blood pressure, and stimulating digestion.

Figure 2:
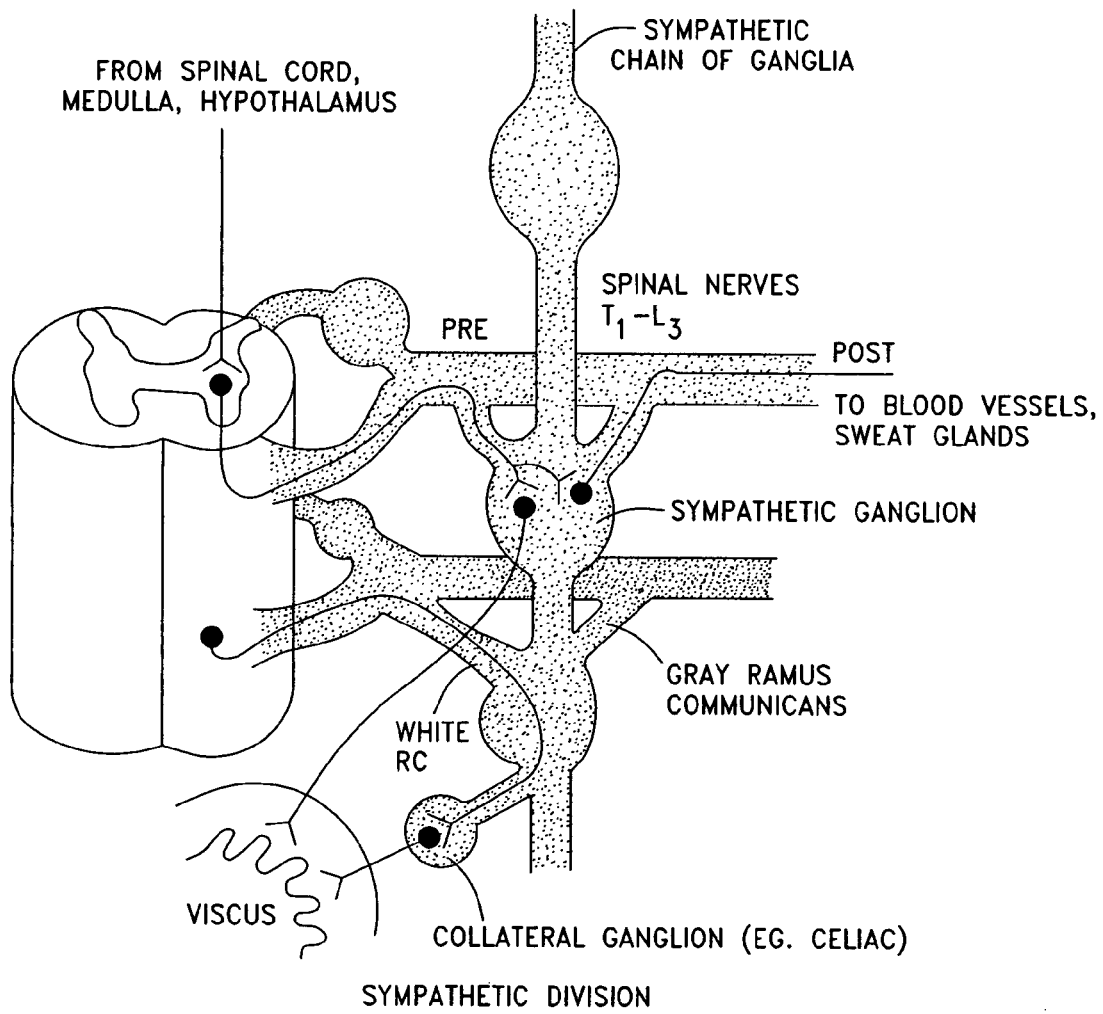
FIG. 2 is a diagrammatic view of a sympathetic nervous system anatomy.

The hypothalamus controls the sympathetic nervous system via descending neurons in the ventral horn of the spinal cord, as shown in FIG. 2. These neurons synapse with preganglionic sympathetic neurons that exit the spinal cord and form the white communicating ramus. The preganglionic neuron will either synapse in the paraspinous ganglia chain or pass through these ganglia and synapse in a peripheral, or collateral, ganglion such as the celiac or mesenteric. After synapsing in a particular ganglion, a postsynaptic neuron continues on to innervate the organs of the body (heart, intestines, liver, pancreas, etc.) or to innervate the adipose tissue and glands of the periphery and skin. Preganglionic neurons of the sympathetic system can be both small-diameter unmyelinated fibers (type C-like) and small-diameter myelinated fibers (type B-like). Postganglionic neurons are typically unmyelinated type C neurons.

Figure 3:
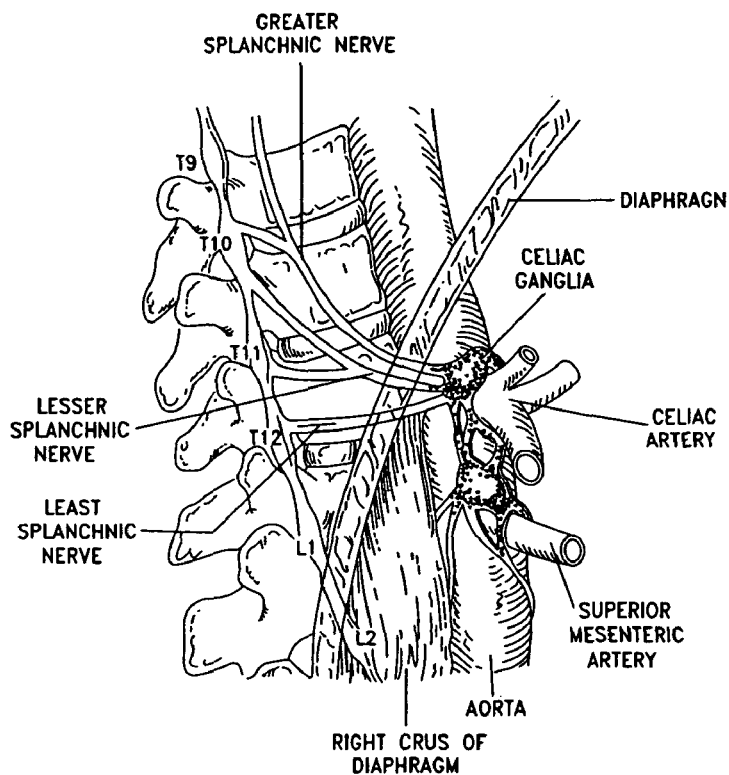
FIG. 3 is an elevation view of the splanchnic nerves and celiac ganglia.

Several large sympathetic nerves and ganglia are formed by the neurons of the sympathetic nervous system as shown in FIG. 3. The greater splanchnic nerve (GSN) is formed by efferent sympathetic neurons exiting the spinal cord from thoracic vertebral segment numbers 4 or 5 (T4 or T5) through thoracic vertebral segment numbers 9 or 10 or 11 (T9, T10, or T11). The lesser splanchnic (lesser SN) nerve is formed by preganglionic fibers sympathetic efferent fibers from T10 to T12 and the least splanchnic nerve (least SN) is formed by fibers from T12. The GSN is typically present bilaterally in animals, including humans, with the other splanchnic nerves having a more variable pattern, present unilaterally or bilaterally and sometimes being absent. The splanchnic nerves run along the anterior lateral aspect of the vertebral bodies and pass out of the thorax and enter the abdomen through the crus of the diaphragm. The nerves run in proximity to the azygous veins. Once in the abdomen, neurons of the GSN synapse with postganglionic neurons primarily in celiac ganglia. Some neurons of the GSN pass through the celiac ganglia and synapse on in the adrenal medulla. Neurons of the lesser SN and least SN synapse with post-ganglionic neurons in the mesenteric ganglia.

Postganglionic neurons, arising from the celiac ganglia that synapse with the GSN, innervate primarily the upper digestive system, including the stomach, pylorus, duodenum, pancreas, and liver. In addition, blood vessels and adipose tissue of the abdomen are innervated by neurons arising from the celiac ganglia/greater splanchnic nerve. Postganglionic neurons of the mesenteric ganglia, supplied by preganglionic neurons of the lesser and least splanchnic nerve, innervate primarily the lower intestine, colon, rectum, kidneys, bladder, and sexual organs, and the blood vessels that supply these organs and tissues.

In the treatment of obesity, some embodiments of treatment involve electrical activation of the greater splanchnic nerve of the sympathetic nervous system. Unilateral activation may be utilized, although bilateral activation may also be utilized. The celiac ganglia can also be activated, as well as the sympathetic chain or ventral spinal roots.

Electrical nerve modulation (nerve activation, stimulation, and/or inhibition) is accomplished by applying an energy signal (pulse) at a certain frequency to the neurons of a nerve (nerve stimulation). The energy pulse causes depolarization of neurons within the nerve above the activation threshold resulting in an action potential. The energy applied is a function of the current (or voltage) amplitude and pulse width or duration. Activation or inhibition can be a function of the frequency of the energy signal, with low frequencies on the order of 1 to 50 Hz resulting in activation of a nerve for some embodiments and high frequencies greater than 100 Hz resulting in inhibition of a nerve for some embodiments. Inhibition can also be accomplished by continuous energy delivery resulting in sustained depolarization. Different neuronal types may respond to different energy signal frequencies and energies with activation or inhibition.

Each neuronal type (i.e., type A, B, or C neurons) has a characteristic pulse amplitude-duration profile (energy pulse signal or stimulation intensity) that leads to activation. The stimulation intensity can be described as the product of the current amplitude and the pulse width. Myelinated neurons (types A and B) can be stimulated with relatively low current amplitudes, on the order of 0.1 to 5.0 mA, and short pulse widths, on the order of about 50 μsec to about 200 μsec. Unmyelinated type C fibers typically require longer pulse widths on the order of about 300 μsec to about 1,000 μsec and higher current amplitudes for stimulation. Thus, in certain embodiments, the stimulation intensity for efferent activation of a nerve may be in the range of about 0.005 mA-msec to about 5.0 mA-msec. In certain embodiments, the stimulation intensity for efferent activation of a nerve may be in the range of about 0.001 mA-msec to about 10.0 mA-msec.

The greater splanchnic nerve also contains type A fibers. These fibers can be afferent and sense the position or state (contracted versus relaxed) of the stomach or duodenum. Stimulation of A fibers may produce a sensation of satiety by transmitting signals to the hypothalamus. They can also participate in a reflex arc that affects the state of the stomach. Activation of both A and B fibers can be accomplished because stimulation parameters that activate efferent B fibers will also activate afferent A fibers. Activation of type C fibers may cause both afferent an efferent effects, and may cause changes in appetite and satiety via central or peripheral nervous system mechanisms.

Various stimulation patterns, ranging from continuous to intermittent, may be utilized for various embodiments. In certain embodiments, information related to a stimulation pattern may be stored in a storage module. For example, stimulation pattern data may be stored in volatile memory, such as random access memory ("RAM"), or in non-volatile memory, such as a hard disk drive or flash drive.

Figure 4:
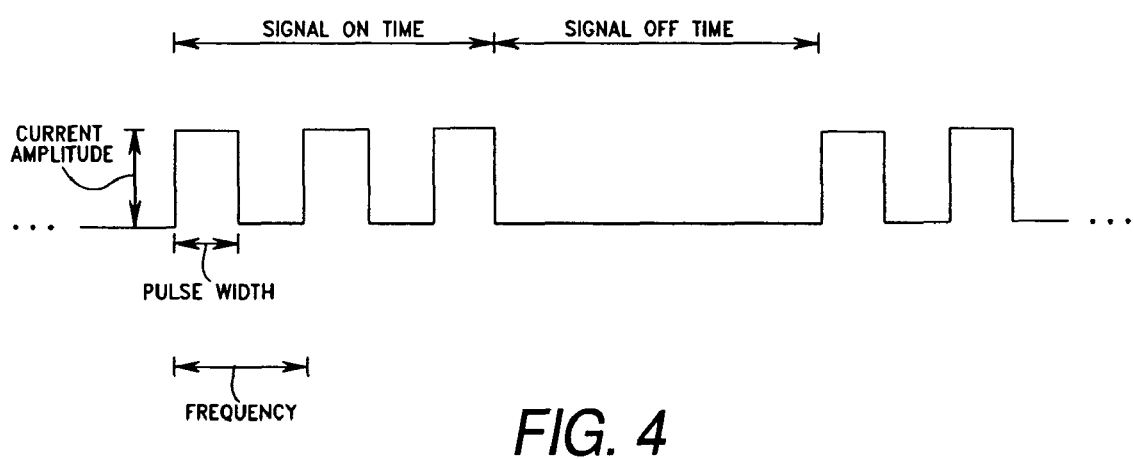
FIG. 4 is a schematic view of an exemplary stimulation pattern.

With intermittent stimulation of nerves, an energy signal is delivered to a nerve or nerve tissue for a period of time at a certain frequency during the signal on-time as shown in FIG. 4. The signal on-time may be followed by a period of time with no energy delivery, referred to as a signal-off time. In certain embodiments, the signal on-time comprises a suprathreshold period, during which the energy delivered to a nerve or nerve fiber group (containing one or more nerve fibers) meets or exceeds a threshold for exciting (i.e., eliciting an action potential from) that nerve or nerve fiber group. In certain embodiments, the signal on-time comprises a subthreshold period, during which the energy delivered to the nerve or nerve fiber is below a threshold for exciting (i.e., eliciting an action potential from) that nerve (or nerve fiber group). Such a subthreshold period may comprise a period of no (or about zero) energy delivery, or an amount of energy greater than zero but less than that needed for exciting the nerve (or fiber). On average, the energy or power delivered to a nerve during a subthreshold period is greater than zero, even if there is one or more brief periods of zero-energy delivery. In certain embodiments as described herein using a signal-on time and signal-off time, a signal-on time may consist of a continuous or nearly continuous suprathreshold period. Consequently, as described herein, the effects of certain embodiments that use a signal-on time and signal-off time may be accomplished using properly configured subthreshold and suprathreshold periods during a continuous or nearly continuous signal-on time.

The ratio of the signal on-time to the sum of the signal on-time plus the signal off time is referred to as the duty cycle and it can, in some embodiments, range from about 1% to about 100%. The ratio of the suprathreshold period to the sum of the suprathreshold period plus the subthreshold period may also be referred to as a duty cycle and it can, in some embodiments, range from about 1% to about 100%. "Duty cycle" in the first definition above may be clarified as the ratio of the suprathreshold period to the sum of the suprathreshold period plus the subthreshold period (i.e., the total on-time) plus the off-time (i.e., the ratio of the suprathreshold period to the sum of the on-time and off-time). Such a duty cycle can, in some embodiments, also range from about 1% to about 100%. Peripheral nerve stimulation is commonly conducted at nearly a continuous, or 100%, duty cycle. However, an optimal duty cycle for splanchnic nerve stimulation to treat obesity may be less than 75% in some embodiments, less than 50% in some embodiments, or even less than 30% in certain embodiments. This may reduce problems associated with muscle twitching as well as reduce the chance for blood pressure or heart rate elevations caused by the stimulation energy. The on-time may also be important for splanchnic nerve stimulation in the treatment of obesity. Because some of the desired effects of nerve stimulation may involve the release of hormones, on-times sufficiently long enough to allow plasma levels to rise are important. Also, gastrointestinal effects on motility and digestive secretions take time to reach a maximal effect. Thus, an on-time of approximately 15 seconds, and sometimes greater than 30 seconds, may be used.

Superimposed on the duty cycle and signal parameters (frequency, on-time, mAmp, and pulse width) are treatment parameters. Therapy may be delivered at different intervals during the day or week, or continuously. Continuous treatment may prevent binge eating during the off therapy time. Intermittent treatment may prevent the development of tolerance to the therapy. A desirable intermittent therapy embodiment may be, for example, 18 hours on and 6 hours off, 12 hours on and 12 hours off, 3 days on and 1 day off, 3 weeks on and one week off or a another combination of daily or weekly cycling. Alternatively, treatment may be delivered at a higher interval rate, say, about every three hours, for shorter durations, such as about 2 minutes to about 30 minutes. The treatment duration and frequency may be tailored to achieve a desired result. Treatment duration for some embodiments may last for as little as a few minutes to as long as several hours. Also, splanchnic nerve activation to treat obesity may be delivered at daily intervals, coinciding with meal times. Treatment duration during mealtime may, in some embodiments, last from 1 hour to about 3 hours and start just prior to the meal or as much as an hour before.

Efferent modulation of the GSN may be used to control gastric distention/contraction and peristalsis. Gastric distention or relaxation and reduced peristalsis can produce satiety or reduced appetite for the treatment of obesity. These effects may be caused by activating efferent B or C fibers at moderate to high intensities, such as about 1.0 mA to about 5.0 mA current amplitude and about 0.15 to about 1.0 millisecond pulse width and higher frequencies of about 10 Hz to about 20 Hz. Gastric distention may also be produced via a reflex arc involving the afferent A fibers. Activation of A fibers may cause a central nervous system mediated reduction in appetite or early satiety. These fibers may be activated at the lower range of stimulation intensity, for example about 0.05 msec to about 0.15 msec pulse width and about 0.1 to about 1.0 mA current amplitude and higher range of frequencies given above. Contraction of the stomach can also reduce appetite or cause satiety. Contraction can be caused by activation of C fibers in the GSN. Activation of C fibers may also play a role in centrally mediated effects. Activation of these fibers is accomplished at higher stimulation intensities, for example about 5 to about 10 times those of B and A fibers and lower frequencies of less than or equal to about 10 Hz.

Electrical activation of the splanchnic nerve can also cause muscle twitching of the abdominal and intercostal muscles. Stimulation at higher frequencies, for example, frequencies greater than about 15 Hz, reduces the muscle activity, and muscle twitching is least evident or completely habituates at even higher frequencies, for example, frequencies of about 20 Hz to about 30 Hz. During stimulation at an energy signal frequency from about 20 Hz to about 30 Hz, a short contraction of the muscles is observed followed by relaxation, such that there is no additional muscle contraction for the remainder of the stimulation. This may be due to inhibitory neurons that are activated with temporal summation.

The muscle-twitching phenomenon may also be used to help guide the stimulation intensity used for embodiments of therapy to be applied to the patient. Once a threshold of muscle twitching is reached, activation of at least the A fibers has occurred. Increasing the current amplitude beyond the threshold to activate the A fibers increases the severity of the muscle contraction and can increase discomfort. Delivering a therapy with an energy signal substantially at the threshold for muscle twitching, and not substantially higher than the threshold for muscle twitching, helps ensure that the comfort of the patient is maintained, particularly at higher energy signal frequencies.

Once this threshold is reached the pulse width of the energy signal may be increased 1.5 to 2.5 times longer, thereby increasing the total charge delivered to the nerve, without significantly increasing the severity of the muscle twitching. By increasing the pulse width at the current, activation of B-fibers is better ensured. Hence, with an electrode placed in close contact with the nerve, a pulse width between about 0.10 msec and about 0.15 msec and a frequency of about 1 Hz, the current amplitude can be increased until the threshold of twitching is observed which indicates activation of A fibers. This will likely occur between 0.25 mA and about 2.5 mA of current, depending on how close the electrode is to the nerve. It should be noted that patient comfort can be achieved at current amplitudes slightly higher than the muscle twitch threshold, or that effective therapy can be delivered at current amplitudes slightly below the muscle twitch threshold, particularly at longer pulse widths.

Habituation to the muscle twitching may also occur, such that the muscle twitching disappears after a certain time period of treatment. This allows the stimulation intensity to be increased to as much as about 10 times or more than the signal intensity threshold of muscle twitching. This can be done without causing discomfort to the patient and ensures activation of the C fibers. It was previously thought that high stimulation intensities would result in the perception of pain, but this does not appear to be seen in experimental settings. The stimulation intensity of the muscle twitch threshold can also be used to guide therapy in this instance, because the twitch threshold may vary from patient to patient depending on the nerve and contact of the electrode with the nerve. Once the threshold of muscle twitching is determined, the stimulation intensity defined by current multiplied by pulse width, may be increased to about 5 times to about 10 times the intensity of muscle twitch threshold. Habituation may occur by stimulating at the muscle twitch threshold for up to about 24 hours.

Increasing the stimulation intensity after habituation occurs at a first signal intensity level, may bring back the muscle activity and require another period of habituation at the new higher signal intensity level. Thus, the stimulation intensity can be increased in a stepwise manner, allowing habituation to occur at each step until the desired intensity is achieved at about 5 times to about 10 times the original signal intensity threshold for muscle twitch. This may be of interest if intermittent treatment frequency is used, as the habituation process up to the desired stimulation intensity would have to occur after each interval when the device is off. The device may be programmed to allow a prolonged ramp up of intensity over about several hours to about several days, allowing habituation to occur at each signal intensity level. This is not the same as the rapid rise in current amplitude that occurs at the beginning of each on-time during stimulation. This may be built or programmed directly into the pulse generator or controlled/programmed by the physician, who can take into account patient variability of habituation time. In some embodiments, the device may be configured to sense muscle twitching. One way to do this is to implant the implantable pulse generator (IPG) over the muscles that are activated. The IPG can then electrically or mechanically sense the twitching and increase the stimulation intensity as habituation occurs.

Efferent electrical activation of the splanchnic nerve can cause an increase in blood pressure, for example, the mean arterial blood pressure (MAP), above a baseline value. A drop in MAP below the baseline can follow this increase. Because a sustained increase in MAP is undesirable, the stimulation pattern can be designed to prevent an increase in MAP. One strategy would be to have a relatively short signal on-time followed by a signal-off time of an equal or longer period. Another strategy would be to have a continuous signal on-time comprised of a relatively short suprathreshold period followed by an equal or longer subthreshold period. This would allow the MAP to drop back to or below the baseline. The subsequent signal on-time would then raise the MAP, but it can start from a lower baseline. In this manner a sinusoidal-like profile of the MAP can be set up during therapy delivery that would keep the average MAP within safe limits.

During stimulation the MAP may rise at a rate of about 0.1 mmHg/sec to about 1.0 mmHg/sec depending on frequency of the stimulation signal, with higher frequencies causing a more rapid rise. An acceptable transient rise in MAP would be about 10-20% of a patient's baseline. Assuming a normal MAP of 90 mm Hg, a rise of about 9 mm Hg to about 18 mm Hg over baseline would be acceptable during stimulation. Thus a stimulation on-time of approximately 9 seconds to about 54 seconds may be acceptable for some embodiments. The off-time would be greater than the on-time or greater than approximately 60 seconds. Habituation may also occur with the blood pressure changes. This may allow the on-time to be increased beyond about 60 seconds, after habituation has occurred.

In some embodiments, a strategy for treating obesity using splanchnic nerve stimulation includes the stimulation of A fibers. The pulse width of the stimulation signal may be set to about 0.05 msec to about 0.15 msec and the current can be increased to about 0.1 mA to about 0.75 mA until the threshold of muscle twitching is reached. Other parameters may include a frequency range of about 20 Hz to about 30 Hz and an on-time of less than about 60 seconds with a duty cycle of about 20% to about 50%. Once habituation to the rise in MAP occurred the on-time can be increased to greater than about 60 seconds.

In certain embodiments, a strategy for treating obesity by electrical activation of the splanchnic nerve involves stimulating the B and A fibers. This strategy involves stimulating the nerve at intensities of about 2 times to about 3 times the muscle twitch threshold prior to any habituation. The pulse width may be set to a range of about 0.15 msec to about 0.25 msec with the pulse current increased, allowing appropriate habituation to occur, to achieve the desired level above the original muscle twitch threshold. Representative parameters for some embodiments may be the following: current amplitude of about 0.75 mA to about 2.0 mA, pulse width of about 0.15 msec to about 0.25 msec, frequency of about 10 Hz to about 20 Hz, on-time less than about 60 seconds, and an off-time greater than about 60 seconds.

These parameters result in gastric relaxation and reduced peristalsis causing early satiety and activation of distention receptors in the stomach that would send satiety signals back to the central nervous system in a reflex manner. Because the effect of gastric relaxation is sustained beyond the stimulation period, in some embodiments the off-time may be about 0.5 times to about 2.0 times longer than the on-time. This would reduce MAP rise. Once habituation to the MAP rise occurs, the on-time may be increased to greater than about 60 seconds, but the duty cycle for some embodiments may be less than about 50%.

Sometimes it may be desirable to activate all fiber types (A, B and C) of the splanchnic nerve. This can be done by increasing the stimulation intensity to stimulation signal intensity levels of about 8 times to about 12 times the muscle twitch threshold prior to habituation. The pulse width may be set to a level of about 0.25 msec or greater for some embodiments. Representative parameters for such a stimulation signal may include: current amplitude greater than about 2.0 mA, pulse width greater than about 0.25 msec, frequency of about 10 Hz to about 20 Hz, on-time less than about 60 seconds, and an off-time greater than about 60 seconds. Similarly, the on-time can be reduced to a longer period, keeping the duty cycle between about 10% and about 50%, once habituation occurred in this parameter.

It should be noted that the current amplitude of a stimulation signal may also vary depending on the type of energy delivery module (such as an electrode) used. A helical electrode that has intimate contact with the nerve will have a lower amplitude than a cylindrical electrode that may reside millimeters away from the nerve. In general, the current amplitude used to cause stimulation is proportional to $1/(\text{Radial Distance From Nerve})^2$. The pulse width can remain constant or can be increased to compensate for the greater distance. The stimulation intensity would be adjusted to activate the afferent/efferent B or C fibers depending on the electrodes used. Using the muscle twitching threshold prior to habituation can help guide therapy, given the variability of contact/distance between the nerve and electrode.

Weight loss induced by electrical activation of the splanchnic nerve may be amplified by providing dynamic nerve modulation or stimulation. Dynamic stimulation refers to changing the values of stimulation signal intensity, stimulation frequency and/or the duty cycle parameters during treatment. The stimulation intensity, stimulation frequency and/or duty cycle parameters may be changed independently, or they may be changed in concert. One parameter may be changed, leaving the others constant; or multiple parameters may be changed approximately concurrently. The stimulation intensity, stimulation frequency and/or duty cycle parameters may be changed at regular intervals, or they may be ramped up or down substantially continuously. The stimulation intensity, stimulation frequency and/or duty cycle parameters may be changed to preset values, or they may be changed to randomly generated values. In some embodiments, the changes in the stimulation signal parameters are altered through an automated process, for example, a programmable pulse generator. When random changes in the stimulation signal parameter or parameters are desired, those changes may be generated randomly by a pulse generator. One advantage of dynamic stimulation is that the patient's body is unable, or at least less able, to adapt or compensate to the changing simulation than to a constant or regular pattern of stimulation.

Weight loss induced by electrical activation of the splanchnic nerve may be improved by providing intermittent therapy, or intervals of electrical stimulation followed by intervals of no stimulation. Data shows that after an interval of stimulation, weight loss can be accelerated by turning the stimulation signal off. This is directly counter to the notion that termination of therapy would result in a rebound phenomenon of increased food intake and weight gain. This data also indicates that a dynamic, or changing, stimulation intensity (e.g., increasing or decreasing daily) produces a more pronounced weight loss than stimulation at a constant intensity. This intermittent therapy, coupled with a dynamic or changing stimulation intensity, is called the ramp-cycling technique, and ramp cycling is one subset of the dynamic stimulation techniques described herein. Given these findings, several dosing strategy embodiments are described below.

These treatment algorithm embodiments are derived from studies involving canines. The muscle twitch threshold using a helical electrode is determined after adequate healing time post implant has elapsed which is typically about 2 to about 6 weeks. In certain embodiments, this threshold may range from about 0.125 mA-msec to about 0.5 mA-msec. The stimulation intensity is increased daily over about 1 to about 2 weeks, allowing some or complete habituation of muscle twitching to occur between successive increases, until an intensity of about 8 times to about 10 times the signal intensity of the muscle twitch threshold is achieved, for example about 1.0 mA-msec to about 5.0 mA-msec. In certain embodiments, the stimulation intensity and/or the stimulation frequency is increased until an intensity of about 2 times the signal intensity of the muscle twitch threshold is achieved. In certain embodiments, the stimulation intensity is increased until an intensity of about 4 times the signal intensity of the muscle twitch threshold is achieved. In certain embodiments, the stimulation intensity is increased until an intensity of about 6 times the signal intensity of the muscle twitch threshold is achieved. During this period, a rapid decline in body weight and food intake is generally observed.

After the initial weight loss period, a transition period is observed over about 1 to about 4 weeks in which some lost weight may be regained. Subsequently, a sustained, gradual reduction in weight and food intake occurs during a prolonged stimulation phase of about 4 weeks to about 8 weeks. After this period of sustained weight loss, the stimulation may be terminated, which is again followed by a steep decline in weight and food intake, similar to the initial stimulation intensity ramping phase. The post-stimulation weight and food decline may last for about 1 week to about 4 weeks, after which the treatment algorithm may be repeated to create a therapy cycle, or intermittent treatment interval, that results in sustained weight loss. The duty cycle during this intermittent therapy may range from about 20% to about 50% with stimulation on-times of up to about 15 seconds to about 60 seconds. This intermittent therapy not only increases the weight loss effectiveness, but also extends the battery life of an implanted device or reduces energy consumption for a non-implanted pulse generator.

In another intermittent therapy treatment algorithm embodiment, therapy cycling occurs during about a 24 hour period. In this algorithm, the stimulation signal intensity is maintained at about 1 times to about 3 times the muscle twitch threshold for a period of about 12 hours to about 18 hours. In certain embodiments, the stimulation signal intensity may be increased gradually (e.g., each hour) during a first stimulation interval. In certain embodiments, the stimulation signal intensity may be increased at other intervals during a first stimulation interval. The stimulation is subsequently terminated or reduced to a subthreshold level for about 6 hours to about 12 hours. In certain embodiments, the stimulation signal intensity may be gradually decreased during a second interval back to a signal intensity substantially at the muscle twitch threshold level. Due to this sustained or accelerating effect that occurs even after cessation of stimulation, the risk of binge eating and weight gain during the off period or declining stimulation intensity period is minimized.

Figure 5:
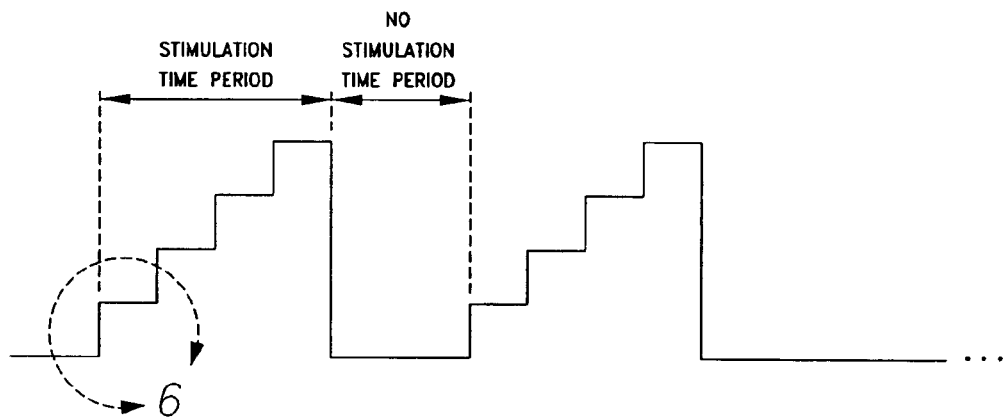
FIG. 5 is a schematic diagram of an exemplary ramp-cycling treatment algorithm.
Figure 6:
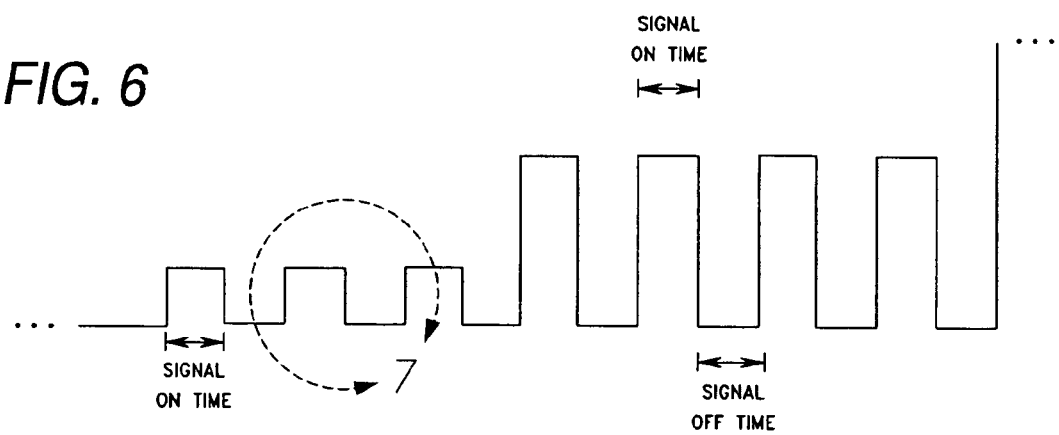
FIG. 6 shows a portion of the ramp-cycling treatment algorithm of FIG. 5 in more detail.
Figure 7:
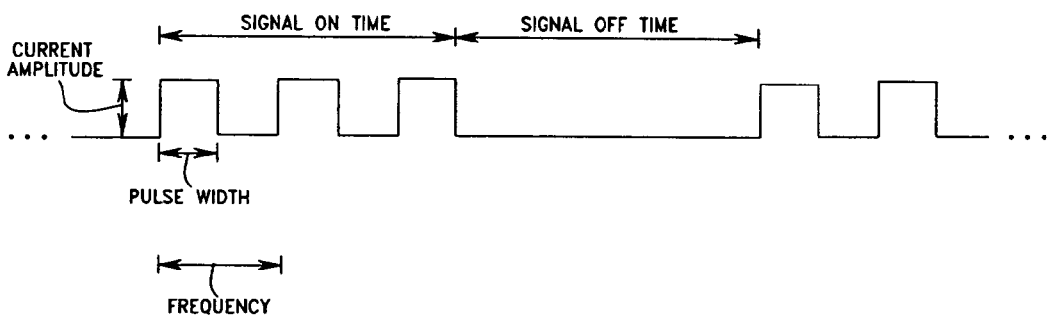
FIG. 7 shows a more detailed view of a portion of the exemplary stimulation pattern of FIG. 6.

Certain embodiments utilize the ramp-cycling therapy or the ramp-cycling technique. One embodiment of the ramp-cycling technique is shown schematically in FIGS. 5-7. FIG. 5 has a longer time scale than FIG. 6, which in turn has a longer time scale than FIG. 7. FIG. 5 shows the main features of one embodiment of the ramp-cycling technique. Each period of the cycle includes a stimulation time period (or stimulation period) and a no-stimulation time period (or no-stimulation period). The stimulation time period may be referred to as a first time period, an interval of electrical stimulation, an interval of stimulation, a stimulation intensity ramping phase, or a stimulation interval. In certain embodiments, the stimulation time period may include on-times, off-times, suprathreshold periods, and subthreshold periods. The no-stimulation time period may be referred to as a second time period, an interval in which the device is off or delivering low power, an interval of no stimulation, or a declining stimulation intensity period. In certain embodiments, the no-stimulation time period may include one or more subthreshold periods. The stimulation time period and no-stimulation time period should not be confused with the stimulation on-time, signal on-time (or on-period or on-time), or the signal off-time (or off-period or off-time) which are terms describing the parameters of the duty cycle and shown in FIGS. 6 and 7. The stimulation time period further comprises portions or consecutive intervals.

In some embodiments of the ramp-cycling version of intermittent therapy, the stimulation time period comprises at least two portions having different stimulation intensities. The portions may also be referred to as consecutive intervals. In certain embodiments, the stimulation intensity of each portion may be greater than the stimulation intensity of the previous portion. The multiple portions of such an embodiment are represented by the stimulation time period's step-like structure as shown in the embodiment in FIG. 5. In certain embodiments, the increase in stimulation intensity is approximately continuous over the entire stimulation time period, rather than increasing in a stepwise manner. In some embodiments, the stimulation intensity during the no-stimulation time period is about zero (e.g. the pulse generator is inactive) as is shown in FIG. 5. In certain embodiments, the stimulation intensity during the no-stimulation time period is substantially reduced from the maximum stimulation intensity applied during the stimulation time period. In certain embodiments, the stimulation intensity during the no-stimulation period is ramped down through at least two portions of the no-stimulation period. In certain embodiments, a decrease in stimulation intensity, if any, is approximately continuous over the entire no-stimulation time period, rather than decreasing in single or multiple steps.

A single cycle of ramp-cycling therapy includes a stimulation time period and a no-stimulation time period. In some embodiments of the ramp-cycling technique, a single cycle may be repeated without changing any of the treatment parameters, the duty cycle parameters or the signal parameters of the original cycle. In certain embodiments the treatment parameters, and/or the duty cycle parameters and/or the signal parameters may be changed from cycle to cycle. In certain embodiments, a single cycle of ramp-cycling therapy comprises one to many suprathreshold periods and subthreshold periods.

Setting the stimulation signal parameters to particular values may inhibit substantial regain of lost weight for a relatively long time following the stimulation period. Indeed, weight and food intake may even continue to decline during the no-stimulation period, in which the stimulator is turned off. If the stimulation intensity is increased daily by about 20% over a period of several weeks until it is equal to about 8 times to about 10 times the signal intensity of muscle twitch threshold, and if the stimulator is subsequently turned off, then there is a period of about several days thereafter in which there is no rebound increase in weight or food intake.

In certain intermittent therapy treatment algorithm embodiments, ramp-cycling therapy occurs during a period of about ten days to about two months. In this algorithm, the stimulation intensity during one portion of the stimulation time period is initiated and maintained at the muscle twitch threshold for about 24 hours. The stimulation intensity (current (mA) multiplied by pulse width (msec)) is increased by about 20% each day thereafter (i.e. during each subsequent portion of the simulation time period) until the stimulation intensity is about 8 times to about 10 times the muscle twitch threshold. After about 24 hours of stimulation at about 8 times to about 10 times the muscle twitch threshold, the stimulator is turned off during the no-stimulation time period of between about one-half day to about seven days. Utilizing a stimulation period of about 24 hours permits habituation of the muscle twitch, which reduces the discomfort experienced by the subject. Turning the stimulator off during the no stimulation time period on the order of days avoids a sustained increase in the MAP, reduces the likelihood that the subject develops a tolerance to the therapy, and preserves the stimulator's battery life.

In certain embodiments, a stimulation intensity increase of about 20% from one portion of the stimulation on period to the next portion is achieved by increasing the pulse width by about 20%. In certain embodiments, the stimulation intensity increase of about 20% is achieved by changing both the current and pulse width such that the product of the new values is about 20% greater that the product of the previous day's values for those parameters. In certain embodiments, the stimulation intensity increase of about 20% is achieved by increasing both the current and pulse width such that the product of the new values is about 20% greater that the product of the previous day's values for those parameters. In certain embodiments, the stimulation intensity increase of about 20% is achieved by increasing the current amplitude of the stimulation signal by about 20%.

In certain embodiments, the stimulation intensity increase of about 20% in a 24-hour period is achieved by an approximately continuous change in either the current amplitude, pulse width, or both. In certain embodiments, the stimulation signal intensity increase of about 20% in a 24 hour period is achieved by changing the current amplitude, pulse width, or both, at irregular intervals within each 24-hour period. In certain embodiments, the stimulation signal intensity increase of about 20% in a 24-hour period is achieved by changing the current amplitude, pulse width, or both, at regular intervals within each 24-hour period. In certain embodiments, the stimulation intensity increase of about 20% in a 24-hour period is achieved by changing the current amplitude, pulse width, or both, at regular intervals and in a stepwise manner within each 24-hour period. In certain embodiments, stimulation intensity increase of about 20% in a 24 hour period is achieved by changing the current amplitude, pulse width, or both, once during each 24-hour period. In certain embodiments, the stimulation intensity increase of about 20% in a 24 hour period is achieved by increasing the current amplitude once during each 24 hour period.

In certain embodiments, the stimulator is turned off in the cycle for between about 1 day and about 10 days. In certain embodiments, the stimulator is turned off for between about 1 day and about 5 days. In certain embodiments, the stimulator is turned off for about 3 days.

Certain embodiments include a method for treating a medical condition, the method comprising electrically activating a splanchnic nerve in a mammal for the stimulation time period, wherein the first time period comprises a plurality of consecutive intervals. During each of the plurality of consecutive intervals, the splanchnic nerve in the mammal is electrically activated according a stimulation pattern configured to result in net weight loss in the mammal during each interval. The stimulation pattern includes a signal on-time (on period or on-time) and a signal-off time (off period or off time) in a duty cycle. The on period includes a stimulation intensity and a frequency. In certain embodiments, the on period includes a suprathreshold period and a subthreshold period. The stimulation intensity includes a current amplitude and a pulse width. The method further includes reducing or ceasing the electrical activation of the splanchnic nerve for a no-stimulation time period, such that the mammal loses net weight during the no-stimulation period. In certain embodiments, the no-stimulation time period includes a subthreshold period.

In one embodiment, the duration of the stimulation time period is about ten days. In certain embodiments the duration of the stimulation time period is about 1 day to about 50 days. In certain embodiments the duration of the stimulation time period is about 4 hours to about 100 days. In some embodiments, there are ten consecutive intervals in the stimulation time period. In certain embodiments, there are about 3 intervals to about 50 intervals in the stimulation time period. In certain embodiments there are about 2 intervals to about 5000 intervals in the stimulation time period. In some embodiments, the duration of each consecutive interval is about 24 hours. In certain embodiments, the duration of each consecutive interval is about 12 hours to about 7 days. In certain embodiments, each consecutive interval is 1 minute to about 50 days.

In one embodiment, the duration of the on period is approximately equal to the duration of the interval, and the duration of the off period is approximately zero seconds. In some embodiments, the ratio of the on period to the off period is about 0.75 to about 1.5. In certain embodiments, the ratio is greater than about 0.75. In some embodiments, the ratio is greater than about 1.5. In certain embodiments, the ratio of the on period to the off period is greater than about 3. In certain embodiments, the ratio of the on period to the off period is about 0.75 or less, while in certain embodiments the ratio is about 0.5 or less. In certain embodiments, the ratio of the on period to the off period is about 0.3 or less. In certain embodiments, the on period is about two minutes or less. In some embodiments, the on period is about one minute or less. In certain embodiments, the on period is about one minute or less, and the off period is about one minute or more. In some embodiments the on period is greater than about 15 seconds but in certain embodiments, the on-time is greater than about 30 seconds.

In one embodiment, the duration of the suprathreshold period is approximately equal to the duration of the interval, and the duration of the subthreshold period is approximately zero seconds. In some embodiments, the ratio of the suprathreshold period to the subthreshold period is about 0.75 to about 1.5. In certain embodiments, the ratio is greater than about 0.75. In some embodiments, the ratio is greater than about 1.5. In certain embodiments, the ratio of the suprathreshold period to the subthreshold period is greater than about 3. In certain embodiments, the ratio of the suprathreshold period to the subthreshold period is about 0.75 or less, while in certain embodiments the ratio is about 0.5 or less. In certain embodiments, the ratio of the suprathreshold period to the subthreshold period is about 0.3 or less. In certain embodiments, the suprathreshold period is about two minutes or less. In some embodiments, the suprathreshold period is about one minute or less. In certain embodiments, the suprathreshold period is about one minute or less, and the subthreshold period is about one minute or more. In some embodiments the suprathreshold period is greater than about 15 seconds but in certain embodiments, the on-time is greater than about 30 seconds.

In some embodiments the combined on period and off period cycle is repeated continuously within the interval. In certain embodiments the combined on period and off period cycle is repeated intermittently within the interval. In certain embodiments, the combined on period and off period cycle is repeated irregularly within the interval. In some embodiments the combined suprathreshold period and subthreshold period cycle is repeated continuously within the interval. In certain embodiments the combined suprathreshold period and subthreshold period cycle is repeated intermittently within the interval. In certain embodiments, the combined suprathreshold period and subthreshold period cycle is repeated irregularly within the interval. In some embodiments, the frequency of the stimulation signal is about 15 Hz or greater to minimize skeletal twitching. In some embodiments the frequency of the stimulation signal is about 20 Hz or greater. In some embodiments the frequency of the stimulation signal is about 30 Hz or greater. In some embodiments, the frequency is varied within each interval, but in certain embodiments the frequency remains constant within each interval. In some embodiments the frequency is varied from interval to interval, but in certain embodiments the frequency remains constant.

In some embodiments the stimulation intensity of the signal is varied within each interval during the stimulation time period, but in certain embodiments, the stimulation intensity remains constant within each interval during the stimulation time period. In some embodiments the stimulation intensity is varied from interval to interval during the stimulation time period. In some embodiments the stimulation signal intensity is increased from interval to interval during the stimulation time period. In some embodiments the stimulation intensity of the first interval during the stimulation time period is set at about the muscle twitch threshold. In some embodiments the first interval is set below the muscle twitch threshold, while in certain embodiments the first interval is set above the muscle twitch threshold.

In some embodiments the stimulation intensity is increased by about 20% from interval to interval during the stimulation time period. In some embodiments the stimulation intensity is increased by about 15% to about 25% from interval to interval. In certain embodiments, the stimulation intensity is increased by about 1% to about 15% from interval to interval. In certain embodiments, the stimulation intensity is increased by about 25% to about 40% from interval to interval. In certain embodiments the stimulation intensity is increased by about 40% to about 100% from interval to interval.

In some embodiments the stimulation signal intensity is varied by changing the current amplitude. In some embodiments the stimulation intensity is varied by changing the pulse width. In some embodiments, the stimulation signal intensity is varied by changing the electrical potential. In some embodiments the stimulation intensity is varied by changing any combination of the current amplitude, the pulse width, and the electrical potential or voltage.

In some embodiments the no-stimulation time period is about 4 days. In some embodiments the no-stimulation time period is about 1 day to about 7 days. In some embodiments the no-stimulation time period is about 18 hours to about 10 days. In some embodiments the no-stimulation time period is about 1 hour to about 50 days. In some embodiments the no-stimulation time period is more than about 50 days. In some embodiments the no-stimulation time period is less than about 1 day. In some embodiments the no-stimulation time period is less than about 6 hours. In certain embodiments, the second time period is less than about 1 hour.

The following three ramp-cycling algorithm embodiments were tested for their efficacy. Each experiment lasted for 28 days. The first algorithm used daily, stepwise increases in the current amplitude of the stimulation signal to increase the stimulation intensity during the stimulation time period. The stimulation intensity was so increased for 9 consecutive days within the stimulation time period. On the 10th day, the no-stimulation time period began. During the no stimulation time period the stimulator was turned off and remained off for 4 days. The above cycle was then repeated.

The second of the three ramp-cycling algorithms used daily, stepwise increases in the current amplitude to increase the stimulation intensity during the stimulation time period. The stimulation intensity was so increased for 9 consecutive days. On the 10th day, the no-stimulation time period began. During the no-stimulation time period the stimulator was turned off and remained off for 3 days. That cycle was then repeated.

The third of the three ramp-cycling algorithms used daily, stepwise increases in the current amplitude to increase the stimulation intensity during the stimulation time period. The stimulation intensity was so increased for 9 consecutive days. On the 10th day, the no-stimulation time period began. In this case, the stimulation intensity was reduced to a non-zero threshold value during the no-stimulation time period. The cycle was then repeated. This algorithm did not contain a no-stimulation time period where the stimulator was turned off.

Figure 8:
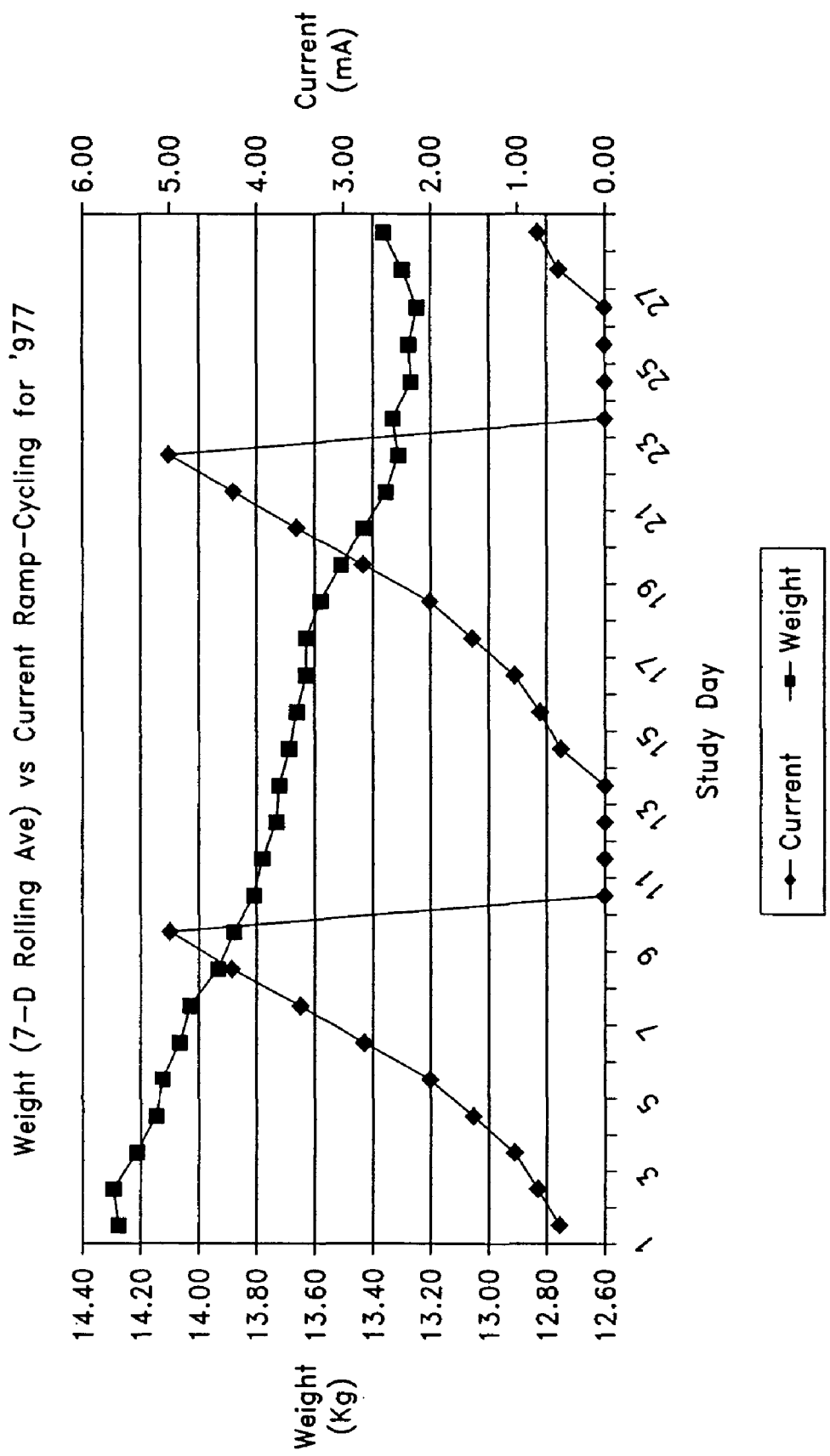
FIG. 8 shows the weight (as a seven-day rolling average) and the current amplitude for canine subject '977 over the course of its 28-day, ramp-cycling therapy.
Figure 9:
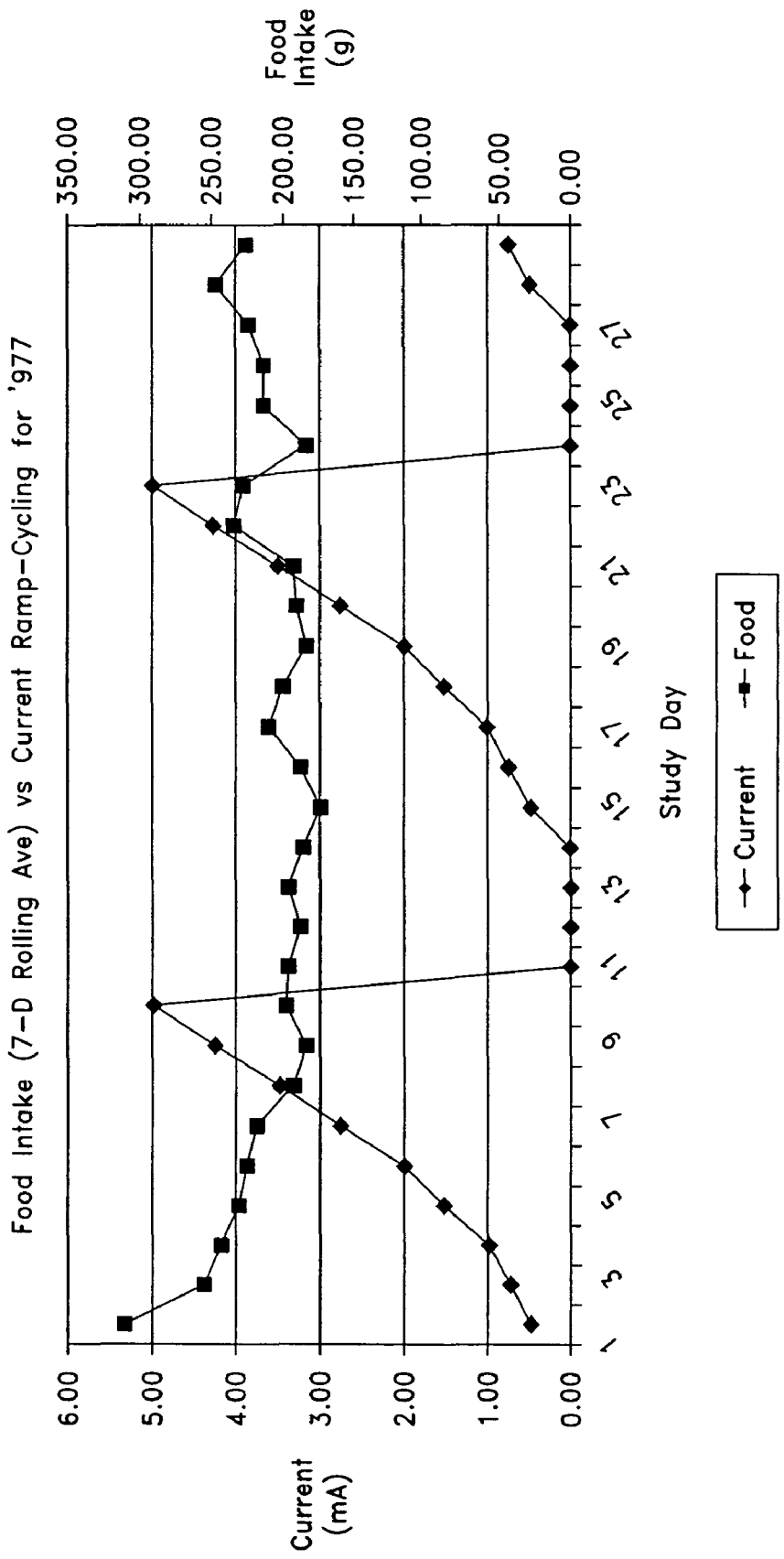
FIG. 9 shows the food intake (as a seven-day rolling average) and the current amplitude for canine subject '977 over the course of its 28-day, ramp-cycling therapy.
Figure 10:
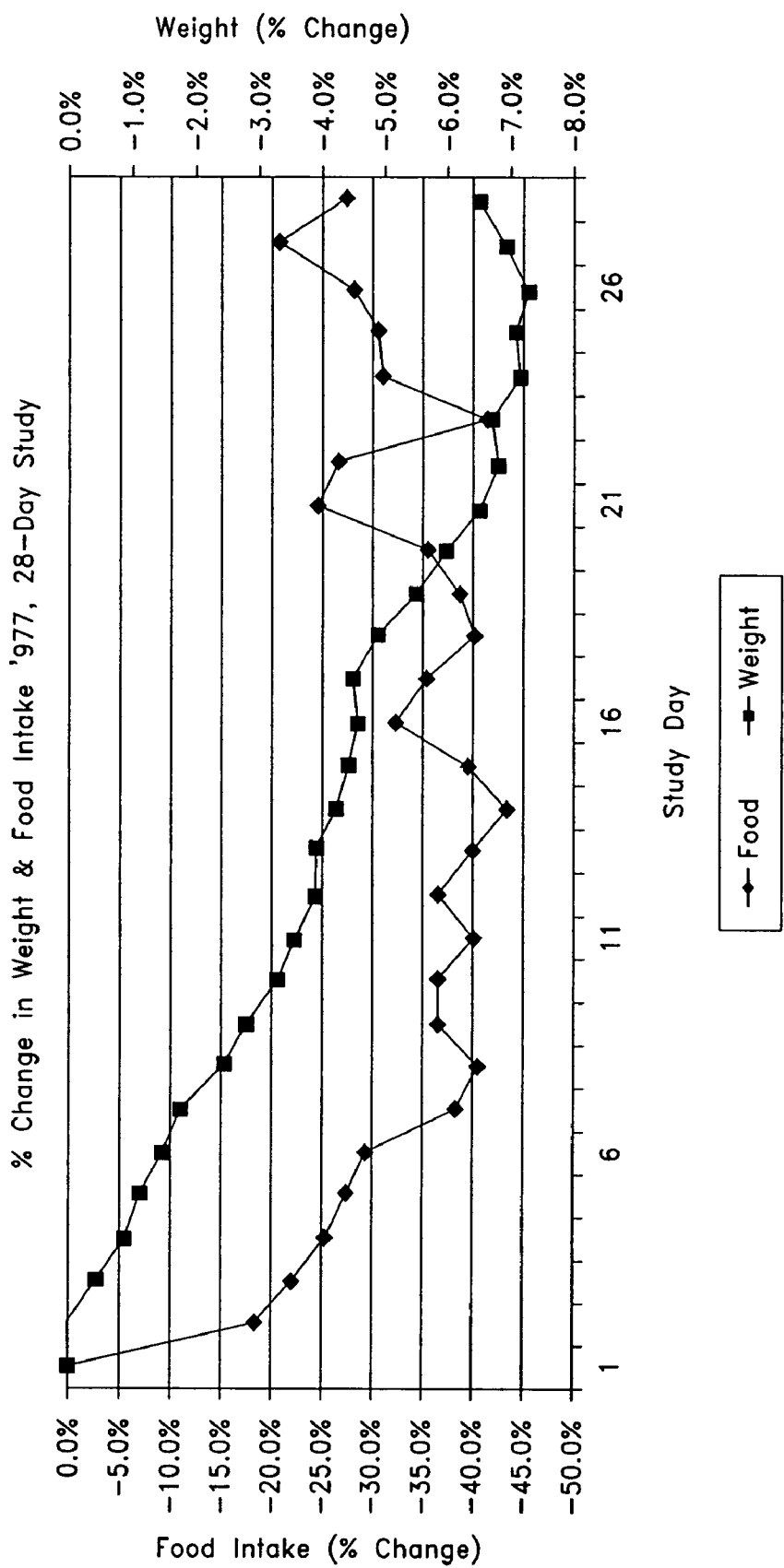
FIG. 10 shows the percent change (relative to day one) in weight and food intake for canine subject '977 over the course of its 28-day, ramp-cycling therapy.

The results of some ramp-cycling algorithm embodiments are given in FIGS. 8-10. FIG. 8 shows the current amplitude and weight (calculated as a seven day rolling average) plotted against time in days for the dog in the 28-day study utilizing a first ramp-cycling algorithm. The data show that the animal's weight continued to decrease during the four-day period (the no-stimulation period) in which the stimulator was turned off. FIG. 9 shows the current amplitude and food intake (calculated as a seven day rolling average) plotted against time in days for the same dog. The data show that the animal's food intake decreased during the stimulation time period and showed only a modest upward trend during the four days during the no-stimulation time period in which the stimulator was turned off. FIG. 10 shows the percent change in weight and food intake as a function of time in days. These data reflect the net change in the magnitude of the parameter referenced to the value on the first day. These values are not calculated as a rolling average. The data demonstrate the general trend of weight decrease even over the four-day no-stimulation time period in which the stimulator was inactive. The data also exhibit a significant reduction in food intake over the initial cycle followed by an approximately constant and modest increase thereafter.

Figure 11:
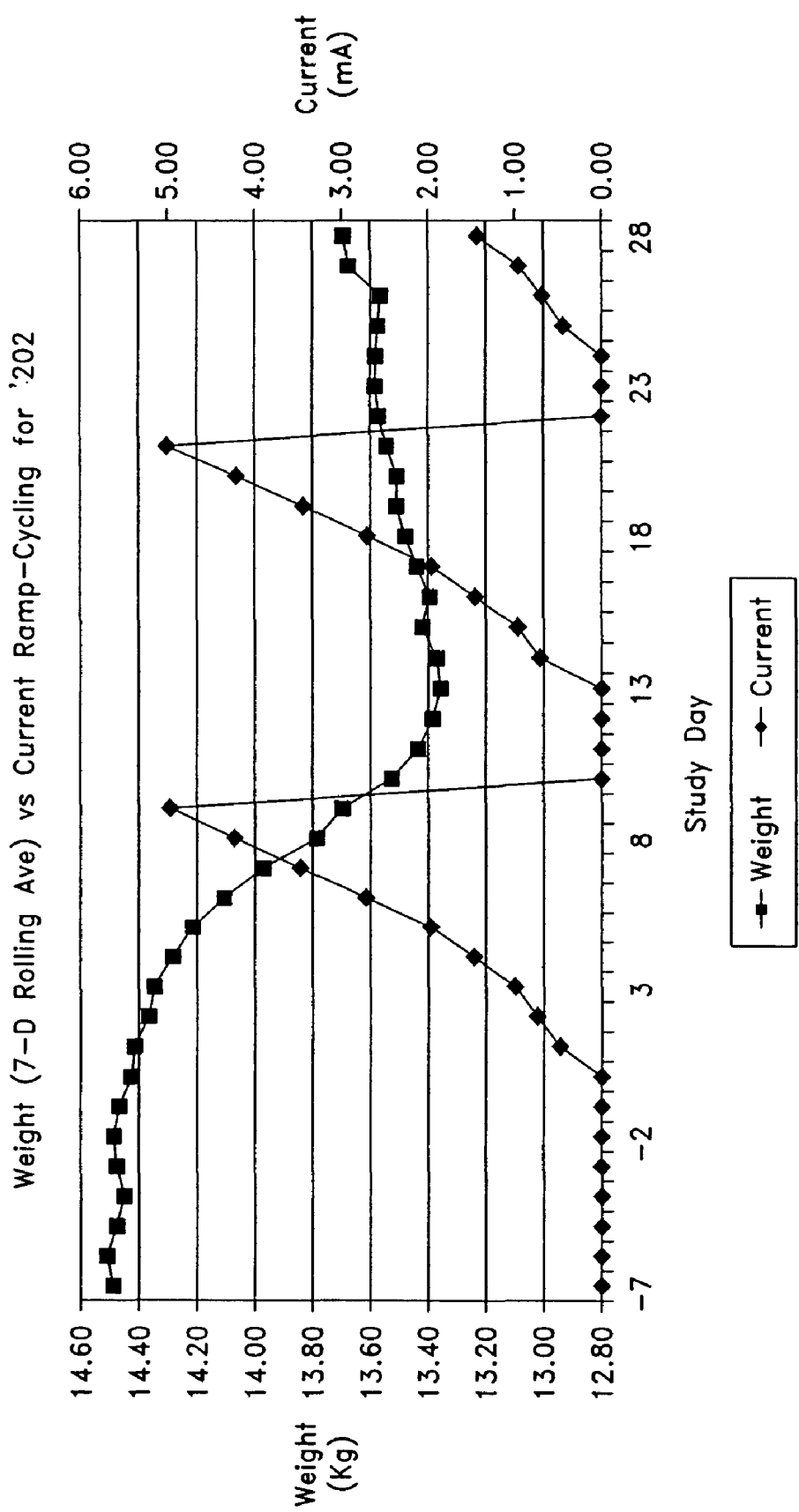
FIG. 11 shows the weight (as a seven-day rolling average) and the current amplitude for canine subject '202 over the course of its 28-day, ramp-cycling therapy.
Figure 12:
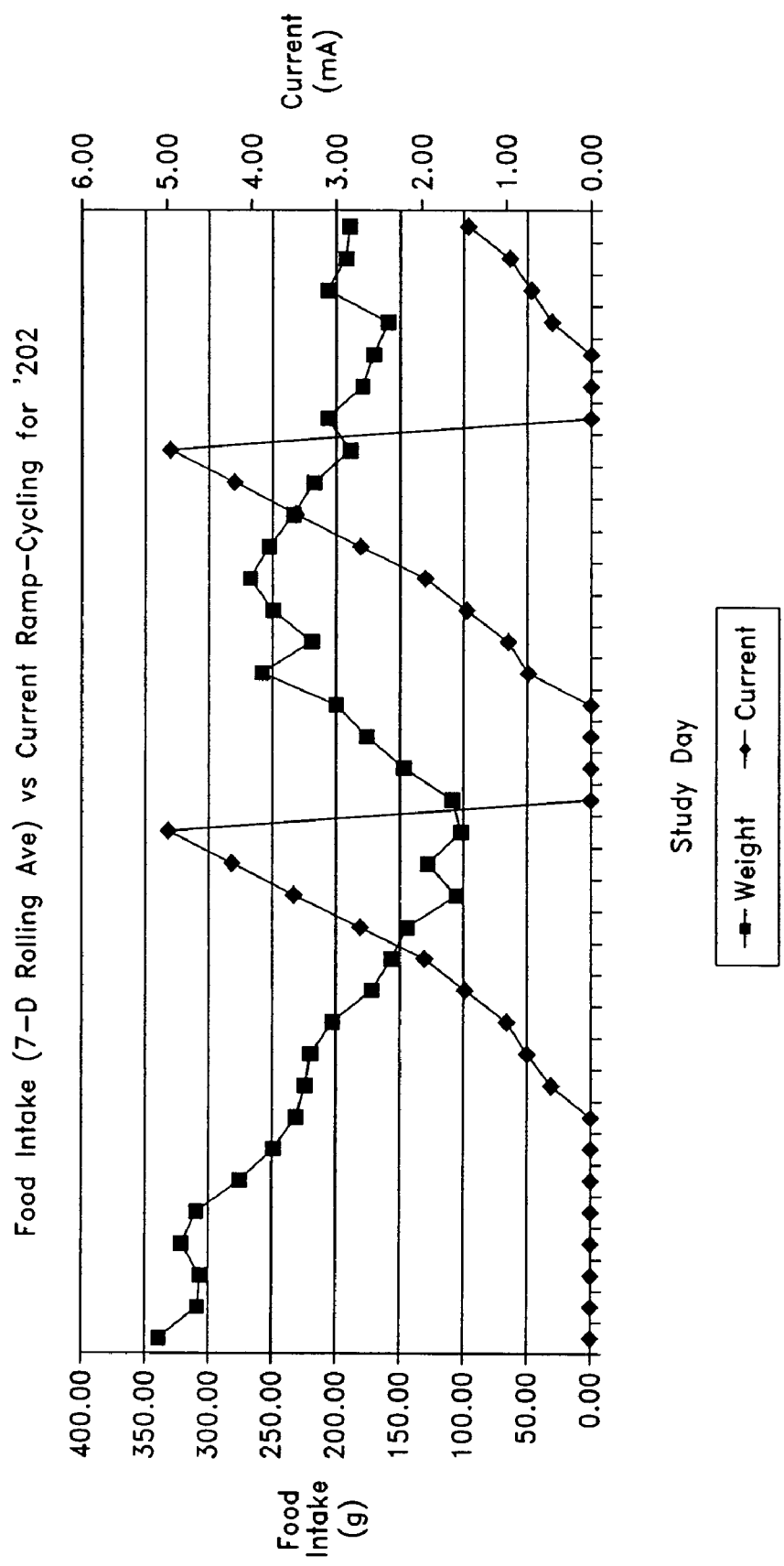
FIG. 12 shows the food intake (as a seven-day rolling average) and the current amplitude for canine subject '202 over the course of its 28-day, ramp-cycling therapy.
Figure 13:
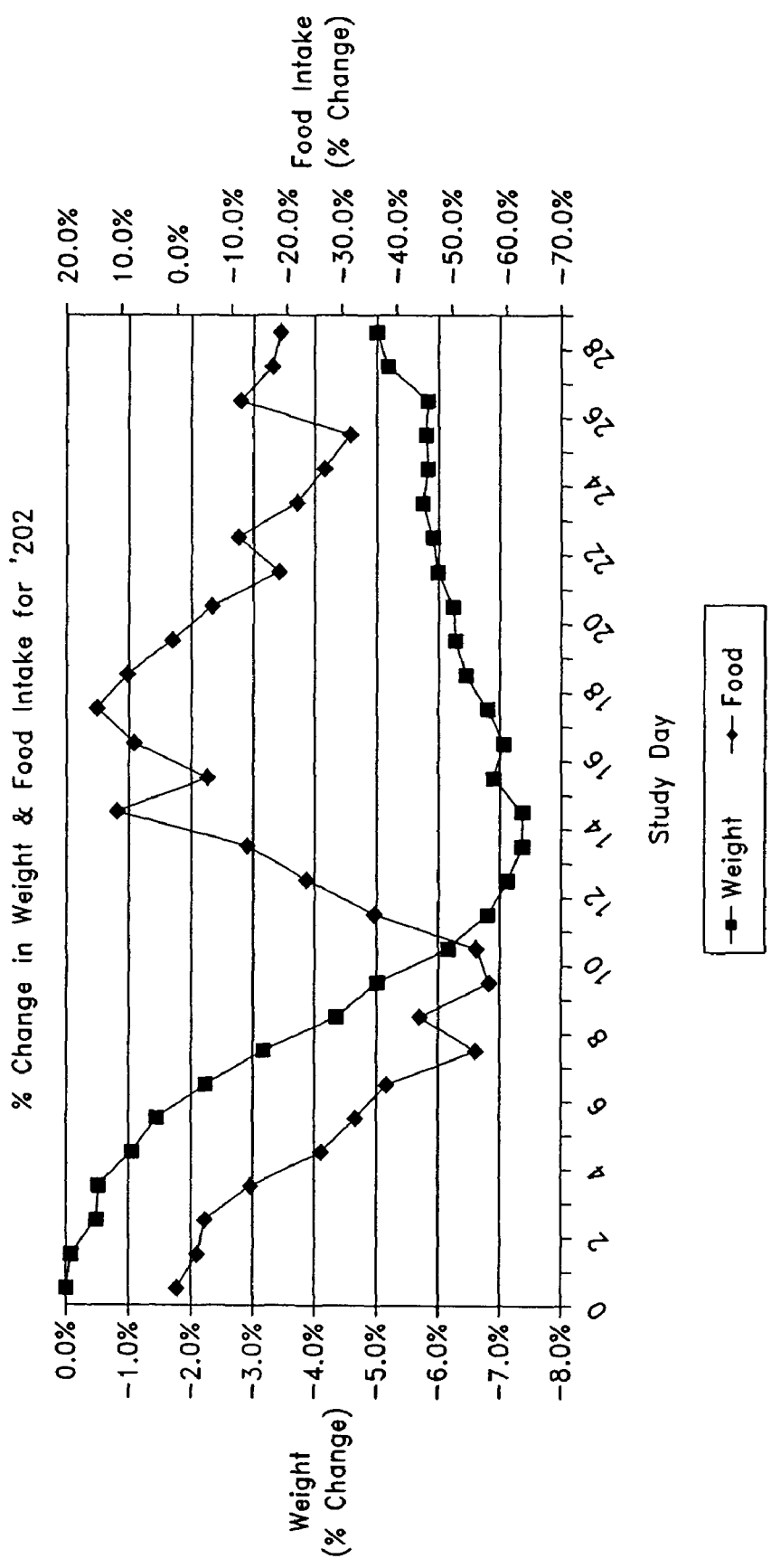
FIG. 13 shows the percent change (relative to day one) in weight and food intake for canine subject '202 over the course of its 28-day, ramp-cycling therapy.

The results of other ramp-cycling algorithm embodiments are given in FIGS. 11-13. FIG. 11 shows the current amplitude and weight (calculated as a seven day rolling average) plotted against time in days for a different dog in a 28-day study. The data shows that the animal's weight decreased during the stimulation time period, and showed only a modest increase, if any, during the three-day no-stimulation time period in which the stimulator was turned off. FIG. 12 shows the current amplitude and food intake (calculated as a seven day rolling average) plotted against time in days for the same dog. The data show that the animal's food intake decreased during the stimulation time period but exhibited an upward trend during the three-day no-stimulation time period in which the stimulator was turned off. Even though the food intake partially rebounded, the animal did not experience a substantial regain of the weight lost. FIG. 13 shows the percent change in weight and food intake as a function of time in days. These data reflect the net change in the magnitude of the parameter referenced to the value on the first day. These values are not calculated as a rolling average. The data demonstrate the initial trend of weight decrease even over the three-day period no-stimulation period in which the stimulator is inactive, followed by modest increase in weight over the subsequent cycles. The data also exhibit an erratic pattern for food intake over the several cycles, although the initial cycle shows the expected continuous reduction in food intake.

Figure 14:
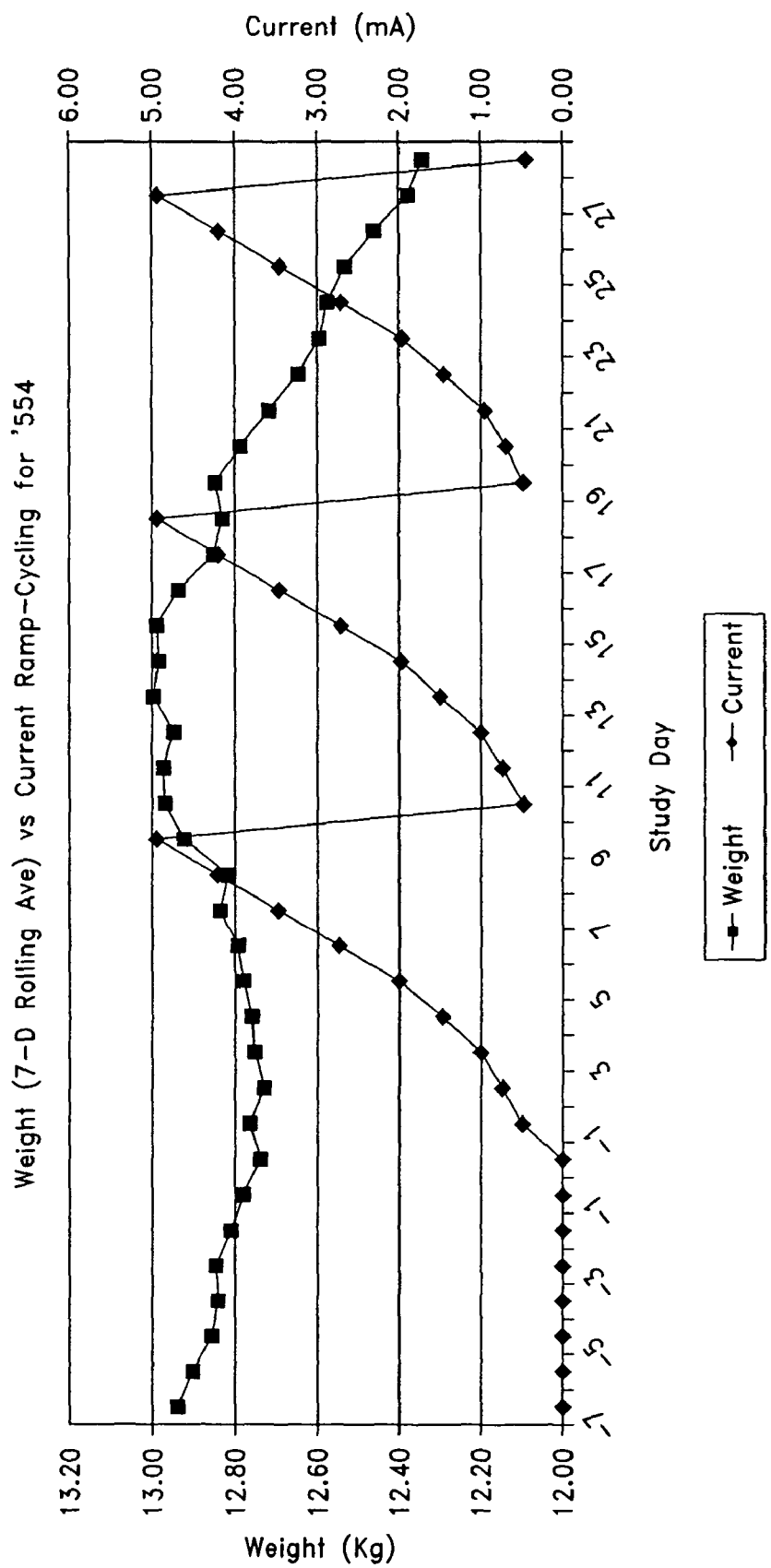
FIG. 14 shows the weight (as a seven-day rolling average) and the current amplitude for canine subject '554 over the course of its 28-day, ramp-cycling therapy.
Figure 15:
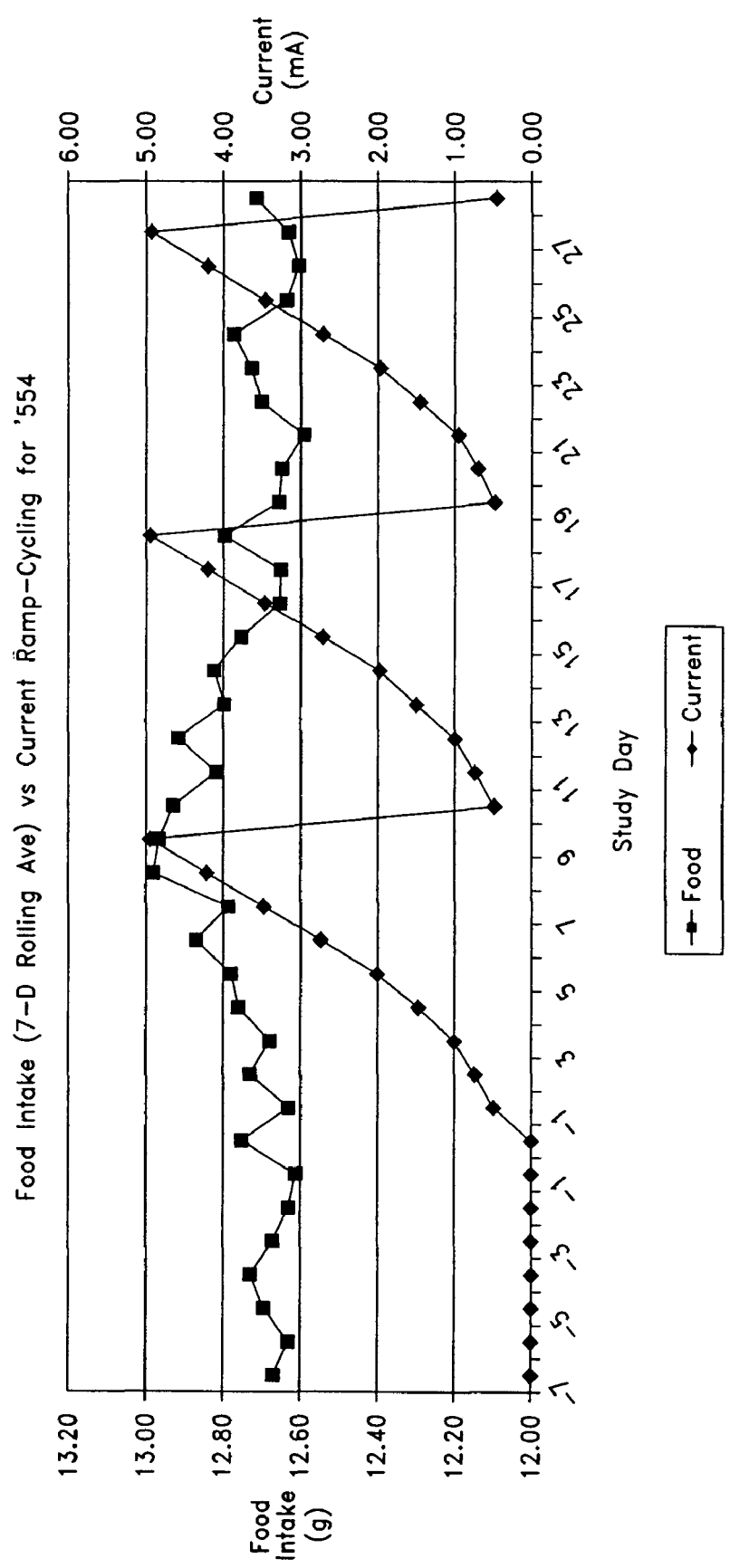
FIG. 15 shows the food intake (as a seven-day rolling average) and the current amplitude for canine subject '554 over the course of its 28-day, ramp-cycling therapy.
Figure 16:
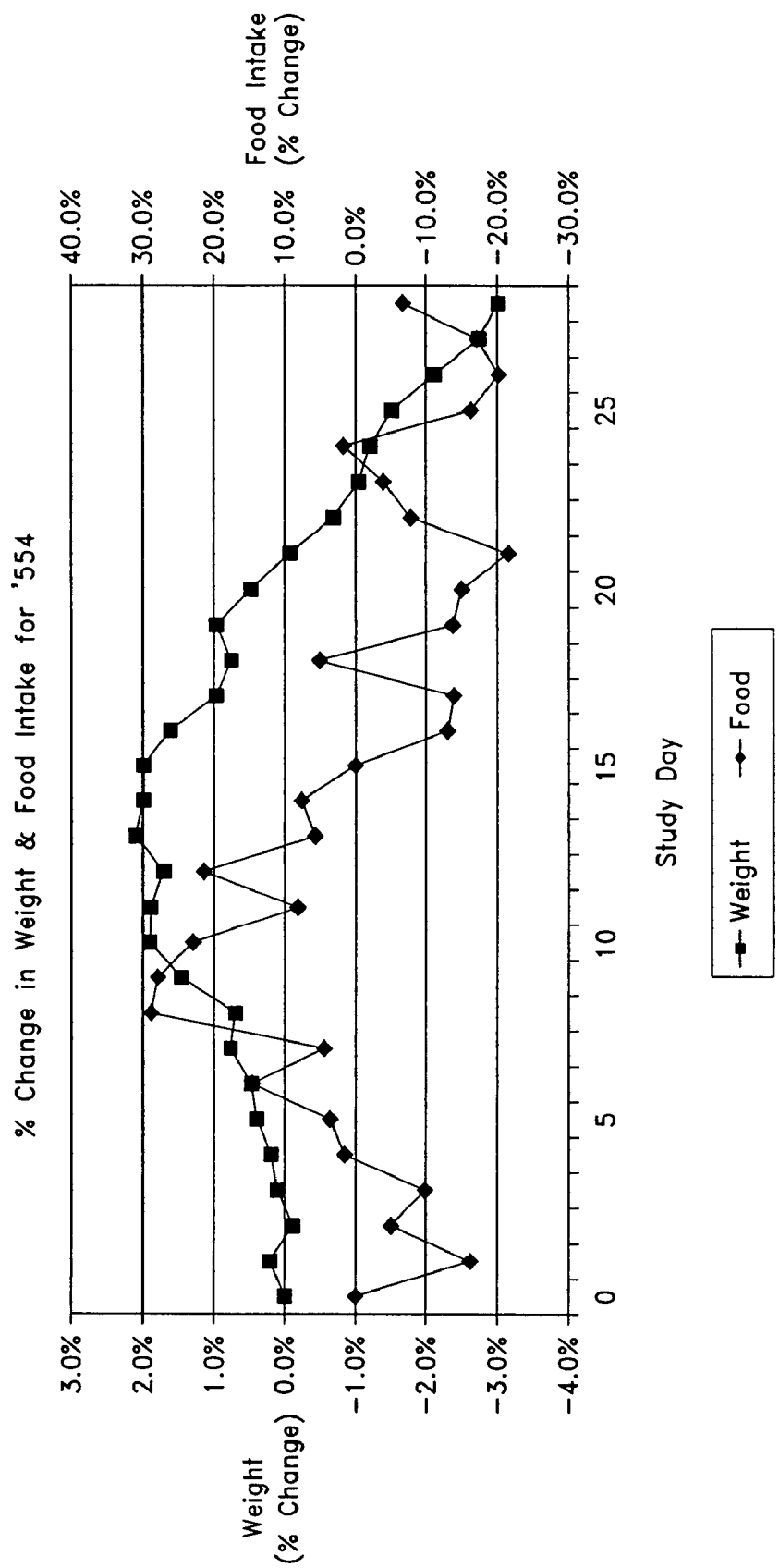
FIG. 16 shows the percent change (relative to day one) in weight and food intake for canine subject '554 over the course of its 28-day, ramp-cycling therapy.

The results of a third ramp-cycling algorithm are given in FIGS. 14-16. FIG. 14 shows the current amplitude and weight (calculated as a seven day rolling average) plotted against time in days for a third dog in a 28-day study. The data shows that the animal's weight decreased over the course of several cycles, although there was a delay in the animal's weight-loss response to the stimulation. In this animal's protocol, the non stimulation time period did not include a time in which the stimulator was completely turned off, rather, the stimulation intensity was reduced to a threshold level during the no-stimulation time period prior to the next ramp-up or stimulation time period. FIG. 15 shows the current amplitude and food intake (calculated as a seven day rolling average) plotted against time in days for the same dog. The animal's food intake showed a modest decrease over the course of the treatment, but it also exhibited a delay in its response. FIG. 16 shows the percent change in weight and food intake as a function of time in days. These data reflect the net change in the magnitude of the parameter referenced to the value on the first day. These values are not calculated as a rolling average. The data demonstrate that, following a delay in responding, there is a net decrease in weight and food intake over time using this algorithm.

Figure 17:
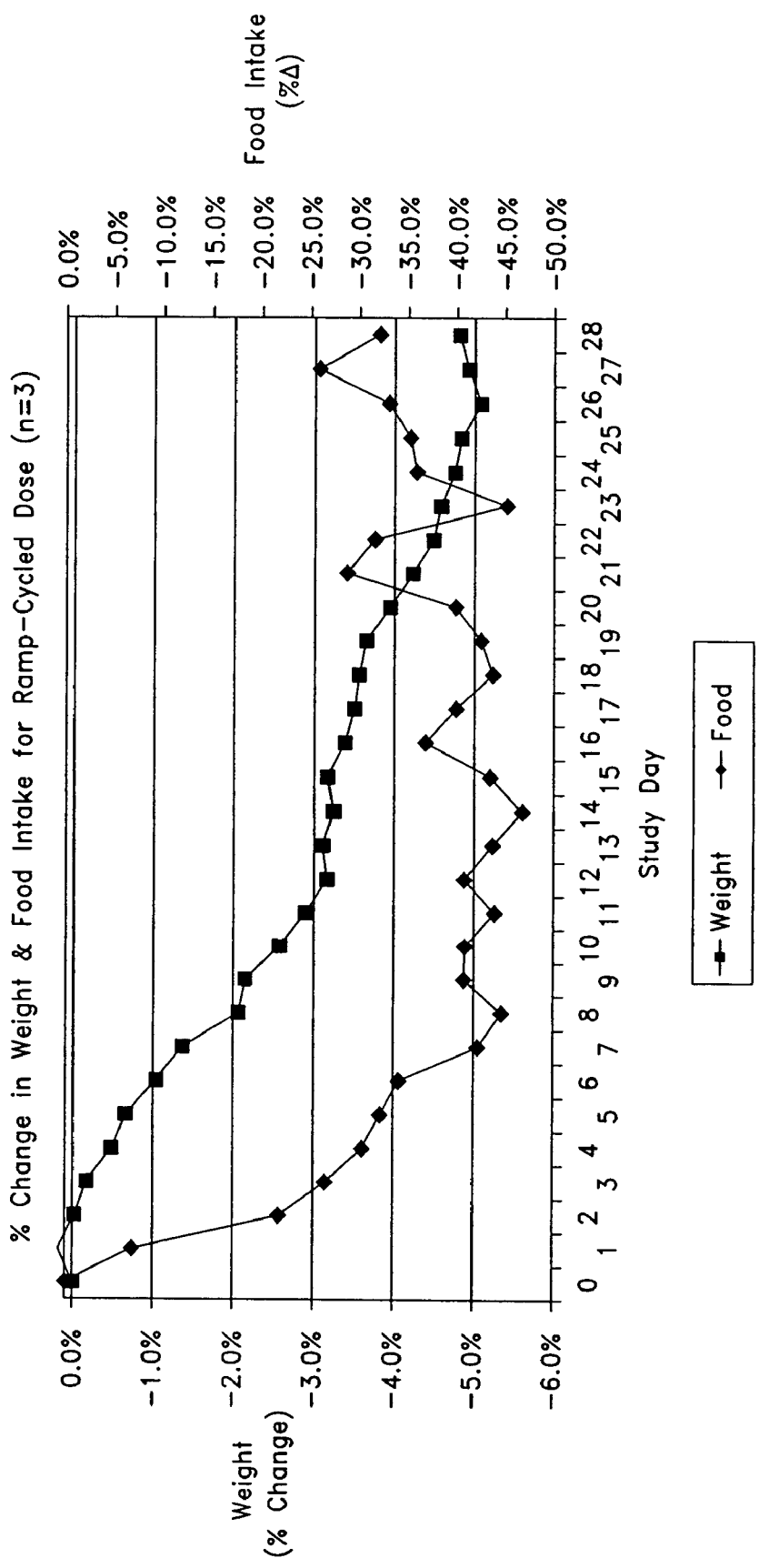
FIG. 17 shows the sum of the percent change (relative to day one) in weight and food intake across the three canine subjects over the course of 28-day, ramp cycling therapy.
Figure 18:
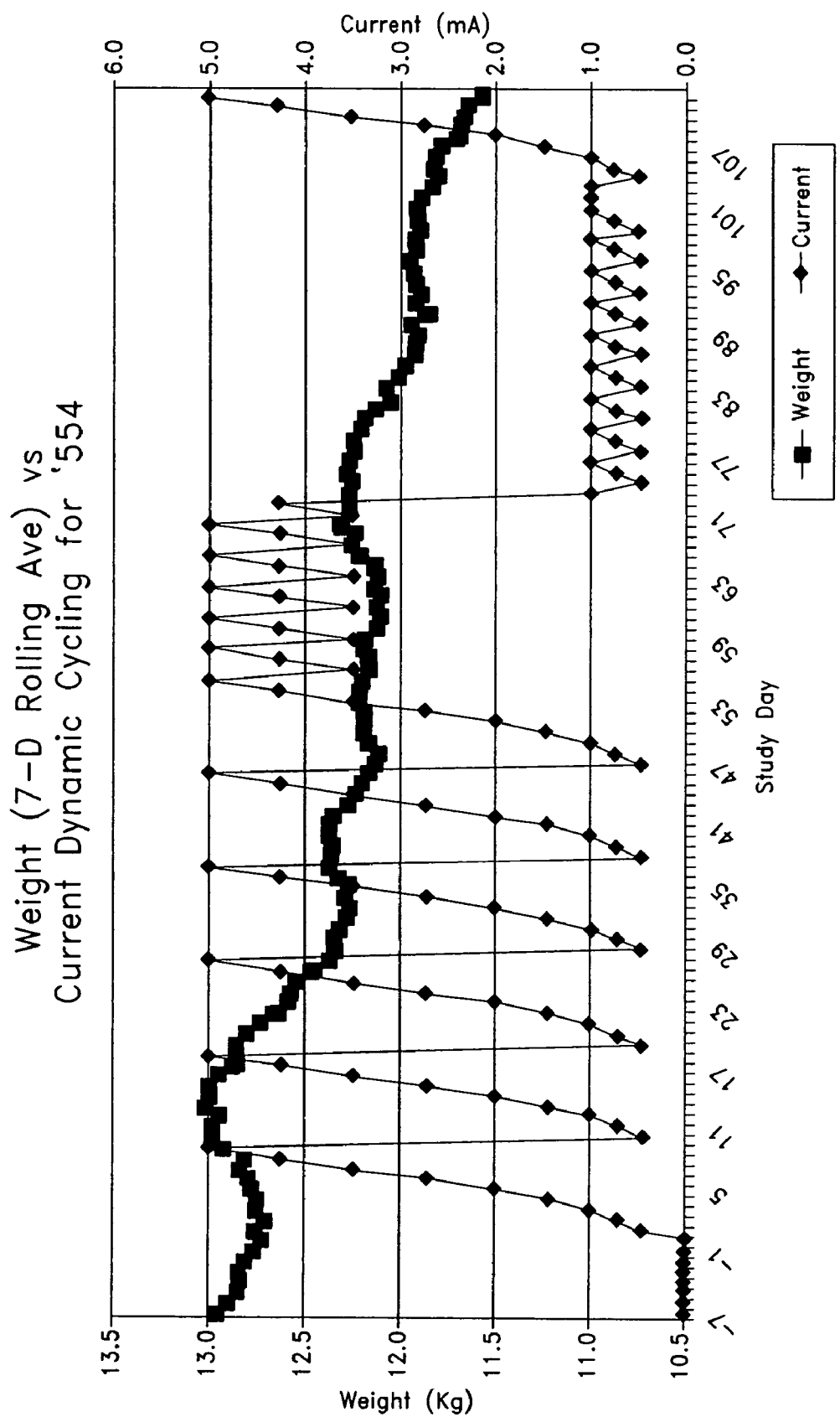
FIG. 18 shows the weight (as a seven-day rolling average) and the current amplitude for canine subject '554, in which both the maximum stimulation intensity, and the level to which the stimulation intensity is decreased, are variable parameters.

FIG. 17 is a plot of the pooled data for the three canine subjects. The graph shows the total percent change in weight and food intake as a function of time in days for the three dogs. This data reflects the net change in the magnitude of the parameter referenced to the value on the first day. These values are not calculated as a rolling average. The data indicates that there is an overall weight decrease using ramp-cycle algorithms, and that there is an initial decrease in food intake followed by a modest rebound after multiple cycles.

Figure 19:
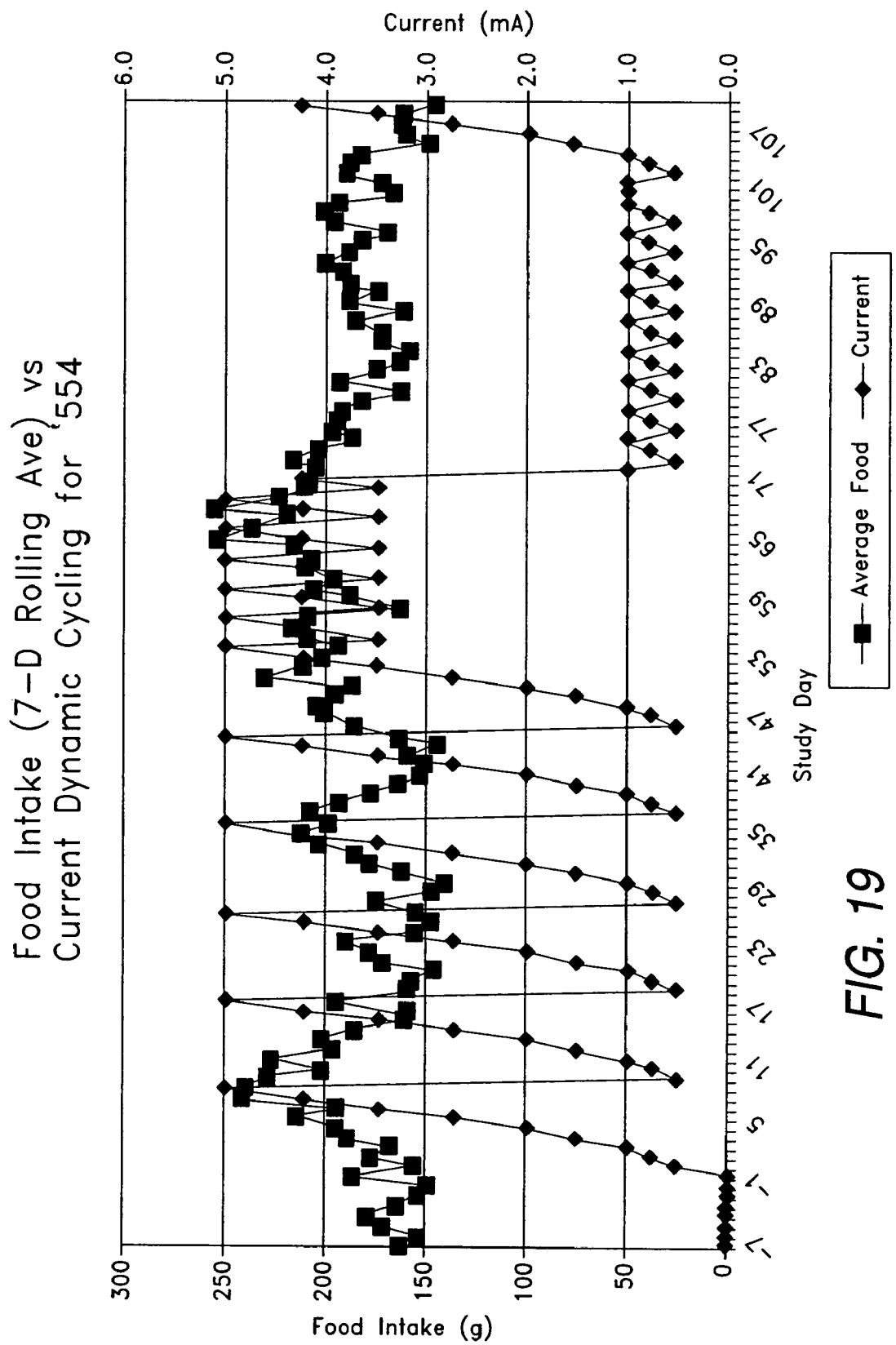
FIG. 19 shows the food intake (as a seven-day rolling average) and the current amplitude for canine subject '554, in which both the maximum stimulation intensity, and the level to which the stimulation intensity is decreased, are variable parameters.
Figure 20:
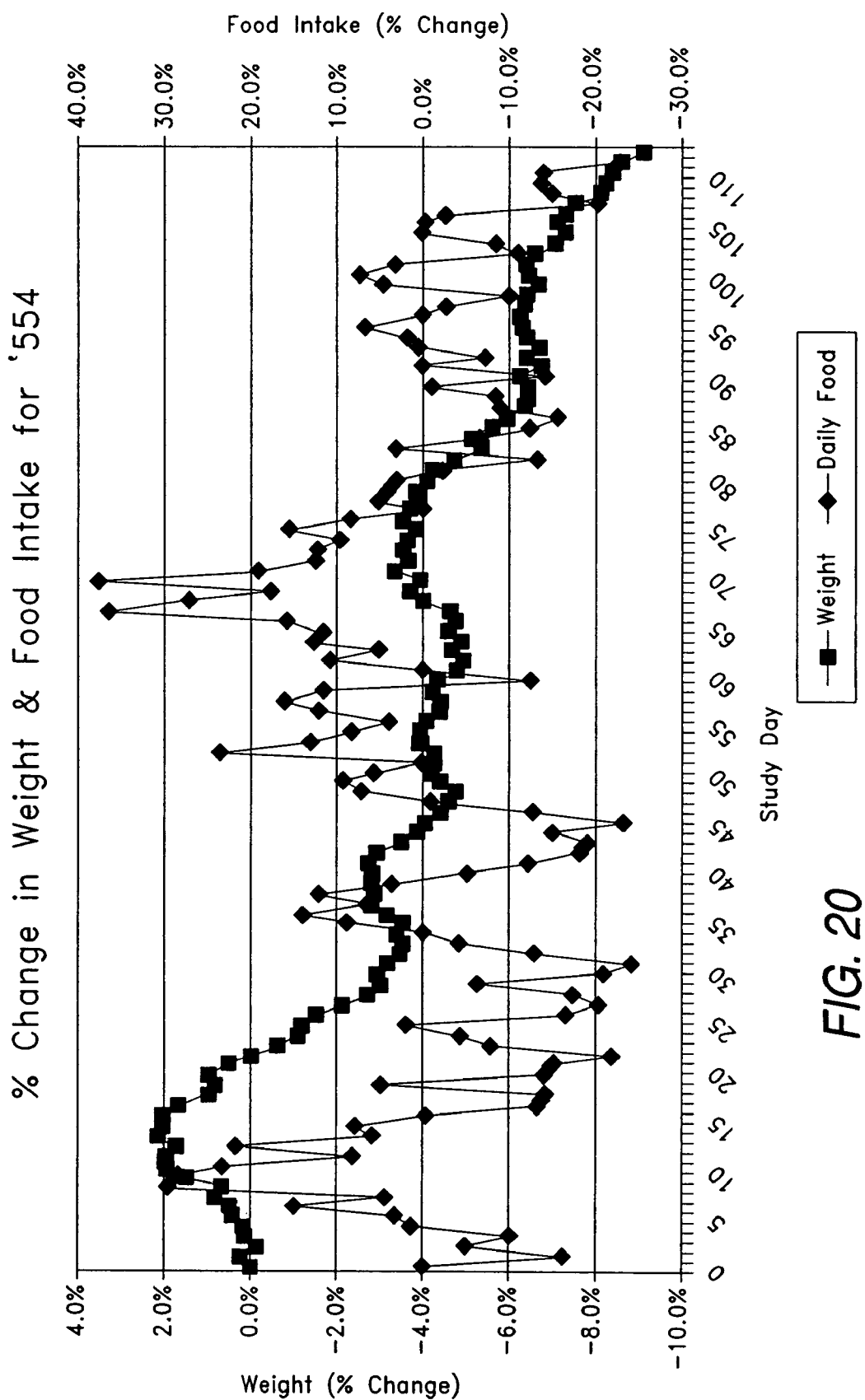
FIG. 20 shows the percent change (relative to day one) in weight and food intake for canine subject '554 over the course its ramp-cycling therapy in which both the maximum stimulation intensity, and the level to which the stimulation intensity is decreased, are variable parameters.

Shown in FIGS. 18-23 are the results obtained by employing a dynamic stimulation technique with ramp cycling where both the maximum stimulation intensity, and the level to which the stimulation intensity was decreased, were experimental variables. FIG. 20 shows the current amplitude and weight (calculated as a seven day rolling average) plotted against time in days for canine subject '554. The stimulation intensity was increased over a period of days by increasing the current amplitude. The stimulation intensity was then reduced in a single step down to a threshold value. This pattern was repeated for several cycles (approximately days 5 through 48). Following those cycles, the stimulation intensity was again increased back up to match the first series' maximum stimulation intensity; however, over the next several cycles, the stimulation intensity was not reduced down to the initial threshold level, but rather reduced to a level between the maximum stimulation intensity and the threshold stimulation intensity (approximately days 49 through 74). After several cycles of the abbreviated ramp, the stimulation pattern was changed again such that the maximum stimulation intensity was reduced to a relatively low value and the stimulation intensity decrease lowered the stimulation intensity down to the threshold value (approximately days 75 through 105). Thereafter, the entire pattern was reinitiated (beginning at approximately day 107).

The data shows that, while the overall trend towards weight loss demonstrated the efficacy of the embodiment, the animal's weight plateaued or began to increase, modestly, after approximately 10 days of both the high-end abbreviated ramp cycles (days 49 through 74) and the low-end abbreviated ramp cycles (days 75 through 105). This suggests that after extended periods of approximately constant stimulation intensity the body compensates for the stimulus, and the effects of the stimulation on weight are reduced or eliminated. This may mean that it is desirable to alternately activate and deactivate the groups of nerve fibers at intervals sufficiently separated in time to prevent such compensation. Consequently, an embodiment of the dynamic stimulation technique that may be desirable involves changing the stimulation intensity frequently enough, and substantially enough, to prevent compensation.

Figure 21:
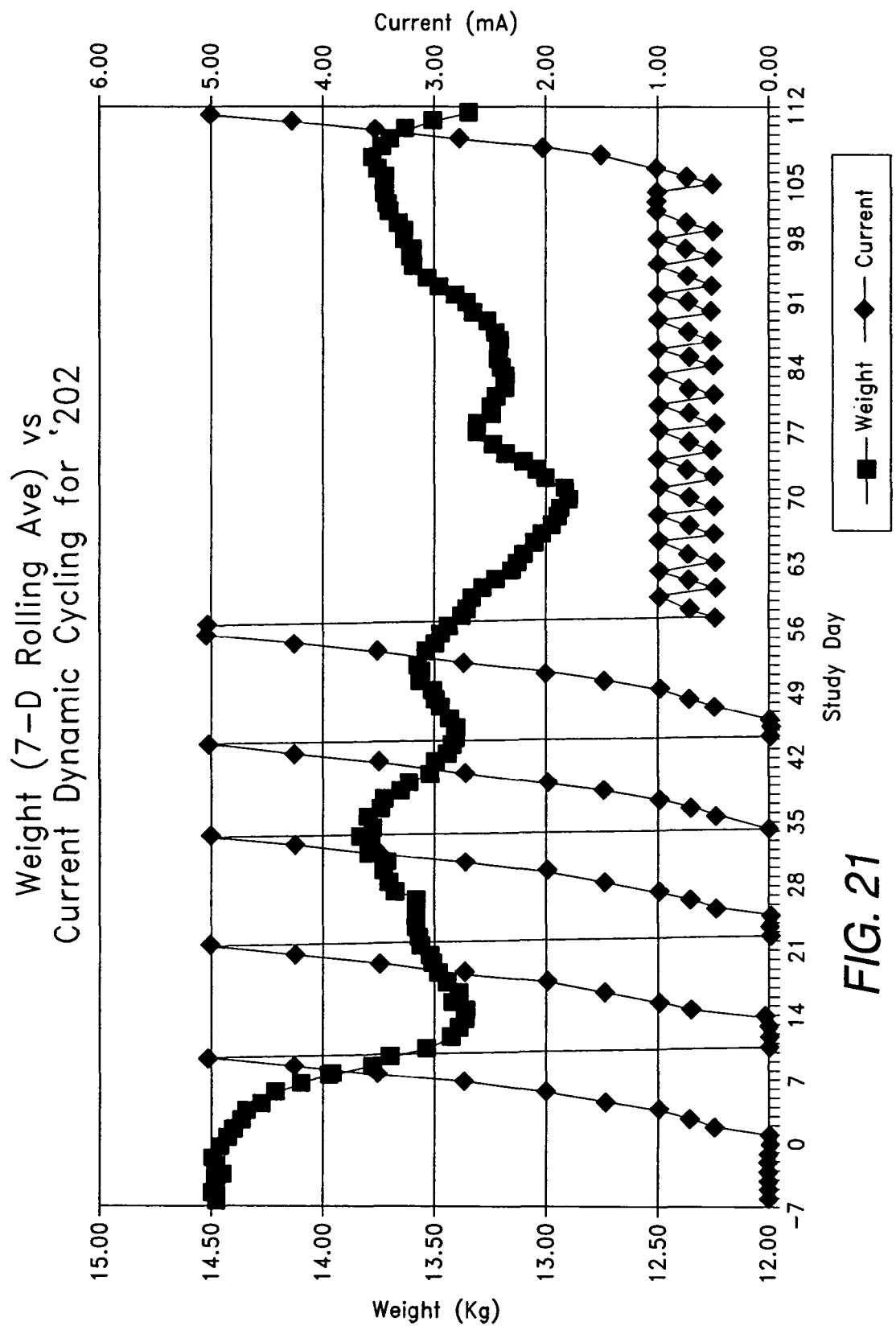
FIG. 21 shows the weight (as a seven-day rolling average) and the current amplitude for canine subject '202, in which both the maximum stimulation intensity, and the level to which the stimulation intensity is decreased, are variable parameters.

Similar features are observed in the data plotted in FIG. 21 for canine subject number '202. FIG. 21 shows the current amplitude and weight (calculated as a seven day rolling average) plotted against time in days for canine subject '202. The stimulation intensity was increased over a period of days by increasing the current amplitude. The stimulation intensity was then reduced in a single step down to a threshold value. This pattern was repeated for several cycles (approximately days 1 through 56). Following those cycles, the stimulation pattern was altered such that the maximum stimulation intensity in the new pattern was set to a value considerably lower than the maximum stimulation intensity of the previous group of cycles. Within the new pattern, the stimulation-intensity decrease after each maximum changed the stimulation intensity to the same threshold value as for the previous group of cycles (approximately days 56 through 105). Thereafter, the entire pattern was reinitiated (beginning at approximately day 106).

Once again, the data shows that, while the overall trend towards weight loss demonstrated the efficacy of the embodiment, the animal's weight plateaued or began to increase after approximately 10-12 days of the low-end, abbreviated ramp cycles (approximately days 56 through 105). When the maximum stimulation intensity was increased back up to the high value (approximately days 106 through 112) the rebound was halted, and the trend towards weight loss became more pronounced. This data, like the data for canine subject '554, supports the hypothesis that weight loss is amplified by preventing the body from compensating for the stimulation. This data also supports the hypothesis that one techniques for preventing the body from compensating for the stimulation that may be desirable is to change the maximum and/or minimum stimulation intensities of the ramp cycles at appropriate intervals, and optionally to do so in a manner such that one or more of the groups of nerve fibers (A, B and/or C fibers) are activated during one group of ramp cycles (e.g. days 0 through 56 in FIGS. 18 and 21) and deactivated during the next group of ramp cycles (e.g. the B and C fibers during days 77 through 105 in FIGS. 18 and 21).

Figure 22:
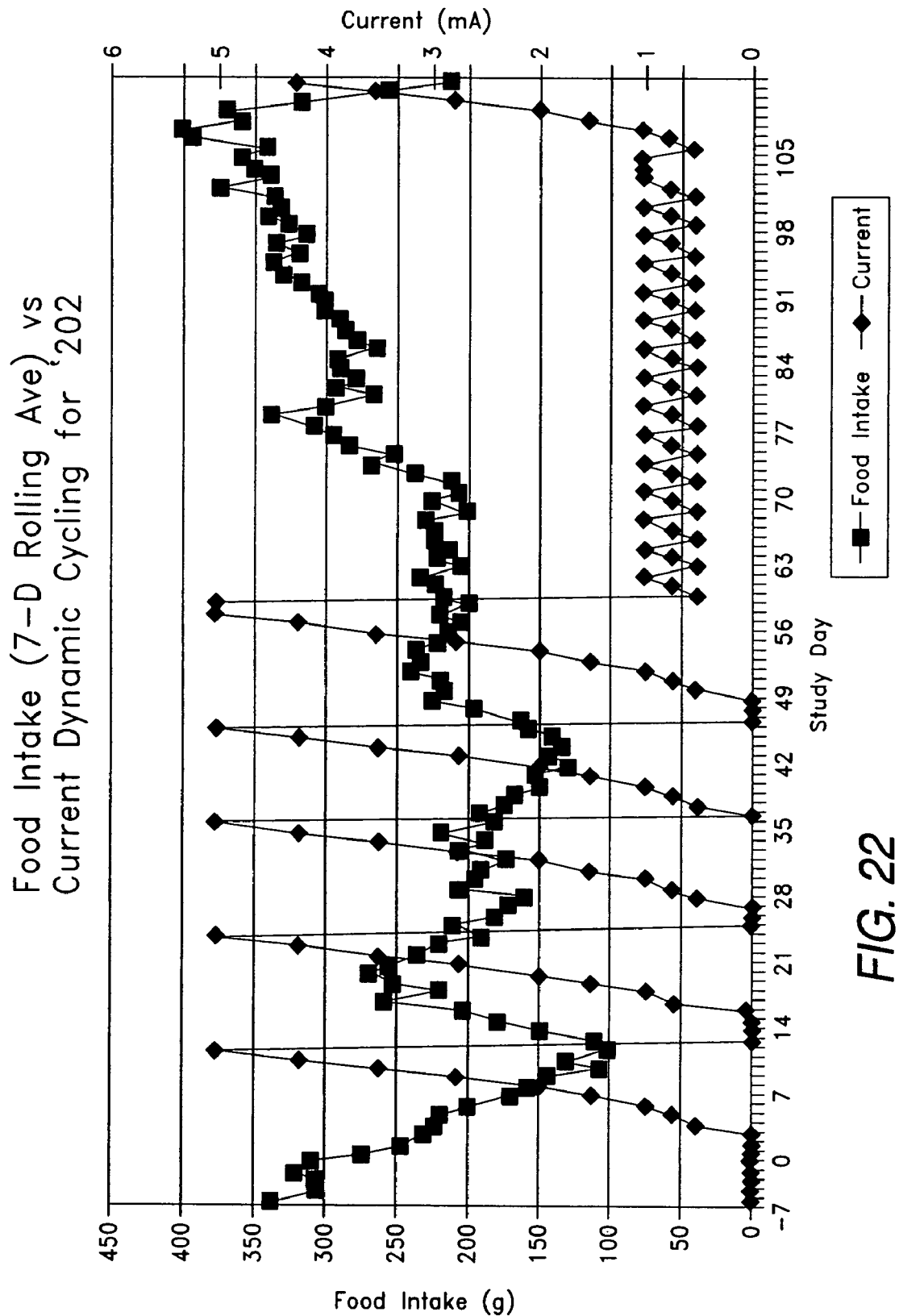
FIG. 22 shows the food intake (as a seven-day rolling average) and the current amplitude for canine subject '202, in which both the maximum stimulation intensity, and the level to which the stimulation intensity is decreased, are variable parameters.
Figure 23:
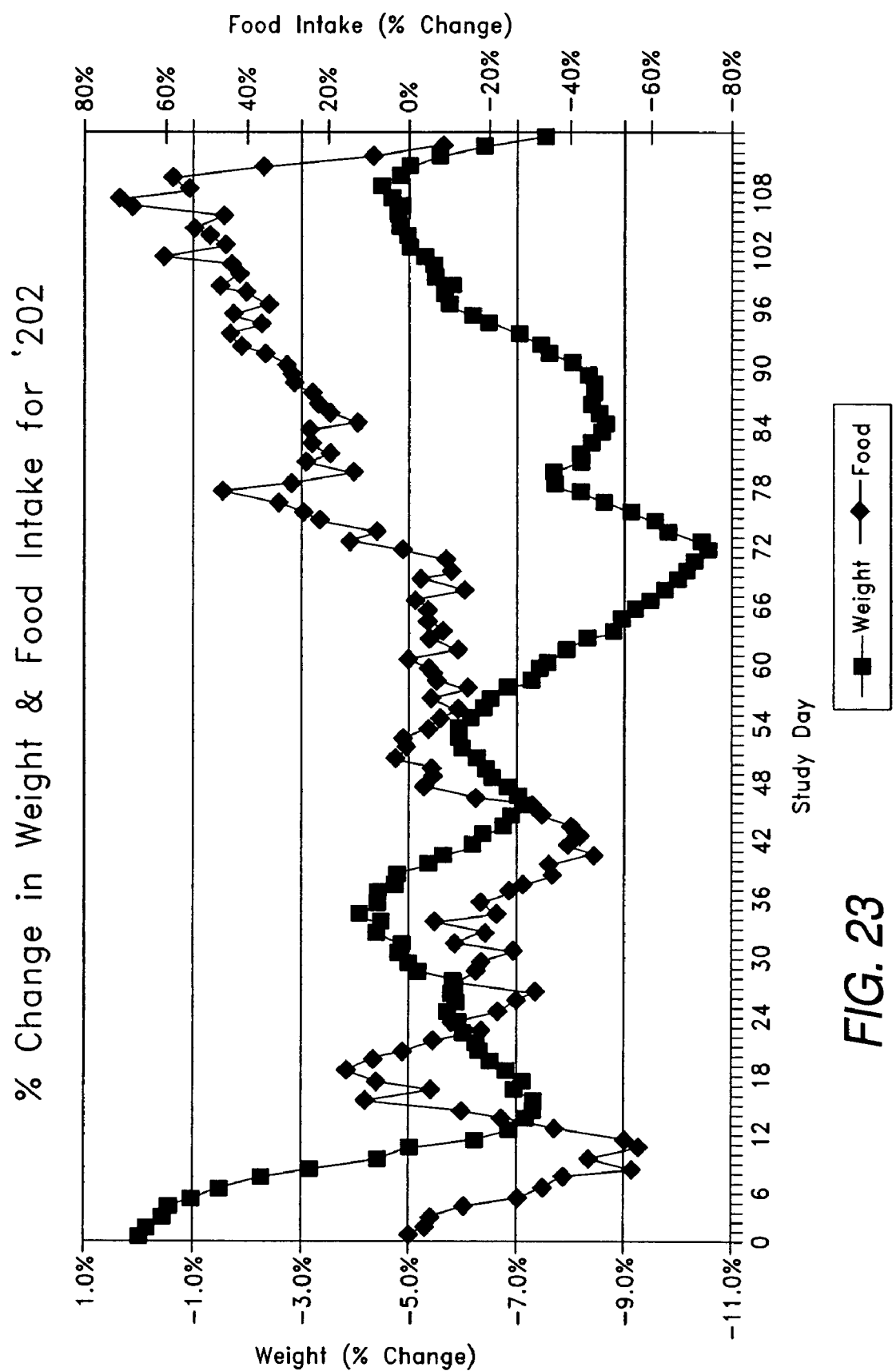
FIG. 23 shows the percent change (relative to day one) in weight and food intake for canine subject '202 over the course its ramp-cycling therapy in which both the maximum stimulation intensity, and the level to which the stimulation intensity is decreased, are variable parameters.

Additional support for the hypothesis described above may be found in FIGS. 19, 20, 22 and 23. FIGS. 19 and 22 show the current and daily food intake (calculated as a seven day rolling average) plotted against time in days for canine subjects '554 and '202, respectively, during the same studies described in the context of FIGS. 18 and 21. Similarly, FIGS. 20 and 23 show the weight and daily food intake plotted against time in days for canine subjects '554 and '202, respectively, during those studies. The data of FIGS. 20 and 23 reflect the net change in the magnitude of the given parameters relative to that parameter's value on the first day; they are not calculated as rolling averages. The data shows that the trend in each animal's food intake substantially tracked the changes in the animal's weight over the course of the experiment. Like the weight data, the food intake data for canine subject '554 shows that the animal's food intake plateaued or began to increase after approximately 10 days of both the high-end abbreviated ramp cycles (approximately days 49 through 74 of FIGS. 19 and 20) and the low-end abbreviated ramp cycles (approximately days 75 through 105 of FIGS. 19 and 20). Similarly, the food intake data for canine subject '202 shows that the animal's food intake plateaued or began to increase after approximately 10-12 days of the low-end, abbreviated ramp cycles (approximately days 56 through 105 of FIGS. 22 and 23). While the food intake data shows higher variability, they, too, suggest that weight loss using a ramp cycling technique may be amplified by changing the maximum and/or minimum stimulation intensities of the ramp cycles at appropriate intervals, and optionally to do so in a manner such that one or more of the groups of nerve fibers are alternately activated and deactivated.

The weight loss indicated in the data discussed above may be useful in the treatment of metabolic syndrome based on a variety of modalities. For example, obesity is a known contributing factor for hypertension. It follows that weight reduction in a patient not only treats the metabolic syndrome's and/or Type II diabetes' attendant or contributing condition of obesity directly, but also indirectly treats further attendant or contributing conditions of obesity, metabolic syndrome and/or Type II diabetes, such as hypertension.

Figure 24:
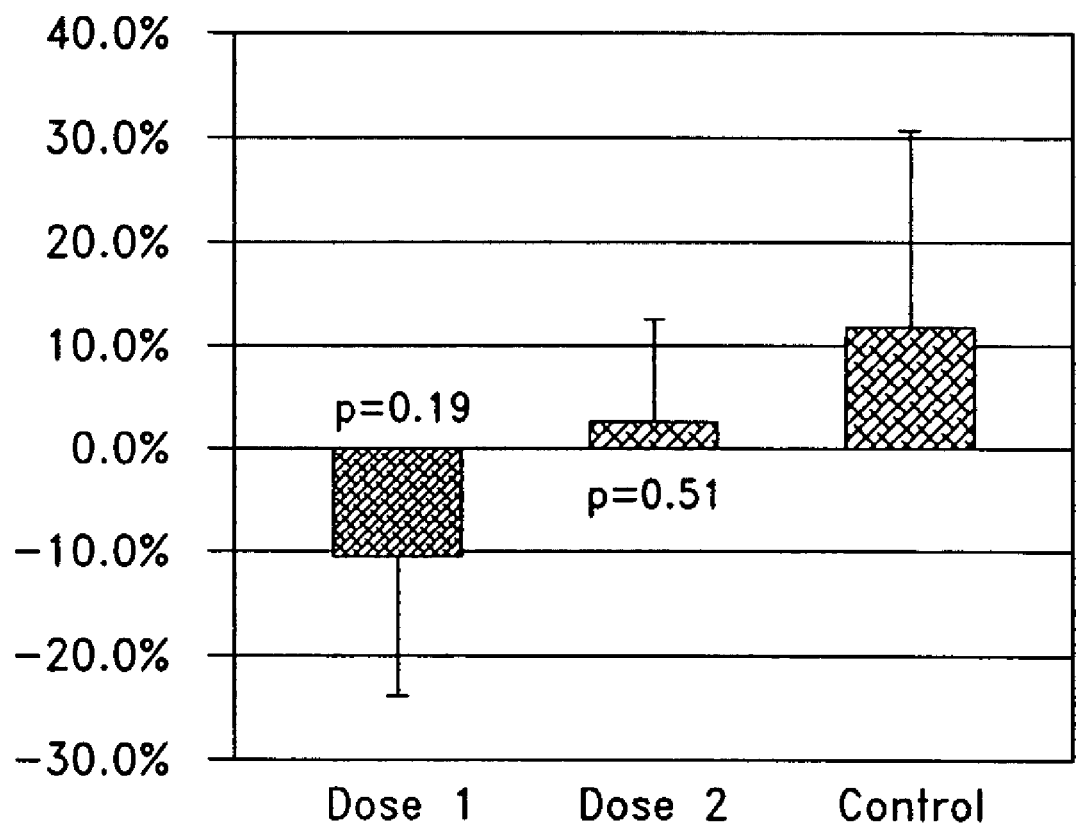
FIG. 24 is a graphical representation showing food intake changes versus baseline for test subjects.

In addition to a reduction in weight and food intake, modulation of sympathetic nerves may be useful in improving the composition of body tissue. For example, modulation of peripheral nerves may be used to lower the percentage of body fat and increase the percentage of lean body or lean muscle mass. For example, a stimulation treatment embodiment was carried out using 9 obese canine models divided into three groups or sets including a Dose 1 group (n=3), a Dose 2 group (n=3) and a Control group (n=3). Dosing parameters were established and the effects of the treatment were observed with regard to food intake, body mass and body composition. For this particular embodiment, the dosing for the Dose 1 group included a continuous stimulation embodiment with a frequency of about 20 Hz, a duty cycle of about 50% and a pulse width of about 500 microseconds. The dosing for the Dose 2 group was the same as the Dose 1 group except that the frequency used for nerve stimulation was 10 Hz. After 90 days of treatment, food intake was reduced by 10.8% per day in the Dose 1 group. Animals in the Control group increased food intake by 11.7% per day as shown in FIG. 24. FIG. 24 is a graphical representation showing percent daily food intake change versus baseline for test subjects including mean plus standard deviation value.

In certain embodiments, electrically activating a splanchnic nerve of a patient using a stimulation pattern may ameliorate or eliminate an attendant conditions of obesity, metabolic syndrome, and/or Type II diabetes in a patient. For example, attendant conditions such as dyslipidemia, hypertension, hyperinsulinemia, hyperglycemia, and insulin resistance may be affected. In certain embodiments, the stimulation pattern may ameliorate or eliminate an attendant condition of obesity, metabolic syndrome, and/or Type II diabetes without producing a significant net loss in total body weight. For example, in certain embodiments, lean muscle mass increases in a proportion approximately equal to or greater than an amount of fat mass that is lost. Such improvements in the attendant conditions of obesity, metabolic syndrome, and Type II diabetes occur due to, or at least accompany, an increase in the lean muscle mass of a patient, irrespective of the patient's loss of fat mass, as is well known to those of skill in the art.

Figure 25:
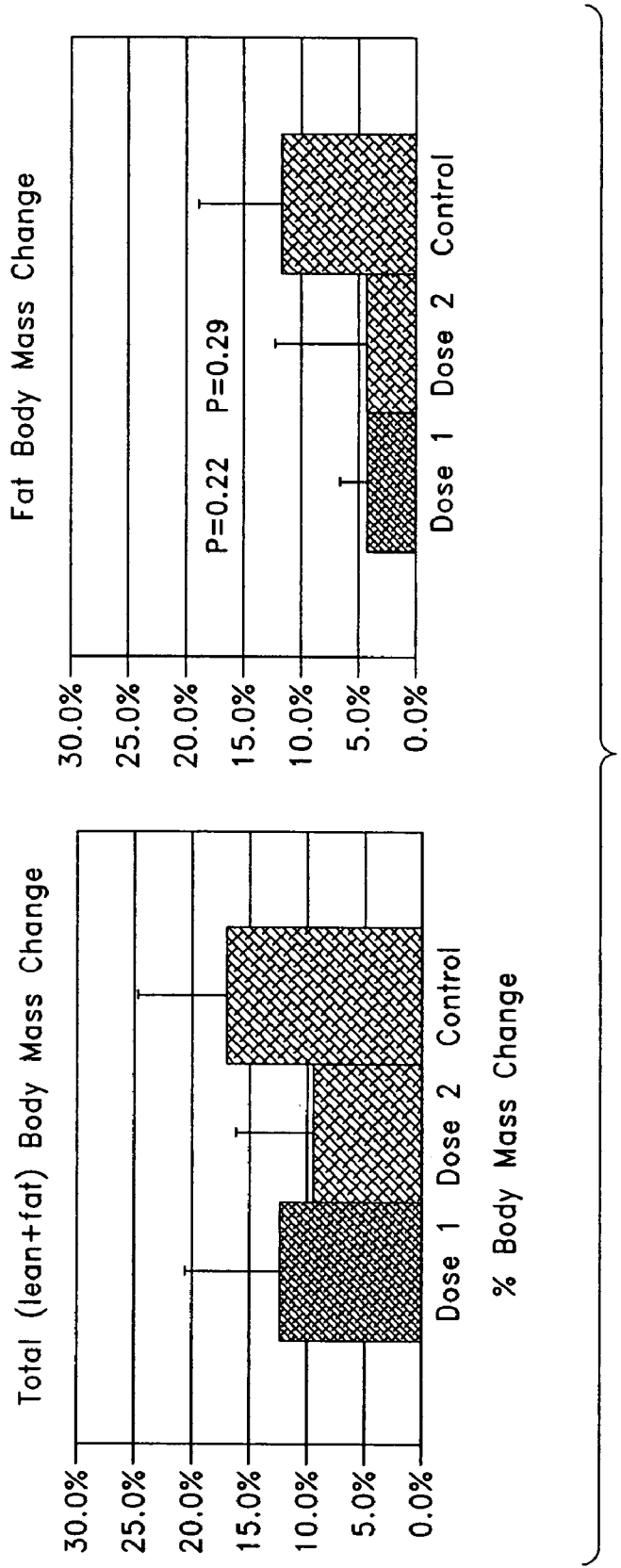
FIG. 25 is a graphical representation showing total body mass and fat body mass changes during a 90 day treatment embodiment indicating an increase in lean body mass.
Figure 26:
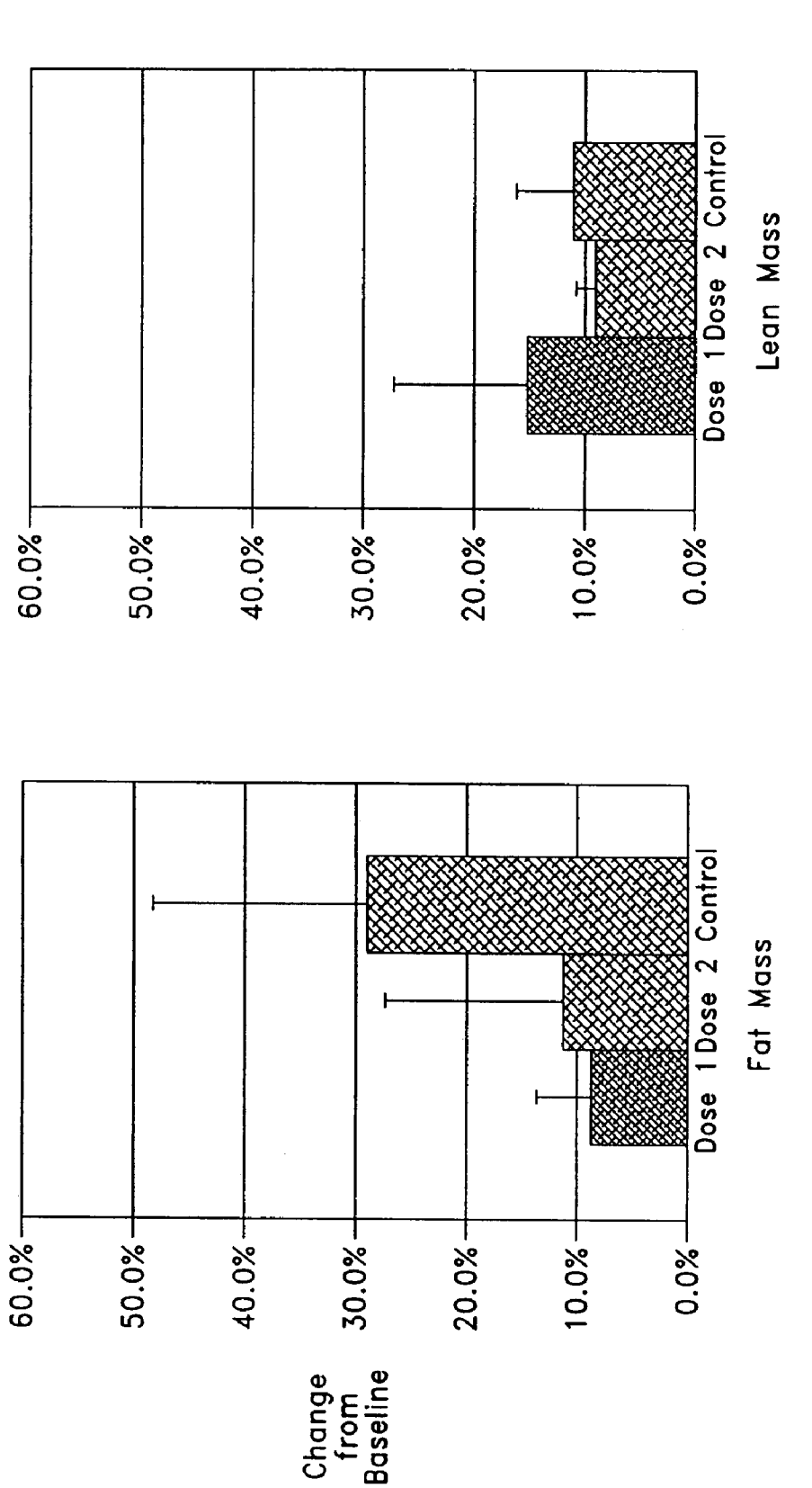
FIG. 26 is a graphical representation showing fat and lean body mass change from a baseline measurement as determined by a Dual Energy X-Ray Absorptiometry (DEXA) scan for two sets of test subjects and a control set.

Total body mass increased from a baseline period in all groups, but a smaller increase was observed in the treated animals as shown in FIG. 25 which is a graphical representation showing total body mass and fat body mass changes during a 90 day treatment embodiment showing mean values plus standard deviation and indicating an increase in lean body mass. Dual Energy X-Ray Absorptiometry (DEXA) scanning is a process which measures body composition including percentage of lean, fat and bone. DEXA scanning of the test groups showed that the total mass increase in the treated animals was predominantly due to an increase in lean body mass as depicted in FIGS. 25 and 26. FIG. 26 is a graphical representation showing fat and lean body mass change including mean value plus standard deviation from a baseline measurement as determined by a DEXA scan for two sets of test subjects and a control set.

Figure 27:
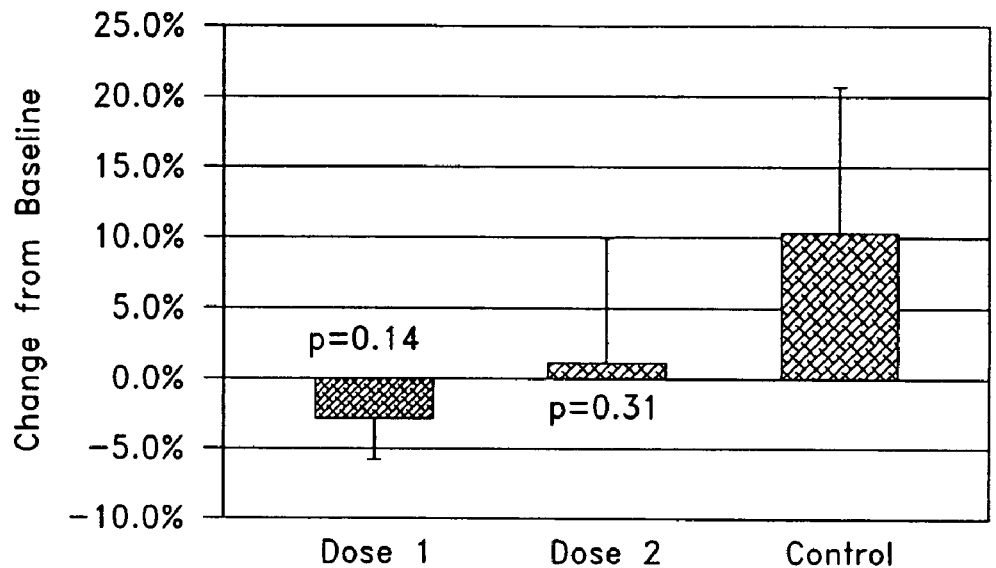
FIG. 27 is a graphical representation showing change in body fat as a percentage of total body mass for two sets of test subjects and a control set as determined by DEXA scanning.

The fat contribution to total body mass increase was only 35% in Dose 1 animals versus 72% in Control group animals. Consequently, the total percentage body fat declined in a dose dependent manner with Dose 1 showing the greatest decline as shown in FIG. 27. FIG. 27 is a graphical representation showing change in body fat as a percentage of total body mass including mean value plus standard deviation for two sets of test subjects and a control set as determined by DEXA scanning. Growth trends showed a sharp decline in body mass during stimulation ramping, and after a 1 month transition period, sustained reduction in weight gain relative to Control group animals. When stimulation was initially terminated, another sharp decline in food intake and body mass was observed, followed by a gradual return to baseline after 3 weeks.

These results indicate the ability of treatment embodiments to increase the lean tissue including lean muscle mass in a subject. Lean muscle tissue is believed to be a positive factor in the moderation of insulin levels, moderation of glucose levels and reduction in hypertension. As such, an increase in lean muscle mass may increase the ability of a subject suffering from metabolic syndrome to regulate insulin levels and alleviate at least some of the symptoms of insulin resistance associated with metabolic syndrome. An increase in lean muscle mass may also be helpful in reducing hypertension which is a attendant or contributing condition of metabolic syndrome.

Figure 27A:
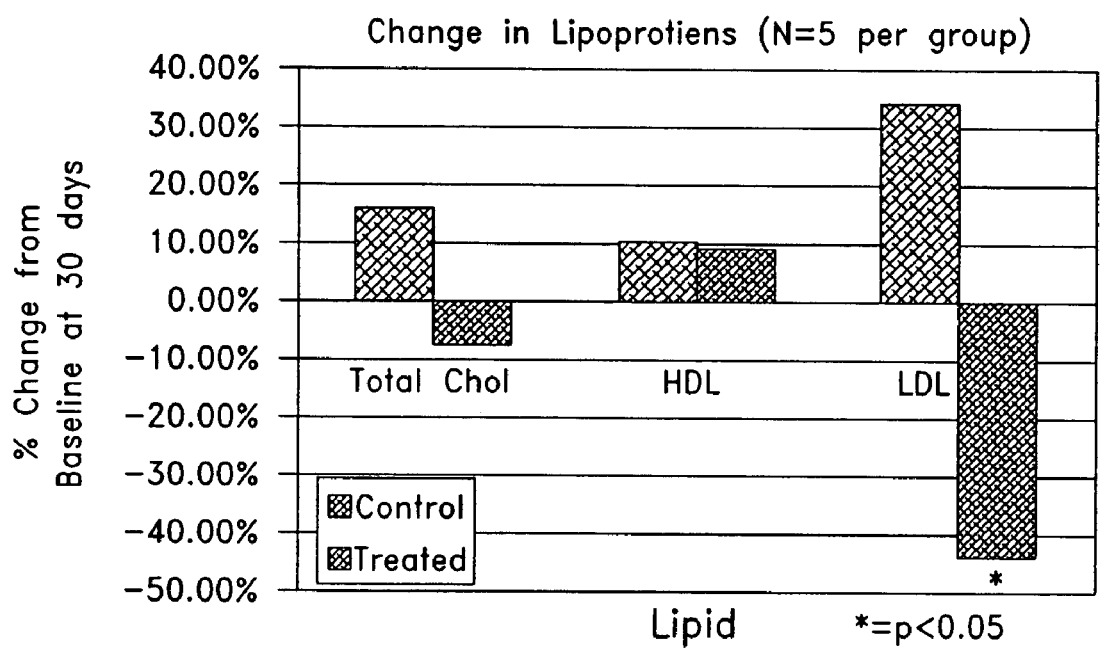
FIG. 27A illustrates graphical data showing percentage change in total cholesterol, HDL cholesterol and LDL cholesterol from baseline for canine test subjects.

Metabolic syndrome may also be treated by modulation of lipid levels in a patient which may include treatment of cholesterol (high density lipoproteins and low density lipoproteins) and triglyceride with a general reduction of low density lipoproteins (LDLs) and/or an increase in high density lipoproteins (HDLs) levels or a reduction in triglyceride levels of a patient. FIG. 27A illustrates graphical data showing percentage change in total cholesterol, including HDL cholesterol and LDL cholesterol levels from baseline for canine test subjects. More specifically, the graph illustrates a percentage change in lipid profile of canine test subjects over a 30 day period. A control group included 5 animals having no treatment and a treated group included 5 animals which were administered a 30 day treatment dosage that included a ramp cycling stimulation embodiment. The ramp cycling stimulation included a treatment signal having frequency of about 20 Hz and a pulse width of about 500 μsec. The treatment signal had an initial current of about 0.5 mA, increasing daily by 0.5 mA for 7 days to a current of about 3.5 mA, and then repeating for another 7 days. As can be seen from FIG. 27A, the results of the treatment embodiment show an overall reduction in total cholesterol and a significant reduction in LDL cholesterol showing a statistically significant overall improvement in at least a portion or portions of the lipid profile of the test subjects.

A method for treating metabolic syndrome may include stimulation of a nerve or nerves of the sympathetic nervous system for improving at least a portion of a lipid profile of a patient, and more specifically, stimulation of the splanchnic nerve of a patient in order to reduce LDLs, increase HDLs, decrease triglycerides or any combination thereof. Another treatment embodiment may include modulation of a nerve or nerves of the sympathetic nervous system to improve a patient's lipid profile generally.

It may also be possible to titrate a treatment algorithm or pattern to maintain a desired lipid profile or cholesterol level. For example, a level of HDL cholesterol may be measured by any suitable variety of methods or otherwise sensed by sensor. The level of HDL may then be communicated to a processor of a pulse generator which may compare the measured or sensed level to a predetermined target level and select treatment energy parameters or patterns which are configured to adjust the level to the target level. Such an arrangement may be controlled by a feedback loop or the like.

In certain embodiments of dynamic stimulation using the ramp-cycling technique, the stimulation intensity is initially set to a value approximately equal to the muscle twitch threshold. The stimulation intensity is then increased at regular intervals until the chosen maximum stimulation intensity is achieved, which may fall in a range of about 8 times to about 10 times the muscle twitch threshold. In some embodiments, the stimulation intensity is increased in regular increments and at regular intervals. In certain embodiments, the stimulation intensity is increased by about 10% to about 20% of the value of the previous stimulation intensity until the desired maximum stimulation intensity is attained. Once the desired maximum stimulation intensity is attained, the stimulation intensity is reduced in a single step to the muscle twitch threshold. Alternatively, the maximum stimulation intensity is reduced to the muscle twitch threshold through a plurality of stepwise decreases. In certain embodiments, the stimulation intensity is reduced to a value that is lower than the maximum stimulation intensity and higher than the muscle twitch threshold. For some embodiments, this pattern of increases and decreases is repeated, indefinitely.

Figure 28:
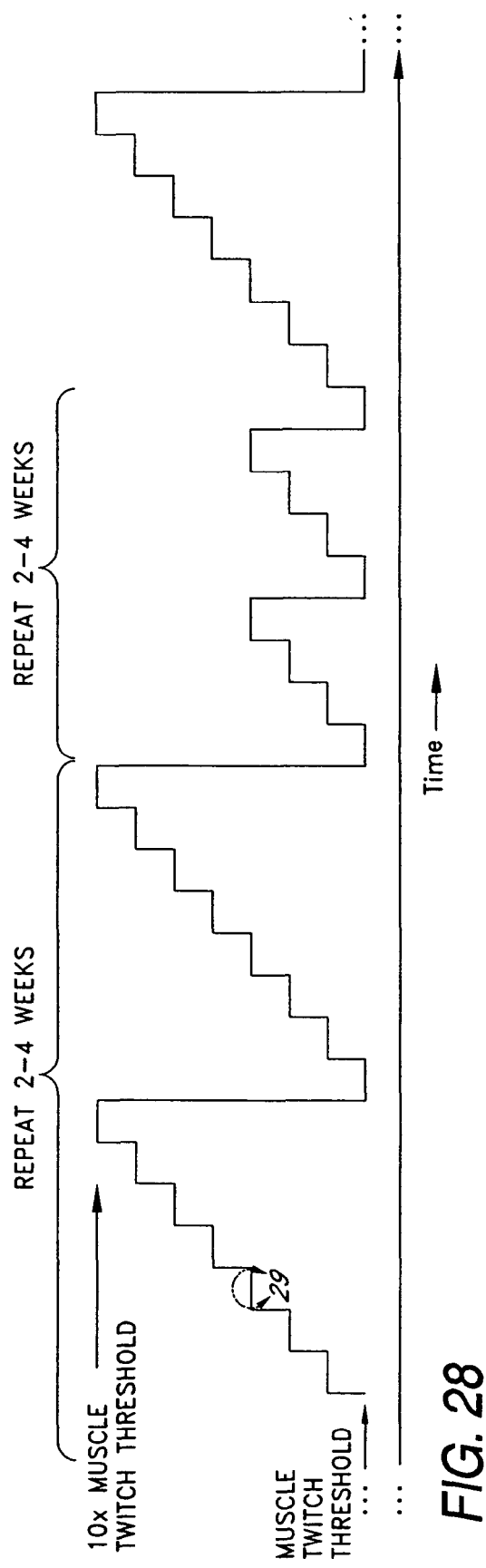
FIG. 28 shows a ramp-cycling technique where the maximum stimulation intensity is also a parameter that is varied over the course of multiple stimulation time periods.

In some embodiments, this pattern of increasing the stimulation intensity to about 8 times to about 10 times the muscle twitch threshold and reducing the stimulation intensity back down to about the muscle twitch threshold is repeated for a period of about 1 week to about 4 months. Following that period of about 1 week to about 4 months, the pattern is changed such that the maximum stimulation intensity for the next week to several months is set to about 2 times to about 4 times the muscle twitch threshold, rather than about 8 times to about 10 times the muscle twitch threshold. Following the second period of about 1 week to about 4 months, where the maximum stimulation intensity is set to a value equal to between about 2 times to about 4 times the muscle twitch threshold, the first cycle is re-instituted whereby the maximum peak intensity is set again to about 8 times to about 10 times the muscle twitch threshold for about 1 week to about 4 months. A schematic diagram of this embodiment is shown in FIG. 28. The overarching pattern of changes to the maximum stimulation intensity may then be repeated regularly or in a random pattern.

One advantage of these embodiments is that, during the pattern, different fiber types may be activated. In the cycles where the maximum peak intensity is between about 8 times to about 10 times the muscle twitch threshold, there is a progressive activation of fibers beginning with the A fibers and concluding with the C fibers. In the cycles where the maximum peak intensity is between about 2 times and about 4 times the muscle twitch threshold, the C fibers are not activated. Therefore, different fibers are activated for both short periods and long periods, thereby preventing compensation.

In addition, this allows for different nerve tissue to be stimulated by the same electrode by using a different stimulation or modulation signal. This may be used to achieve a different physiological result for each signal. For example, a first stimulation signal may be used to stimulate or modulate the splanchnic nerve to treat a first attendant or contributing condition of metabolic syndrome and a second stimulation signal may be used to treat a second attendant or contributing condition of metabolic syndrome. A third stimulation signal could be used to treat a third attendant or contributing condition of metabolic syndrome and so on. In addition, stimulation signals which are the same, similar or different may be used to stimulate different nerve tissues or nerves to achieve different physiological outcomes or treatments. For example, a stimulation signal may be applied with a particular treatment algorithm to the splanchnic nerve, such as those discussed above, to treat a metabolic syndrome attendant or contributing condition such as obesity, and specifically, lipolysis of abdominal or visceral fat. Reduction of abdominal or visceral fat may also be facilitated by increased energy expenditure or metabolic rate as a result of peripheral nerve stimulation, and for some embodiments, stimulation of the splanchnic nerve. A second stimulation signal or treatment algorithm may be applied to other nerve tissue or nerves such as the vagus nerve and used to treat a second attendant or contributing condition of metabolic syndrome.

With regard to additional stimulation treatment patterns, some embodiments of treating a patient by modulation of at least a portion of a sympathetic nervous system of a patient may include activating a splanchnic nerve of the patient with a first electrical signal during an activation interval and inhibiting nerve transmission of the splanchnic nerve of the patient with a second electrical signal during an inhibition interval. The activation and inhibition may be carried out at different times relative to each other. For some embodiments, the modulation includes a plurality of activation intervals and a plurality of inhibition intervals. Each activation interval is alternated with an inhibition interval in order to reduce tolerance to the modulation by the sympathetic nervous system of the patient. Tolerance to the modulation may include habituation, compensation, tachyphylaxis as well as other mechanisms. In some cases, the length of the activation intervals may be substantially equal to the length of the inhibition intervals. In certain embodiments, the length of the activation intervals may be greater than the length of the inhibition intervals. For example, in some embodiments, the length of the activation intervals is about 1.5 times to about 10 times greater than the length of the inhibition intervals. Such embodiments of stimulation patterns may be used to treat metabolic syndrome, obesity, or any of the attendant or contributing conditions of metabolic syndrome.

In addition to the desirability of the ramp-cycling subset of dynamic stimulation, it may also be desirable to alter the stimulation frequency and/or the duty cycle instead of, or concurrent with, the intermittent therapy based on changes to the stimulation intensity. Changes to the stimulation frequency and/or the duty cycle may operate to optimize the activation of a given subset of fibers. During periods where the stimulation intensity is at a relatively low value, and thus large fibers are selectively activated, one may use relatively high stimulation frequencies and higher-valued duty cycles. In some embodiments, the stimulation frequency is about 20 Hz to about 30 Hz, and the stimulation duty cycle is set to about 30% to about 50%. During periods where the stimulation intensity is at a relatively high value, and thus small fibers are selectively activated, it may be desirable to use relatively low stimulation frequencies and relatively lower-valued duty cycles. In some embodiments, the stimulation frequency may be about 10 Hz to about 20 Hz, and the stimulation duty cycle is set to about 20% to about 30%.

It may also be desirable to alter the stimulation duty cycle and stimulation frequency during each stimulation intensity interval. Thus, for a given value of the stimulation intensity, the stimulation duty cycle or stimulation frequency, or both, may be varied according to a preselected pattern or they may be varied randomly. In some embodiments, the stimulation duty cycle may be varied between about 1% and about 100%. In certain embodiments, the stimulation duty cycle may be varied between about 5% and about 50%. In certain embodiments, the stimulation frequency may be varied between about 1 Hz and about 500 Hz. In certain embodiments, the stimulation frequency may be varied between about 2 Hz and about 100 Hz. In certain embodiments, the stimulation frequency may be varied between about 5 Hz and about 30 Hz.

Figure 29:
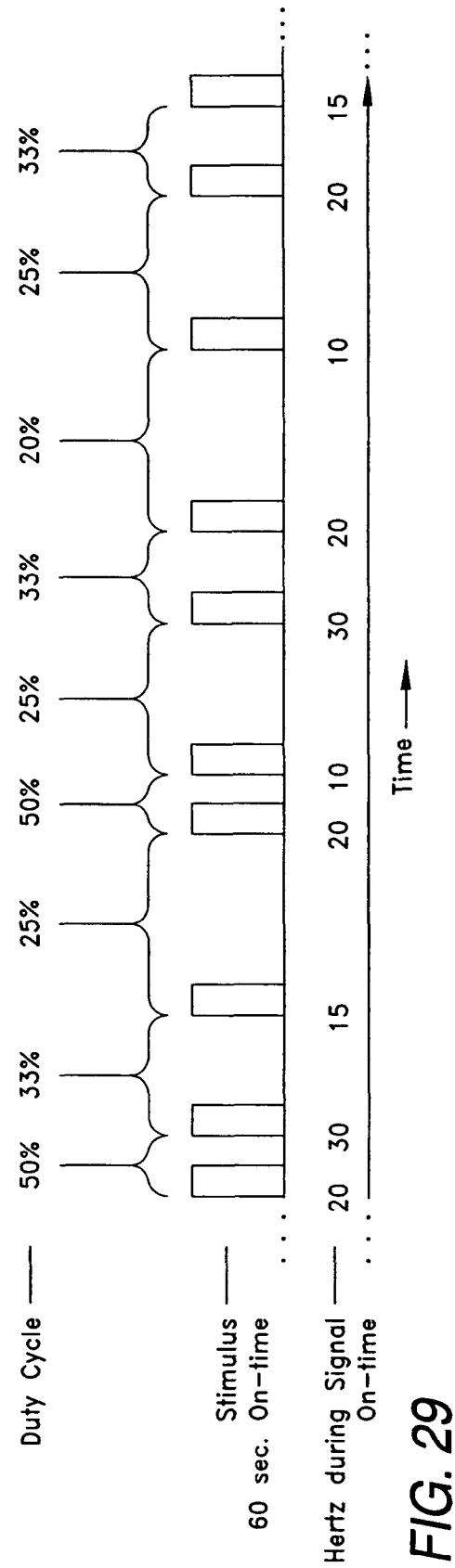
FIG. 29 shows a dynamic stimulation technique where the stimulation frequency and stimulation duty cycles are varied within a signal on-time.

In certain embodiments, the changes in the stimulation duty cycle may be accomplished by fixing the signal on-time to a certain duration (e.g. about 15 seconds to about 60 seconds), and the signal-off time may be varied from about 15 seconds to about 5 minutes. In certain embodiments, the fixed signal on-time would be a suprathreshold period, as described above. This may be accomplished randomly or through a preset pattern such as 50%, 33%, 25%, 20%, 10% that repeats upward and/or downward indefinitely. In certain embodiments, the on-time may comprise both suprathreshold and subthreshold periods. In certain embodiments, the suprathreshold period would be longer than the subthreshold period. In certain embodiments, to substantially reduce the likelihood of nerve damage, the average stimulation duty cycle, as calculated over the entire treatment interval, should not be significantly higher that about 50%. In certain embodiments, the stimulation frequency may be varied during each on-time within the intervals where the stimulation duty cycle is varied. This may also be done randomly or in a pattern. The pattern may be one where the stimulation frequency is increased or decreased in a stepwise manner through the frequencies 30 Hz, 20 Hz, 15 Hz, and 10 Hz. This pattern may repeat indefinitely. A schematic representation of one possible stimulation frequency pattern, coupled with one possible duty cycle pattern, at one possible stimulation intensity, is shown in FIG. 29, which is itself an enlargement of a portion of FIG. 28.

It is noted that those of skill in the art may use the term "duty cycle" to mean different things in different contexts. For example, where the signal on-time is set to a fixed value, as described above, one might refer to the duty cycle as being "longer" or "shorter," depending on the length of the off time. This reflects the use of the term duty cycle to mean the total period for one signal on/off cycle. If there is any ambiguity, one of ordinary skill in the art will understand from the context or the units provided whether the quantity being referred to is the total time, or the ratio of the signal on-time to the sum of the signal on-time plus the signal off time, the definition primarily used herein.

Similarly, in certain embodiments, for example, where the suprathreshold period is set to a fixed value, as described above, one might refer to the duty cycle as being "longer" or "shorter," depending on the length of the subthreshold period. This reflects the use of the term duty cycle to mean the total period for one suprathreshold/subthreshold period cycle. If there is any ambiguity, one of ordinary skill in the art will understand from the context or the units provided whether the quantity being referred to is the total time, or the ratio of the suprathreshold period to the sum of the suprathreshold period plus the subthreshold period, the definition primarily used herein.

Because branches of the splanchnic nerve directly innervate the adrenal medulla, electrical activation of the splanchnic nerve results in the release of catecholamines (epinephrine and norepinephrine) into the blood stream. In addition, dopamine and cortisol, which also raise energy expenditure, may be released as a result of stimulation of the splanchnic nerve. Catecholamines can increase energy expenditure by about 15% to 20%. By comparison, subitramine, a pharmacologic agent used to treat obesity, increases energy expenditure by approximately only 3% to 5%.

Figure 30:
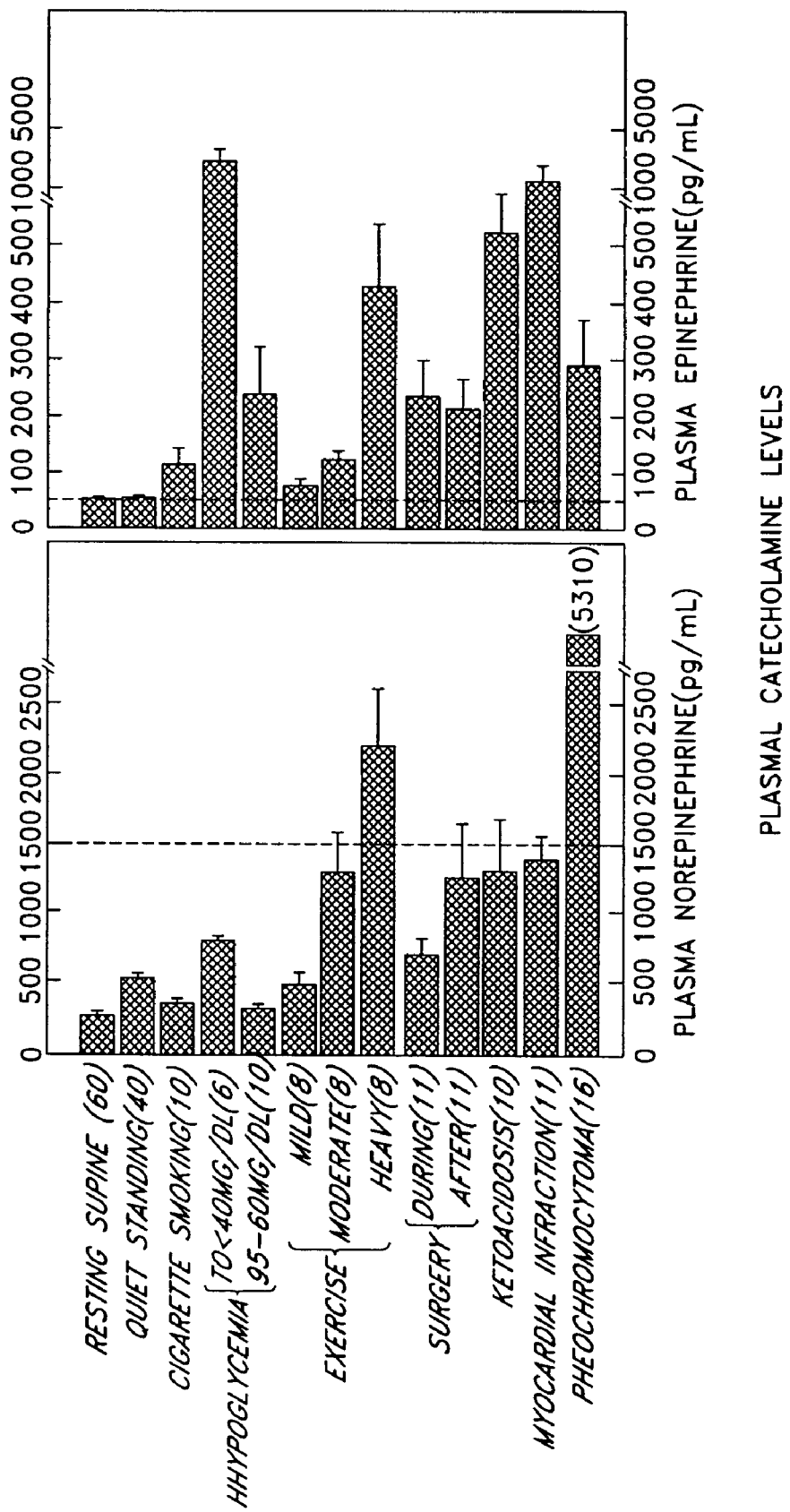
FIG. 30 is a graph of known plasma catecholamine levels in various physiologic and pathologic states.

Human resting venous blood levels of norepinephrine and epinephrine are approximately 25 pg/mL and 300 pg/mL, respectively, as shown in FIG. 30. Detectable physiologic changes such as increased heart rate occur at norepinephrine levels of approximately 1,500 pg/mL and epinephrine levels of approximately 50 pg/mL. Venous blood levels of norepinephrine may reach as high 2,000 pg/mL during heavy exercise, and levels of epinephrine can reach as high as 400 to 600 pg/mL during heavy exercise. Mild exercise produces norepinephrine and epinephrine levels of approximately 500 pg/mL and 100 pg/mL, respectively. It may be desirable to maintain catecholamine levels somewhere between mild and heavy exercise during electrical sympathetic activation treatment for obesity.

Figure 31:
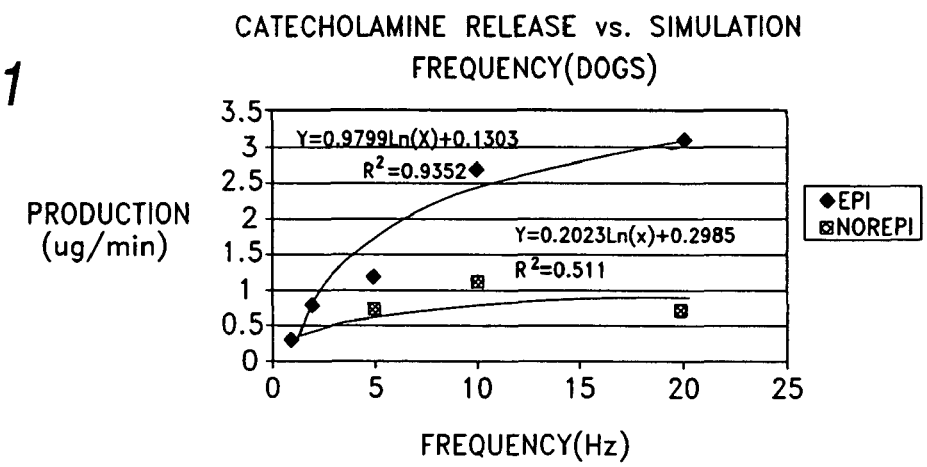
FIGS. 31-33 are exemplary graphs of the effect of splanchnic nerve stimulation on catecholamine release rates, epinephrine levels, and energy expenditure, respectively.
Figure 32:
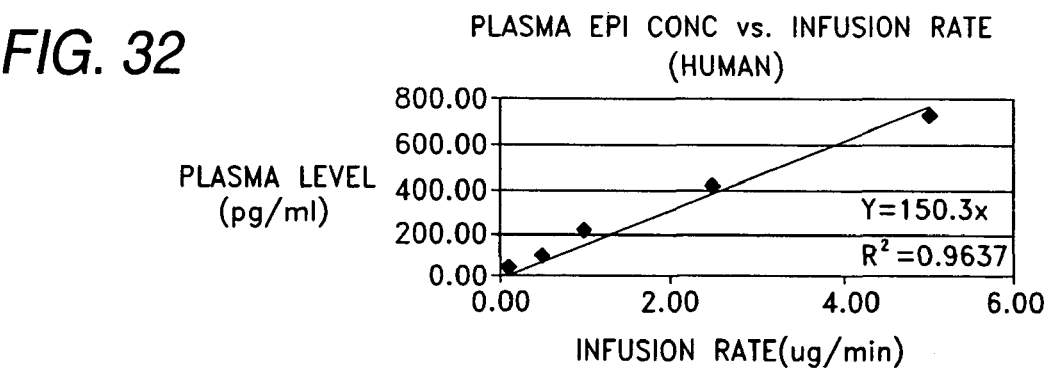
Figure 33:
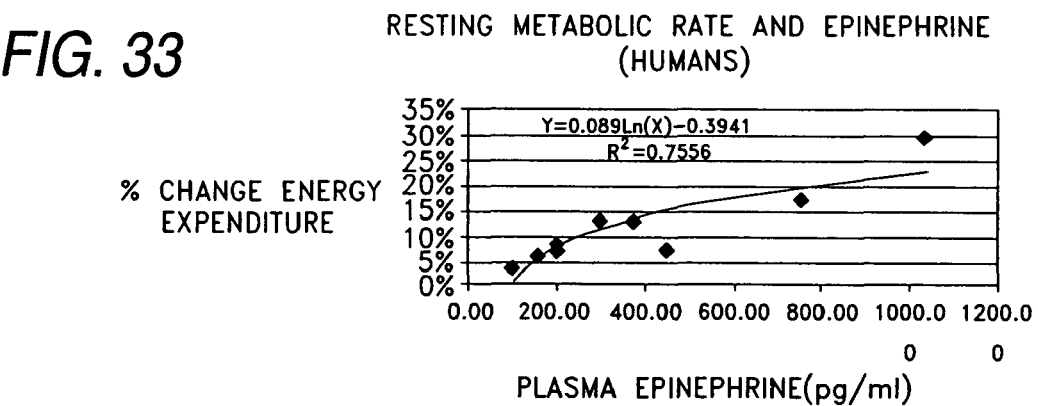

In anesthetized animals, electrical stimulation of the splanchnic nerve has been shown to raise blood catecholamine levels in a frequency dependent manner in the range of about 1 Hz to about 20 Hz, such that rates of catecholamine release/production of about 0.3 µg/min to about 4.0 µg/min can be achieved. These rates are sufficient to raise plasma concentrations of epinephrine to as high as about 400 pg/mL to about 600 pg/mL, which in turn can result in increased energy expenditure from about 10% to about 20% as shown in FIGS. 31-33. During stimulation, the ratio of epinephrine to norepinephrine may be about 65% to about 35%. One can change the ratio by stimulating at higher frequencies. In some embodiments this may be desirable to alter the energy expenditure and/or prevent a rise in MAP.

Energy expenditure in humans ranges from approximately 1.5 kcal/min to 2.5 kcal/min. A 15% increase in this energy expenditure in a person with a 2.0 kcal/min energy expenditure would increase expenditure by 0.3 kcal/min. Depending on treatment parameters, this may result in an additional 100 to 250 kcal of daily expenditure and 36,000 to 91,000 kcal of yearly expenditure. One pound of fat is 3500 kcal, yielding an annual weight loss of 10 to 26 pounds.

Increased energy expenditure is fueled by fat and carbohydrate metabolism. Postganglionic branches of the splanchnic nerve innervate the liver and fat deposits of the abdomen. Activation of the splanchnic nerve may result in fat metabolism and the liberation of fatty acids, as well as glycogen breakdown and the release of glucose from the liver. Fat metabolism coupled with increased energy expenditure can result in a net reduction in fat reserves. The splanchnic nerve innervates the abdominal or visceral fat deposits. As such, proper stimulation or other modulation of the splanchnic nerve may be effective in reducing abdominal fat. Abdominal fat is believed to play a role in mediating the inflammatory processes associated with hormonal activity of metabolic syndrome. As such, a reduction of abdominal fat may reduce the levels of hormones secreted by abdominal fat, such as leptin.

Figure 34:
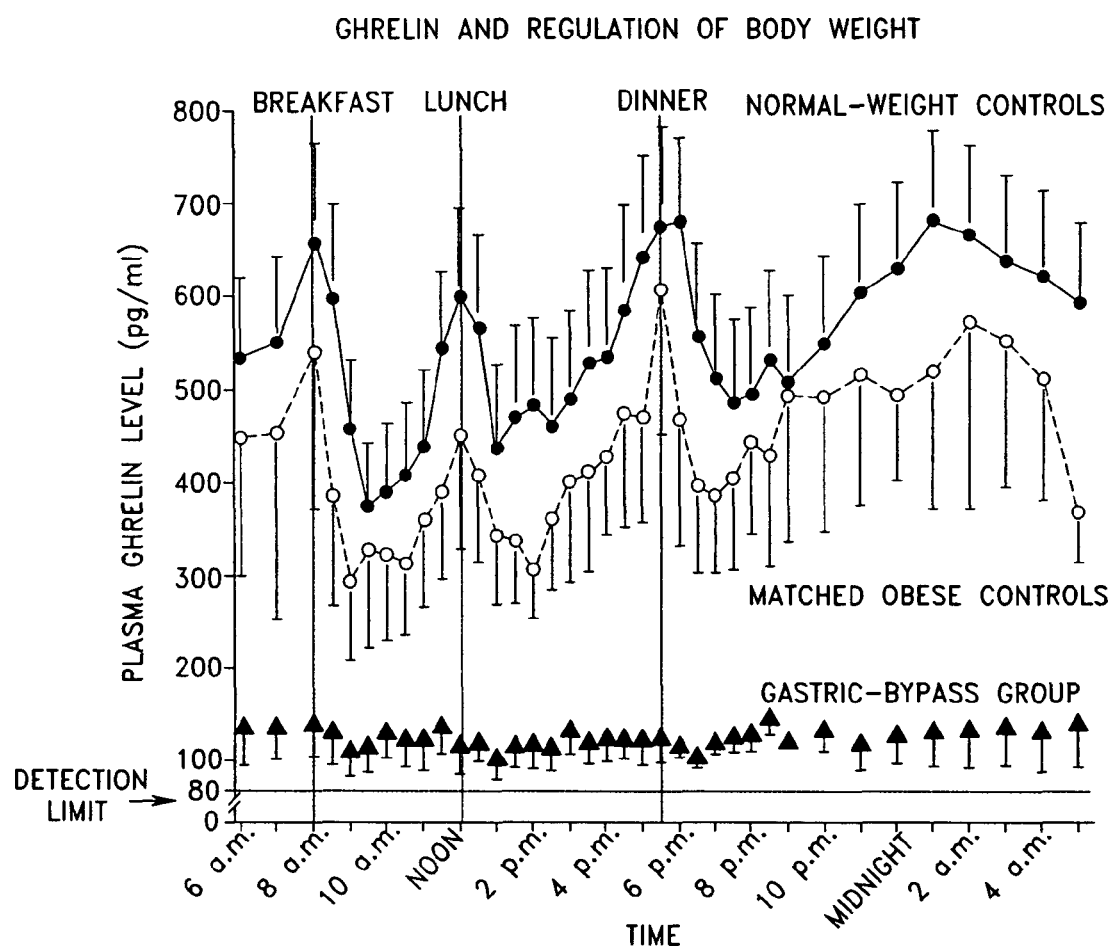
FIG. 34 is a graphical view of known plasma ghrelin levels over a daily cycle, for various subjects.
Figure 35:
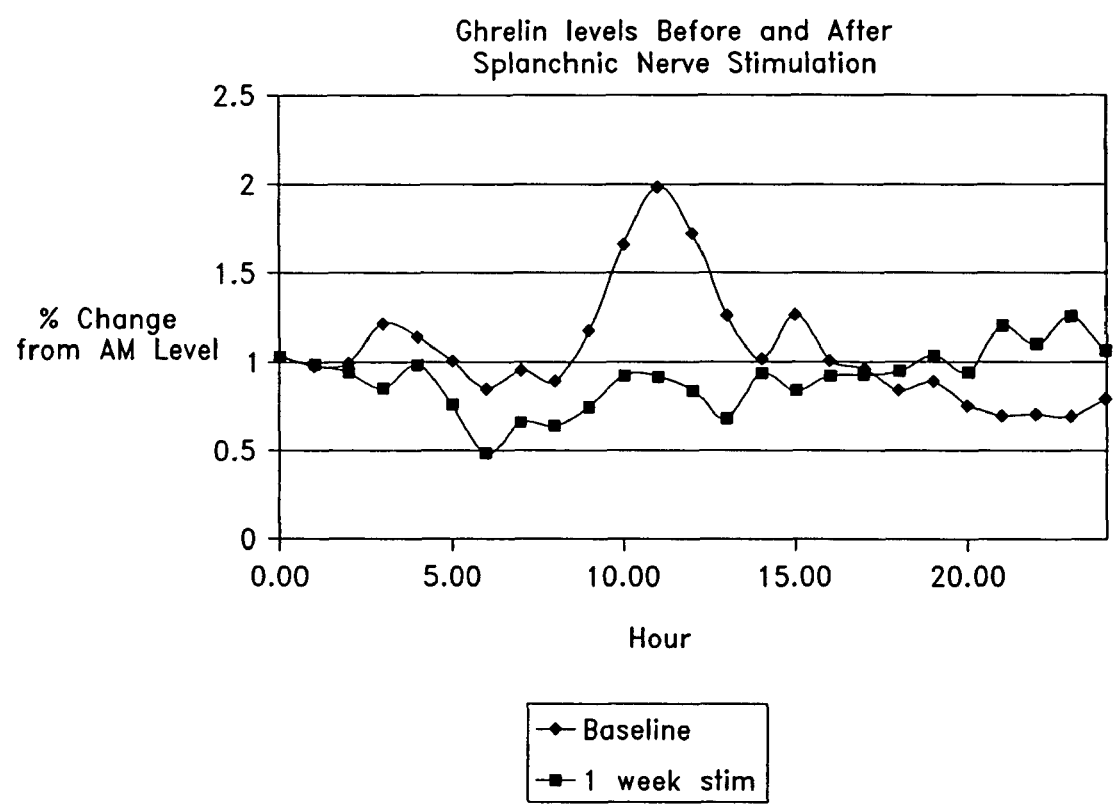
FIG. 35 is a graphical representation showing plasma ghrelin levels before and after splanchnic nerve stimulation.

In some embodiments, it may be desirable to titrate obesity therapy to plasma ghrelin levels. In humans, venous blood ghrelin levels range from approximately 250 pg/mL to greater than about 700 pg/mL as shown in FIG. 34. Ghrelin levels rise and fall during the day with peak levels typically occurring just before meals. Ghrelin surges are believed to stimulate appetite and lead to feeding. Surges in ghrelin may be as high as about 1.5 to about 2.0 times that of basal levels. The total ghrelin production in a 24 hour period is believed to be related to the energy state of the patient. Dieting that results in a state of energy deficit is associated with a higher total ghrelin level in a 24 hour period. Splanchnic nerve stimulation has been shown to eliminate or substantially reduce ghrelin surges or spikes. In a canine model, ghrelin levels prior to splanchnic nerve stimulation showed a midday surge of almost 2.0 times basal levels. After one week of stimulation at 20 Hz, on-time of approximately 60 seconds, off-time of approximately 120 seconds, and a peak current intensity of 8 times the muscle twitch threshold, this midday surge was almost eliminated as shown in FIG. 35. In addition, it increased the total ghrelin production in a 24 hour period, reflecting an energy deficient state (baseline area under the curve=$64.1 \times 10^4$, stimulation area under the curve=$104.1 \times 10^4$). Splanchnic nerve activation, in the treatment of obesity, can be titrated to reduce ghrelin surges and attain the desired energy deficit state for optimal weight loss. Reductions in food intake comparable to the increases in energy expenditure (i.e. 100 to 250 kcal/day) can yield a total daily kcal reduction of 200 to 500 per day, and 20 to 50 pounds of weight loss per year.

As discussed above, one of the attendant or contributing conditions of metabolic syndrome is obesity, often with the patient having excess white adipose tissue in the abdominal area. Some studies have concluded that white adipose tissue (WAT) does not function merely as a passive energy storage depot for the body, but functions as an active component of the endocrine system by secreting a variety of active substances, including adipokines such as tumor necrosis factor α (TNF-α) and adiponectin. It has also been found that indicators of systemic inflammation are present in obese patients, often with an elevated level of TNF-α, which is an inflammatory adipokine. TNF-α is also believed to be a significant cause or contributing factor in insulin resistance, a primary factor in development of metabolic syndrome. It follows that metabolic syndrome may be treated by reducing inflammatory adipokines such as TNF-α, which may in turn reduce insulin resistance in a patient suffering from metabolic syndrome.

The splanchnic nerve innervates the abdomen, including WAT of the abdomen. This suggests that modulation of the secretion of adipokines may be achieved by stimulation or modulation of sympathetic nerves, and specifically, modulation of the splanchnic nerve. In certain embodiments, metabolic syndrome is treated by reducing insulin resistance in a patient by stimulation of at least one sympathetic nerve in order to reduce WAT of the abdominal region and thereby decreasing secretion of inflammatory adipokines, such as TNF-α, from WAT of the abdomen. In certain embodiments, metabolic syndrome is treated by modulation or stimulation of a sympathetic nerve to directly reduce secretion of inflammatory adipokines, such as TNF-α. In certain embodiments, metabolic syndrome is treated by modulation of a sympathetic nerve in order to increase secretion of anti-inflammatory adipokines, such as adiponectin, from WAT of the abdomen. The modulation or stimulation of the sympathetic nerves may be carried out by any of the devices or methods discussed herein.

In addition, as discussed above, some embodiments of treatment of test subjects by stimulation of sympathetic nerves have produced and increase in lean muscle mass and certain embodiments of treatment by stimulation of sympathetic nerves have been discussed which increase the metabolic rate of patients. This suggests that such treatment embodiments may simulate physical exercise to some degree along with at least some of the benefits of physical exercise. Some recent findings regarding the benefits of physical exercise conclude that physical exercise results in the release or up-regulation of some positive factors or hormones such as interleuken-6 (IL-6). IL-6 has been shown to reduce levels of TNF-α and have an anti-inflammatory effect. As such, metabolic syndrome may be treated by reducing insulin resistance in a patient by stimulation of at least one sympathetic nerve in order to stimulate secretion or increased secretion of anti-inflammatory hormones such as IL-6. The modulation or stimulation of the sympathetic nerves may be carried out by any of the devices or methods discussed herein.

It may also be possible to titrate the peripheral nerve stimulation algorithm or pattern to achieve desired levels of catecholamines, ghrelin, cholesterol, adipokines etc. by sensing levels and adjusting treatment algorithms or patterns. As discussed above with regard to cholesterol levels, a level of catecholamine or other level may be measured by any suitable variety of methods or otherwise sensed by sensor. The level of catecholamine may then be communicated to a processor of a pulse generator which may compare the measured or sensed level to a predetermined target level and select treatment energy parameters or patterns which are configured to adjust the level to the target level. Such an arrangement may be controlled by a feedback loop or the like.

Figure 36:
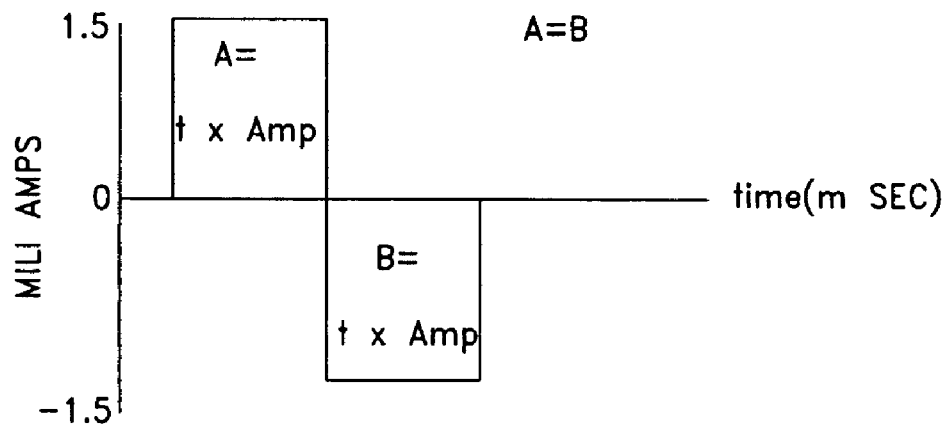
FIG. 36 is a graphical representation of an embodiment of an electrical signal waveform.
Figure 37:
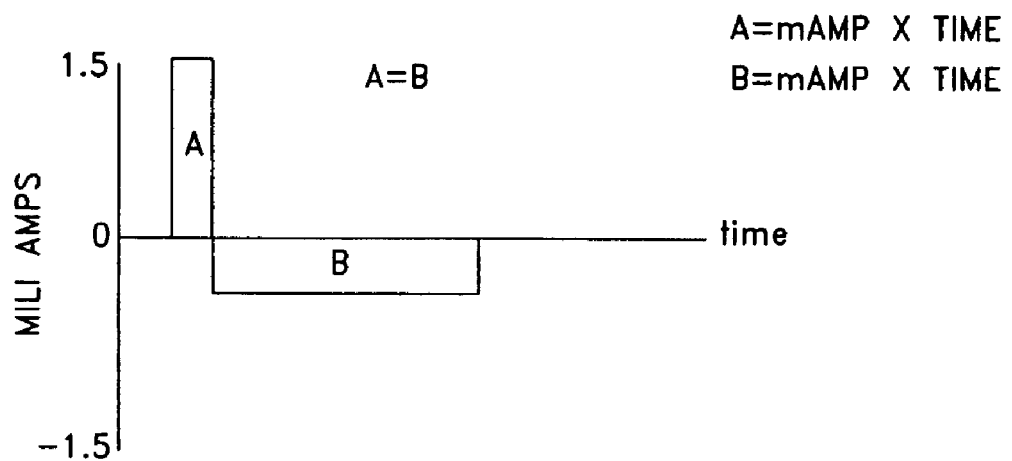
FIG. 37 is a graphical representation of an embodiment of an electrical signal waveform.

In one embodiment a helical electrode design with platinum iridium ribbon electrodes is used. The electrodes encircle all or a substantial portion of the nerve. A balanced charge biphasic pulse may be delivered to the electrodes, resulting in a bidirectional action potential to activate both efferent and afferent neurons. However, utilizing a waveform that is asymmetrical between the positive and negative phase deflections can create a unidirectional action potential, resulting in anodal block without incidental afferent fiber activation. Thus, whereas a typical biphasic waveform has equal positive and negative phase deflections as shown in FIG. 36, the anodal blocking waveform would have a short and tall positive deflection followed by a long shallow negative deflection as shown in FIG. 37. The product of amperage times time for each deflection would be equal, thereby achieving a charge balance. Charge balance is a consideration for avoiding nerve damage.

Figure 38:
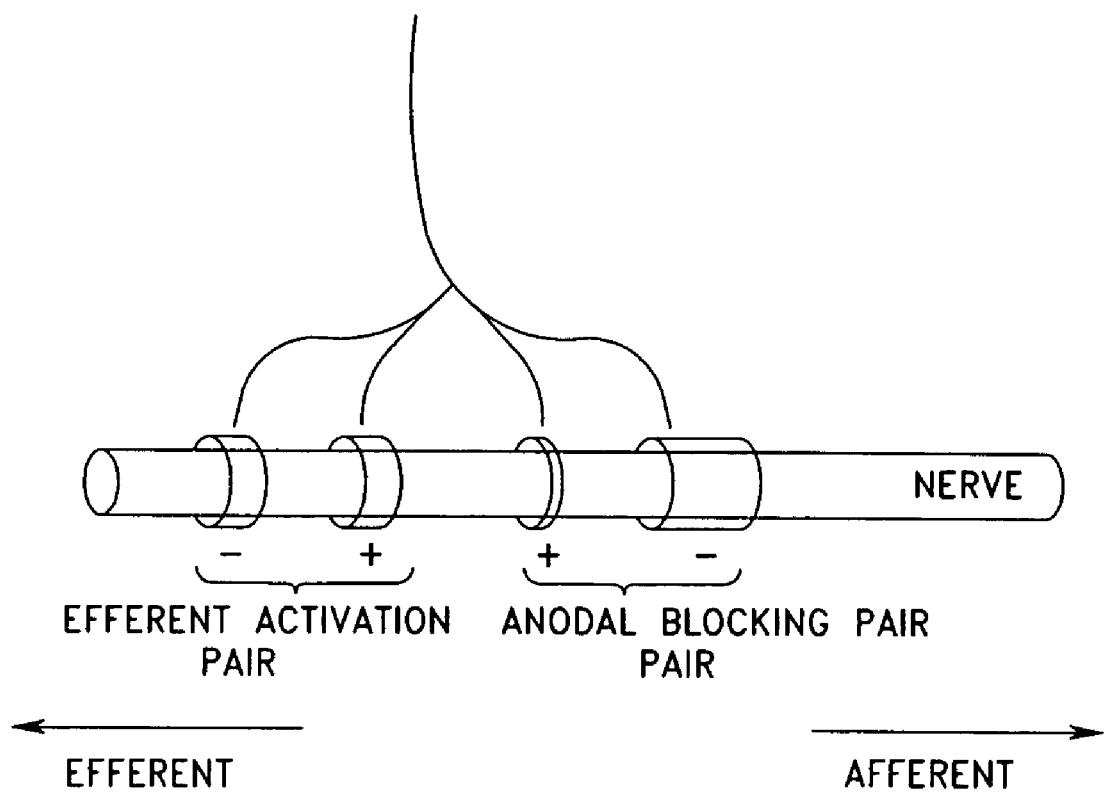
FIG. 38 is a schematic lateral view of an electrode assembly.

Alternatively, a quadripolar electrode assembly may be used. One pair of electrodes placed distally on a nerve may be used to produce efferent nerve activation. A second proximal pair may be used to block the afferent A fiber conduction. The blocking electrode pair may have asymmetric electrode surface areas, with the cathode surface area being greater than the anode as discussed by Petruska in U.S. Pat. No. 5,755,750 and shown in FIG. 38. Because of the large surface area at the cathode, the charge density may be insufficient to cause activation. The small surface area at the anode may cause hyperpolarization, particularly in the A fibers, and thereby block afferent conduction. Signals may be sent to four electrodes, timed such that when the efferent activation pair created a bi-directional action potential, the blocking pair would be active as the afferent potential traveled up the nerve. Alternatively, the blocking pair can be activated continuously during the treatment period.

A tripolar electrode may also be used to get activation of a select fiber size bilaterally or to get unilateral activation. To get bi-directional activation of B fibers and anodal blocking of A fibers, a tripolar electrode with the cathode flanked proximally and distally by anodes may be used. Unidirectional activation may be achieved by moving the cathode closer to the proximal electrode and delivering differential current ratios to the anodes.

Pulse generation for electrical nerve modulation may be accomplished using a pulse generator. Pulse generators can use microprocessors and other standard electrical components. An embodiment of a pulse generator may generate a pulse, or stimulation energy signal, at frequencies ranging from approximately 0.5 Hz to approximately 300 Hz, a pulse width from about 10 µsec to about 1,000 µsec, and a constant current of about 0.1 mA to about 20 mA. The pulse generator may be capable of producing a ramped, or sloped, rise in the current amplitude. Some embodiments of pulse generators may be configured to communicate with an external programmer and or monitor. Passwords, handshakes and parity checks may be employed for data integrity. The pulse generator can be battery operated or operated by an external radiofrequency device. Because embodiments of the pulse generator, associated components, and battery may be implanted in the body of a patient, they are, in some embodiments, encased in an epoxy-titanium shell.

Some embodiments of tissue modulation devices for treatment of a patient may include an electrical tissue modulation energy source. The tissue modulation energy source may have a logic and control unit coupled to a memory unit that stores machine readable information. The machine readable information may be read by the logic and control unit to produce a tissue modulation pattern that is configured to treat any of a variety of conditions, including at least one attendant or contributing condition of metabolic syndrome. An electrode is disposed in electrical communication with the electrical tissue stimulation energy source and configured to be coupled to a nerve of the patient.

Figure 39:
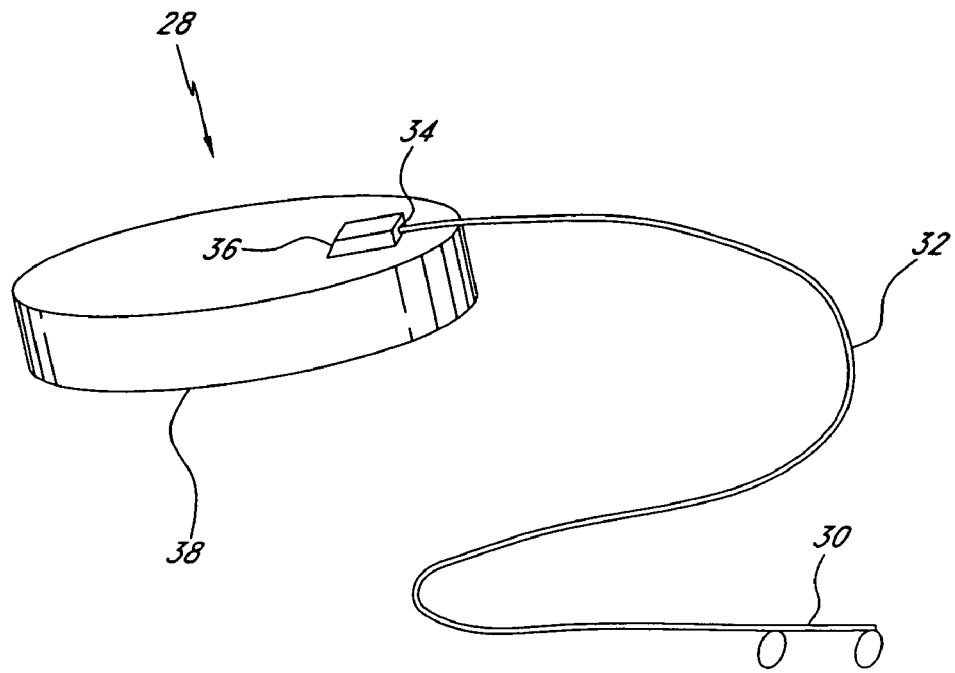
FIG. 39 is a perspective view of an embodiment of an electric tissue modulation device including an implantable pulse generator electrically coupled to a cuff electrode by an elongate electric lead.

Referring to FIG. 39, an electrical tissue modulation energy source in the form of an implantable pulse generator (IPG) 28 is coupled to a cuff electrode 30 by a conductive lead 32. Embodiments of the conductive lead 32 may include a central conductor or bundle of central conductors, braided or otherwise, surrounded by an insulation layer. The conductive lead 32 may generally be a flexible thin member capable of transmitting electrical energy of a variety of types and may be electrically insulated and shielded in order to prevent energy from escaping into surrounding tissue. The conductive lead 32 may be configured to transmit direct current, alternating current including radiofrequency current and the like. The length of embodiments of the conductive lead 32 may be from about 10 cm to about 100 cm. Pins at a proximal end 34 of the electrode lead 32 plug into a receptacle 36 in the IPG 28. The various circuitry components of the IPG 28 may be housed in an epoxy-titanium shell 38. The IPG shell 38 is generally disc shaped and may have an outer transverse dimension of about 3 cm to about 15 cm and a thickness of about 3 mm to about 15 mm.

Figure 40:
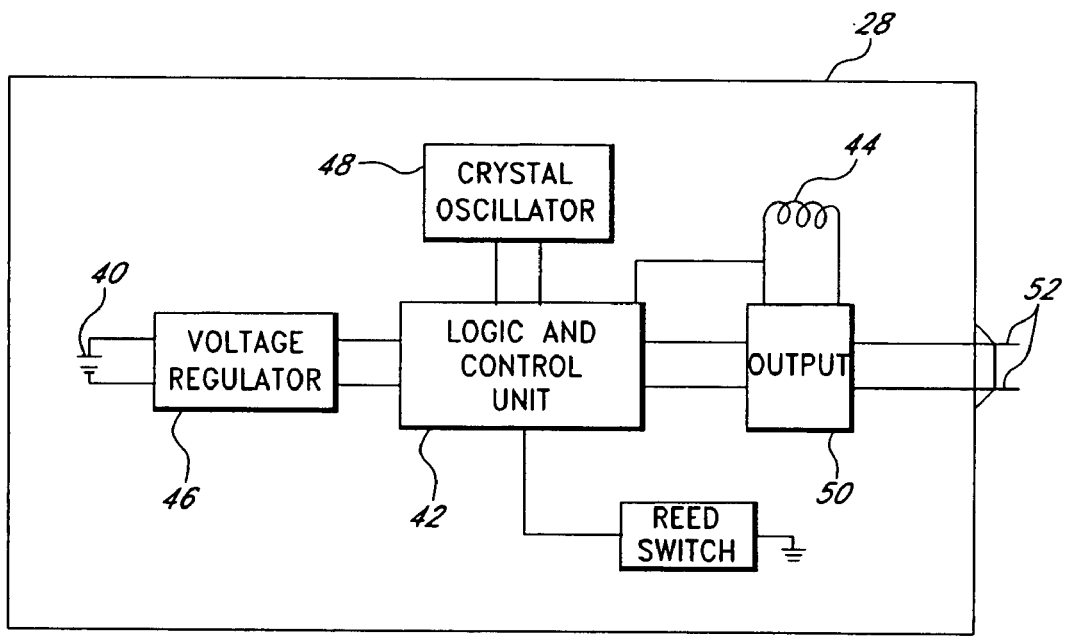
FIG. 40 shows a schematic view of an embodiment of an implantable pulse generator.

Referring to the schematic representation of an embodiment of an IPG 28 in FIG. 40, the IPG 28 contains a battery 40 that is coupled to and supplies power to a logic and control unit 42 that may include a central processing unit and memory unit (not shown). The battery 40 itself may be of a rechargeable variety that may be recharged either by direct electric coupling with a recharge voltage supply or by remote inductive coupling. If inductive coupling is to be used, a recharge signal may be generated external to a patient's body and coupled to a receiver which is in turn in electrical communication with the battery 40. A tissue stimulation pattern, which, for some embodiments, may be a tissue stimulation or treatment algorithm, may be programmed into the memory unit of the logic and control circuit 42. The memory unit may include software or hardware that is configured to store information necessary to carry out a tissue stimulation pattern or regimen in a repeatable and controllable manner. Such information stored in the memory unit may be uploaded or downloaded via non-invasive wireless communication via an antenna 44 which is coupled to the logic and control unit 42.

A voltage regulator 46 is disposed between the battery 40 and logic and control unit 42 and controls the battery output to the logic and control unit 42. A crystal oscillator 48 provides timing signals for output pulse signals and for the logic and control unit 42 generally. The antenna 44 is coupled to an output unit 50 and the logic and control unit 42 and is used for transmitting information to and receiving communications from an external programmer or wand (not shown). The external programmer or wand can also check on the status of the IPG 28. The output unit 50 is coupled to the electric lead 32 of the IPG 28 which may terminate at a receptacle 52 configured to couple electrically with the pins on the proximal end 34 of the conductive lead 32 of the cuff electrode 30. The output unit 50 may also include a radio transmitter to inductively couple with a wireless electrode embodiment (not shown) of the cuff electrode 30. For such an embodiment, conductive electric leads between the IPG 28 and the cuff electrode 30 would be unnecessary. One embodiment of the IPG 28 may include the Cyberonics Model 101 manufactured by the Cyberonics Company in Houston, Tex.

The logic and control unit 42 controls the tissue stimulation output energy and includes a memory unit that may store machine readable information which allows for programming of desired tissue stimulation patterns or algorithms including the chronological profile of electrical stimulation energy parameters over time including the signal voltage, frequency, pulse width, duty cycle and the like. Such desired tissue stimulation patterns or algorithms may include any of the stimulation patterns or algorithms discussed herein. The tissue stimulation patterns or algorithms may be configured to reduce obesity, improve lipid profiles or aspects of lipid profiles, increase energy expenditure, increase lean tissue or muscle mass or treat any other attendant or contributing condition of metabolic syndrome discussed herein.

Figure 41:
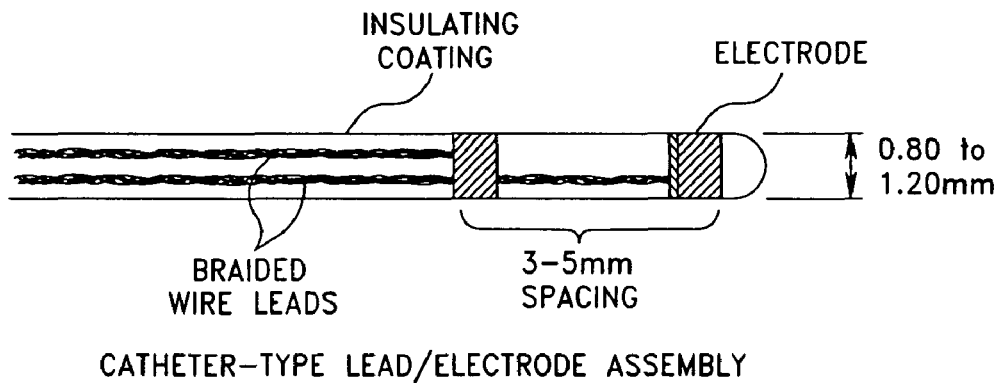
FIG. 41 is a diagrammatic view of an exemplary catheter-type lead and electrode assembly.

In certain embodiments, the electrodes may be platinum or platinum-iridium ribbons or rings as shown in FIG. 41. In certain embodiments, the electrodes may comprise other materials configured to conduct electromagnetic or mechanical energy. The electrodes are capable of electrically coupling with the surrounding tissue and nerve. The electrodes can encircle a catheter-like lead assembly. The distal electrode may form a rounded cap at the end to create a bullet nose shape. In some embodiments, this electrode serves as the cathode. A lead of this type may contain about 2 ring electrodes to about 4 ring electrodes spaced anywhere from about 2 mm to about 5 mm apart with each ring electrode being approximately 1 mm to approximately 10 mm in width. Catheter lead electrode assemblies may have an outer diameter of approximately 0.5 mm to approximately 1.5 mm to facilitate percutaneous placement using an introducer.

In certain embodiments, a helical or cuff electrode may be used, as are known to those of skill in the art. A helical or cuff electrode may prevent migration of the lead away from the nerve. Helical electrodes may be optimal in some settings because they may reduce the chance of nerve injury and ischemia. Embodiments of the IPG may be implanted subcutaneously, infra-abdominally, or intrathoracically, and/or in any location that is appropriate.

In certain embodiments, a wireless system may be employed by having an electrode that inductively couples to an external radiofrequency field. A wireless system may be used to avoid problems such as lead fracture and migration, found in wire-based systems. It would also simplify the implant procedure, by allowing simple injection of the wireless electrode in proximity to the splanchnic nerve, and avoiding the need for lead anchoring, tunneling, and subcutaneous pulse generator implantation.

Figure 42:
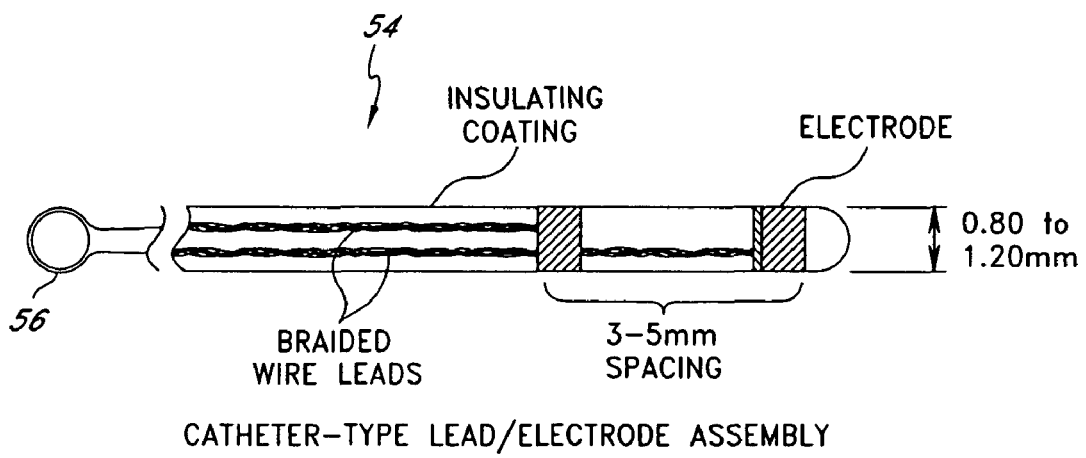
FIG. 42 shows a wireless electrode embodiment.

A wireless electrode embodiment 54, as shown in FIG. 42, may contain a coil/capacitor element 56 that may receive a radiofrequency signal. The radiofrequency signal may be generated by a device that would create an electromagnetic field sufficient to power the electrode. It may also provide for the transmission of information configured to set the desired stimulation parameters such as frequency, pulse width, current amplitude, signal on/off time and the like. Embodiments of the radiofrequency signal generator can be worn externally or implanted subcutaneously. Embodiments of the electrode may also have metallic elements for electrically coupling to the tissue or splanchnic nerve. The metallic elements can be made of platinum or platinum iridium. In certain embodiments, the wireless electrode may have a battery that would be charged by an radiofrequency field that would then provide stimulation during intervals without an radiofrequency field.

Bipolar stimulation of a nerve may be accomplished with multiple electrode assemblies with one electrode serving as the positive node and the other serving as a negative node. In this manner nerve activation can be directed primarily in one direction (unilateral), such as efferently, or away from the central nervous system. Alternatively, a nerve cuff electrode can be employed. Helical cuff electrodes as described in U.S. Pat. No. 5,251,634 to Weinberg may be used for some embodiments. Cuff assemblies may similarly have multiple electrodes and direct and cause unilateral nerve activation.

Unipolar stimulation may also be performed to modulate nerves or nerve tissue. As used herein, unipolar stimulation means using a single electrode on the lead, while the metallic shell of the IPG, or another external portion of the IPG, functions as a second electrode, remote from the first electrode. This type of unipolar stimulation may be more suitable for splanchnic nerve stimulation than the bipolar stimulation method, particularly if the electrode is to be placed percutaneously under fluoroscopic visualization. With fluoroscopically observed percutaneous placement, it may not be possible to place the electrodes adjacent the nerve, which may used for bipolar stimulation in some embodiments. With unipolar stimulation, a larger energy field may be created in order to couple electrically the electrode on the lead with the remote external portion of the IPG, and the generation of this larger energy field may result in activation of the nerve even in the absence of close proximity between the single lead electrode and the nerve. This allows successful nerve stimulation with the single electrode placed in "general proximity" to the nerve, meaning that there may be significantly greater separation between the electrode and the nerve than the "close proximity" used for bipolar stimulation. The magnitude of the allowable separation between the electrode and the nerve will necessarily depend upon the actual magnitude of the energy field that the operator generates with the lead electrode in order to couple with the remote electrode.

In multiple electrode lead assemblies, some of the electrodes may be used for sensing nerve activity. This sensed nerve activity may serve as a signal to commence stimulation therapy. For example, afferent action potentials in the splanchnic nerve, created due to the commencement of feeding, can be sensed and used to activate the IPG to begin stimulation of the efferent neurons of the splanchnic nerve. Appropriate circuitry and logic for receiving and filtering the sensed signal would be used in the IPG.

In addition, one or more sensors directed to food intake, or other parameters relating to obesity or other attendant or contributing conditions of metabolic syndrome may be used to provide feedback in a closed loop or the like in order to adjust stimulation signal parameters or treatment algorithms. Examples of such feedback or control loop embodiments have been discussed above with regard to achieving predetermined levels of plasma catecholamine, ghrelin and HDL, however, the same or similar methods may be used with regard to any attendant or contributing condition or component thereof of metabolic syndrome, if an underlying level of the attendant or contributing condition may be sensed by a sensor, such as a sensor disposed in communication with a patient's body, or other suitable method of measurement.

Figure 43:
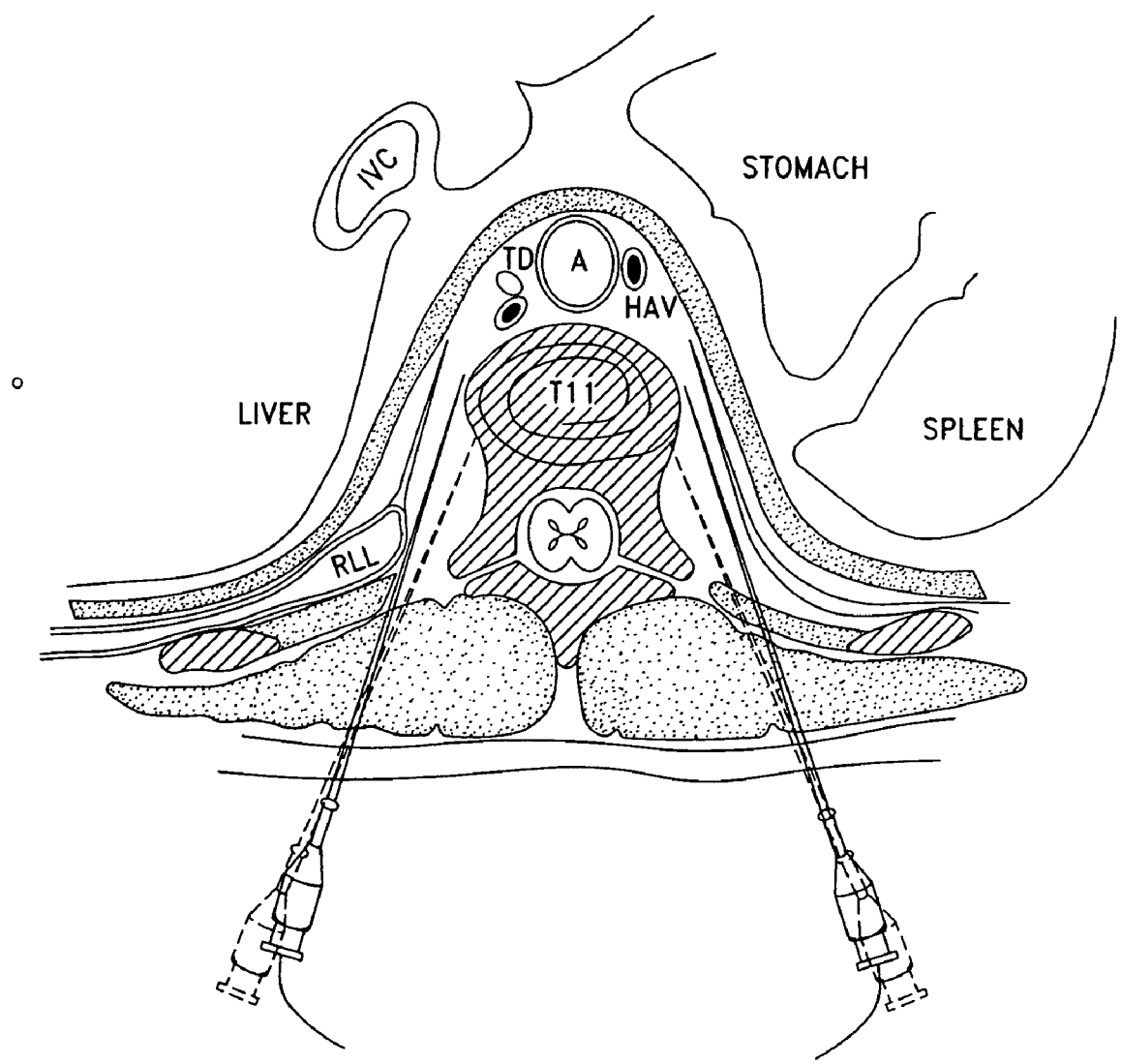
FIG. 43 is a cross sectional view of an exemplary method for instrument

Implantation of the lead/electrode assembly for activation of the greater splanchnic nerve (also referred to herein as "the splanchnic nerve") may be accomplished percutaneously using an introducer as shown in FIG. 43. The introducer can be a hollow needle-like device that would be placed posteriorly through the skin between the ribs para-midline at the T9-T12 level of the thoracic spinal column. A posterior placement with the patient prone may allow bilateral electrode placement at the splanchnic nerves, if desired. Placement of the needle can be guided using fluoroscopy, ultrasound, or CT scanning. Proximity to the splanchnic nerve by the introducer can be sensed by providing energy pulses to the introducer electrically to activate the nerve while monitoring for a rise in MAP or muscle twitching. All but the tip of the introducer can be electrically isolated so as to focus the energy delivered to the tip of the introducer. The lower the current amplitude used to cause a rise in the MAP or muscle twitch, the closer the introducer tip would be to the nerve.

In some embodiments, the introducer tip serves as the cathode for stimulation. In certain embodiments, a stimulation endoscope can be placed into the stomach of the patient for electrical stimulation of the stomach. The evoked potentials created in the stomach may be sensed in the splanchnic nerve by the introducer. To avoid damage to the spinal nerves, the introducer can sense evoked potentials created by electrically activating peripheral sensory nerves. Alternatively, evoked potentials can be created in the lower intercostal nerves or upper abdominal nerves and sensed in the splanchnic. Once the introducer was in proximity to the nerve, a catheter type lead electrode assembly would be inserted through the introducer and adjacent to the nerve. Alternatively, a wireless, radiofrequency battery charged, electrode may be advanced through the introducer to reside alongside the nerve. In either case, stimulating the nerve and monitoring for a rise in MAP or muscle twitch can be used to confirm electrode placement.

Once the electrode is in place the current amplitude may be increased at a pulse width of about 50 μsec to about 500 μsec and a frequency of about 1 Hz, until the threshold for muscle twitching is reached. The current amplitude may be set slightly above or slightly below this muscle twitch threshold. After identifying the desired current amplitude the pulse width may be increased by as much as 2.5 times and the frequency increased up to about 40 Hz for therapeutic stimulation. The lead, where used, and the IPG may be implanted subcutaneously in the patient's back or side. The lead may be appropriately secured to tissue of the patient to avoid dislodgement. The lesser and least splanchnic nerves may also be activated to some degree by lead/electrode placement according to the above procedure, due to their proximity to the splanchnic nerve.

Percutaneous placement of the lead electrode assembly may be enhanced using direct or video assisted visualization. An optical port can be incorporated into the introducer. A channel can allow the electrode lead assembly to be inserted and positioned, once the nerve was visualized. Alternatively, a percutaneous endoscope can be inserted into the chest cavity for viewing advancement of the introducer to the nerve. The parietal lung pleura are relatively clear, and the nerves and introducer can be seen running along the vertebral bodies. With the patient prone, the lungs are pulled forward by gravity creating a space for the endoscope and for viewing. This can avoid the need for single lung ventilation. If desired, one lung can be collapsed to provide space for viewing. This is a common and safe procedure performed using a bifurcated endotracheal tube. The endoscope can also be placed laterally, and positive CO2 pressure can be used to push down the diaphragm, thereby creating a space for viewing and avoiding lung collapse.

In certain embodiments, stimulation electrodes may be placed along the sympathetic chain ganglia from approximately vertebra T4 to T11. This implantation may be accomplished in a similar percutaneous manner as discussed above. This may create a more general activation of the sympathetic nervous system, though it would include activation of the neurons that comprise the splanchnic nerves.

In certain embodiments, the lead/electrode assembly may be placed intra-abdominally on the portion of the splanchnic nerve that resides retroperitoneally on the abdominal aorta just prior to synapsing in the celiac ganglia. Access to the nerve in this region can be accomplished laparoscopically, using typical laparoscopic techniques, or via open laparotomy. A cuff electrode may be used to encircle the nerve unilaterally or bilaterally. The lead can be anchored to the crus of the diaphragm. A cuff or patch electrode can also be attached to the celiac ganglia unilaterally or bilaterally. Similar activation of the splanchnic branches of the sympathetic nervous system would occur as implanting the lead electrode assembly in the thoracic region.

In certain embodiments, lead/electrode placement may be accomplished using a transvascular approach. Due to the proximity of the splanchnic nerves to the azygous veins shown in FIG. 43, and in particular the right splanchnic nerve and right azygous vein, modulation can be accomplished by positioning a lead/electrode assembly in this vessel. Access to the venous system and azygous vein can occur via the subclavian vein using standard techniques. The electrode/lead assembly can be mounted on a catheter. A guidewire can be used to position the catheter in the azygous vein. The lead/electrode assembly would include an expandable member, such as a stent. The electrodes would be attached to the stent, and using balloon dilation of the expandable member, can be pressed against the vessel wall so that energy delivery can be transferred to the nerve. The expandable member would allow fixation of the electrode lead assembly in the vessel. The IPG and remaining lead outside of the vasculature may be implanted subcutaneously in a manner similar to a heart pacemaker.

In some embodiments, the apparatus for nerve stimulation may be shielded or otherwise made compatible with magnetic resonance imaging (MRI) devices, such that the apparatus is less susceptible to current induction and its resultant heat effects and potential malfunction of electronics in the apparatus, and movement of the apparatus due to Lorentz forces. This type of magnetic shielding may be accomplished by, for example, using materials for the IPG or other generator embodiments and/or electrode that are nanomagnetic or utilize carbon composite coatings. Such techniques are described in U.S. Pat. Nos. 6,506,972 and 6,673,999, and U.S. Patent Application No. 2002/0183796, published Dec. 5, 2002; U.S. Patent Application No. 2003/0195570, published Oct. 16, 2003; and U.S. Patent Application No. 2002/0147470, published Oct. 10, 2002. The entireties of all of these references are hereby incorporated by reference.

As discussed above, in some embodiments, methods of treatment for obesity involve electrical stimulation of the splanchnic nerve (sympathetic system) and the vagus nerve (parasympathetic system). Weight loss induced by electrical activation of the splanchnic nerve can be amplified by providing dynamic stimulation. Dynamic stimulation refers to changing the values of stimulation intensity and/or stimulation frequency during treatment. The stimulation intensity and/or stimulation frequency may be changed independently, or they may be changed in concert. One parameter may be changed, leaving other parameters constant. In some cases multiple parameters may be changed approximately concurrently. The stimulation intensity and/or stimulation frequency may be changed at regular intervals, or they may be ramped up or down substantially continuously. The stimulation intensity and/or stimulation frequency may be changed to preset values, or they may be changed to randomly generated values. In this regard, it can be advantageous to provide a programmable IPG such that "fine-tuning" of the stimulation parameter can be varied during the course of a treatment regime in order to optimize the dynamic and frequency modulation of the neural stimulation thus achieving either a desired or a maximal rate of weight loss. In some cases it may be desirable to lose weight at a certain rate that is less than the maximum rate of loss possible for a particular patient. Such regime would be possible with embodiments as disclosed herein.

Weight loss induced by electrical activation of the splanchnic nerve can be optimized by applying a dynamic, or changing, stimulation intensity (e.g., increasing or decreasing either daily, or on some other periodicity). Applying a dynamic stimulation intensity produces a more pronounced weight loss than stimulation at a constant intensity.

Additionally, weight loss induced by electrical activation of the splanchnic nerve and the vagus nerve can be optimized by modulating the frequency of the electric stimulation. Afferent fibers in the splanchnic nerve send signals to the central nervous system with information regarding satiety. Thus, modulating the frequency of the stimulus applied to this nerve will result in a reduction in food intake, due to an evoked sense of satiety as a result of the stimulation. The frequency of the signal applied to the splanchnic nerve is directly correlated with intensity of the sensation of satiety. Stimulating the afferent neurons at a high frequency produces a more pronounced feeling of satiety, in turn resulting in a reduced food (i.e., reduced caloric) intake. Reduced feeding results in a caloric deficit, which leads inevitably to weight loss. The individual's weight will decrease until the reduced average caloric intake is roughly equal to the average caloric expenditure, and a new equilibrium is established.

Likewise, the vagus nerve relays signals related to stomach distension. This mechanical information is another source of information regarding fullness during feeding. The frequency of impulses carried from the stomach by the vagus is directly correlated with the degree of distension. In some embodiments, therefore, stimulating afferent vagal neurons at high frequency will mimic a distended stomach. By stimulating at this frequency an artificial sense of fullness results which leads to reduced feeding, and again weight loss. Without being limited to any particular hypothesis, the aforementioned conclusions are derived from studies of feeding in canines in which embodiments of the present disclosure were tested. The results of these studies are generally considered to be applicable to all mammals.

Figure 44:
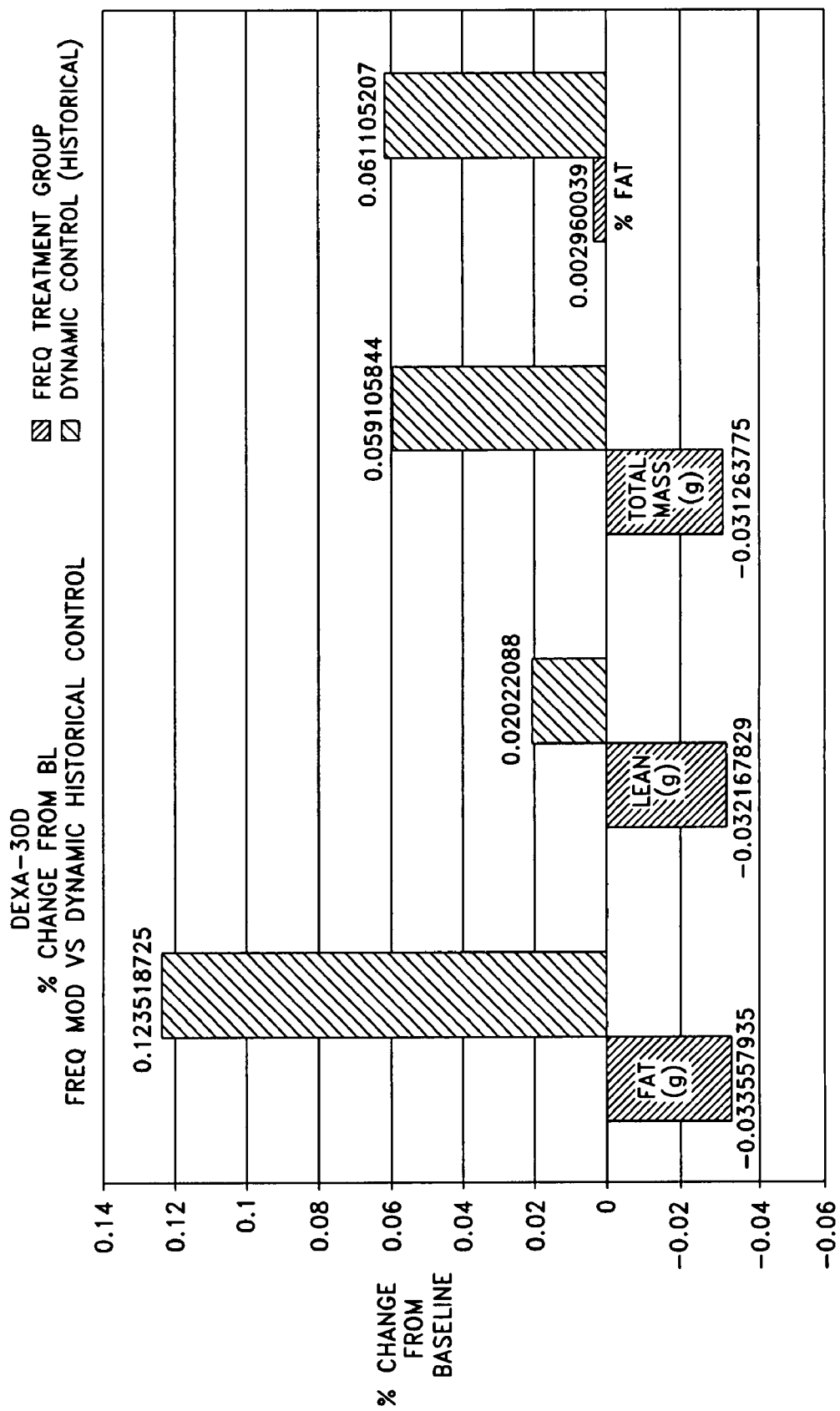
FIG. 44 shows the percent change in body weight for five canine subjects, in which the stimulation intensity is increased and decreased at regular intervals and in which the stimulation frequency is ramped up and then decreased.
Figure 45:
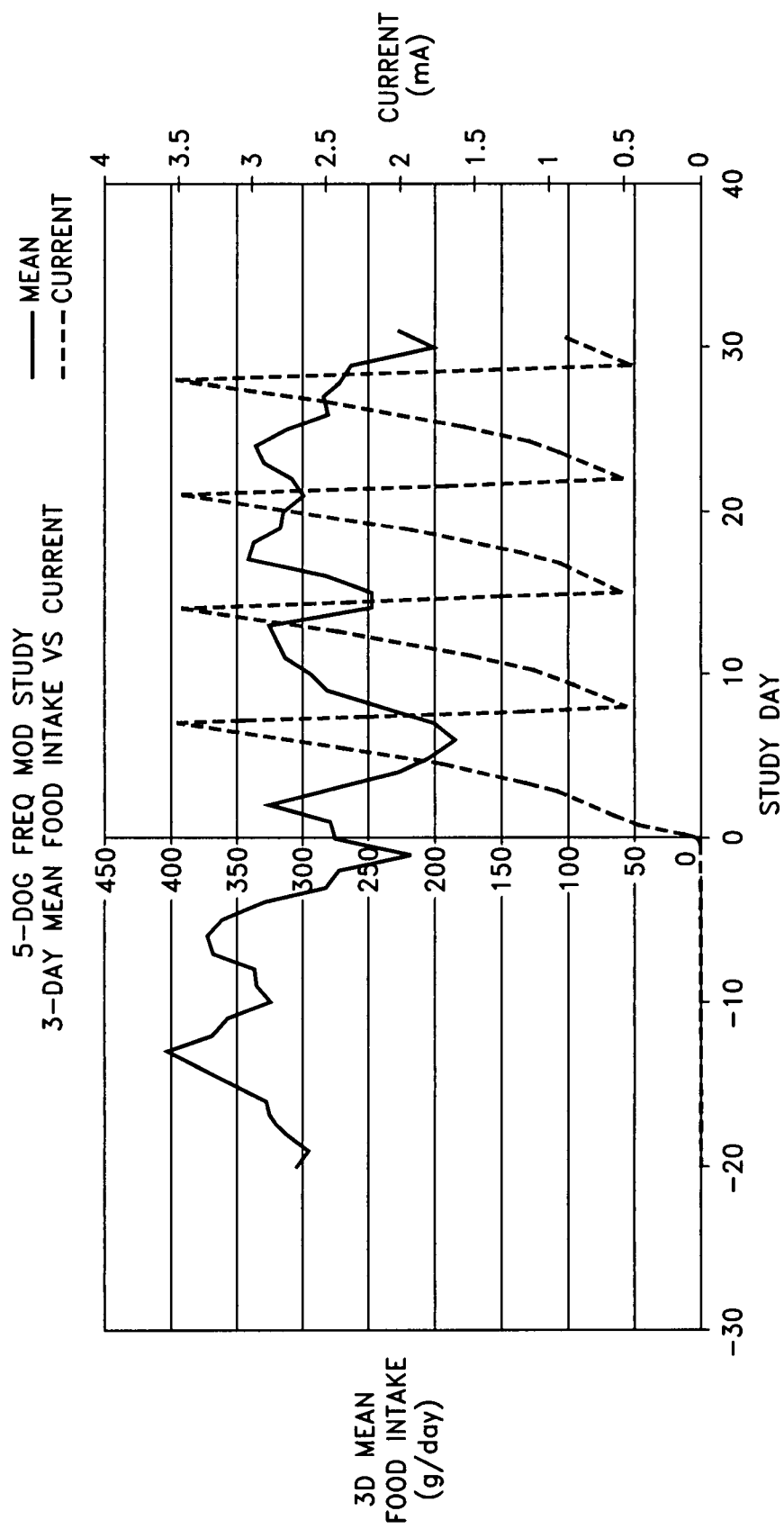
FIG. 45 shows the change in mean food intake for five canine subjects, in which the stimulation intensity is increased and decreased at regular intervals and in which the stimulation frequency is ramped up and then decreased.
Figure 46:
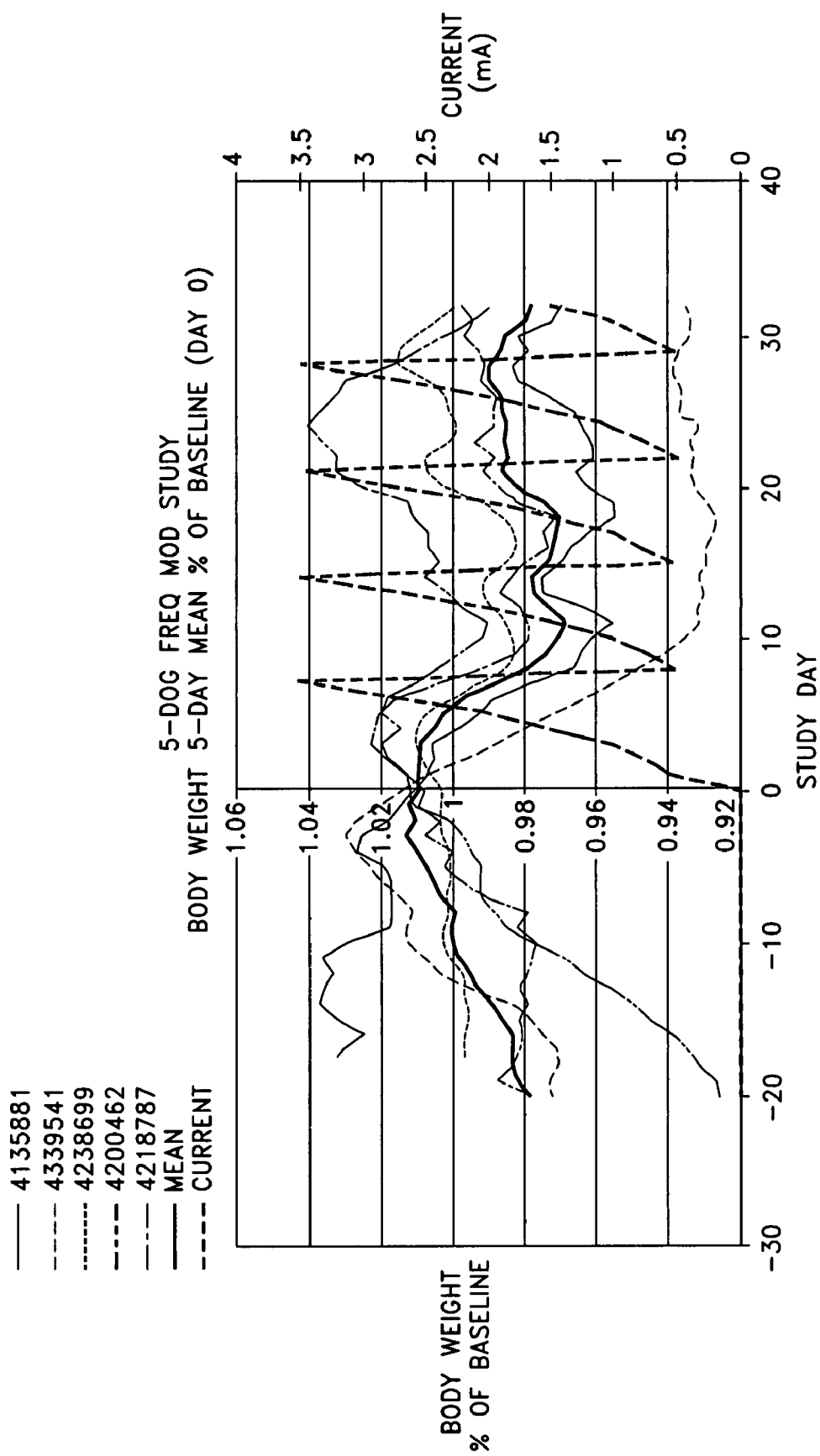
FIG. 46 shows a percent change in bodyweight as determined by a Dual Energy X-Ray Absorptiometry (DEXA) scan for a control set and for a set of test subjects subjected to a stimulus whereby the frequency was modulated.

Results from a study of five canine test subjects in which the nervous system was electrically stimulated over a period of about 30 days using an electrical signal configured according to embodiments of the present disclosure are shown in FIGS. 44-46. Each test subject was given an electrical stimulus having a stimulation intensity pattern, where the nerve was stimulated at a first stimulation intensity for at least a portion of a first interval, and then at a second stimulation intensity for at least a portion of a second interval, and where the stimulation intensity pattern is repeated. In some embodiments, the first stimulation intensity was about 3.5 mA and the second stimulation intensity was about 0.5 mA. One cycle of the stimulus, applying a stimulation intensity of 3.5 mA and then a stimulation intensity of 0.5 mA, was repeated daily for 30 days. At the same time, the electrical signal was configured to include a frequency pattern, such that the nerve was stimulated first at 10 Hz, then at 20 Hz, then at 30 Hz, and then the frequency was returned to 10 Hz. This pattern was repeated once a day for the 30-day duration of the experiment.

In the experiment shown in FIG. 44 an electric stimulus with a stimulation frequency pattern, modulated over the course of a 24-hour period, was applied. Dual Energy X-Ray Absorptiometry (DEXA) scanning of a set of test subjects subjected to a frequency modulated stimulus revealed a change in body composition as compared to unstimulated controls. The DEXA scan measures percent changes from baseline of fat, lean mass, total mass, and percent fat.

Over the course of the experiment, the group receiving frequency modulated treatment showed decreases in fat and lean mass, while these values for these two parameters increased in the dynamically stimulated control group. Moreover, the treatment group receiving a frequency modulated stimulus showed a decrease in total mass, in contrast to the dynamically stimulated control group, which experienced an increase in total mass. Finally, the frequency modulated treatment group showed a very slight increase in percent body fat while the dynamically stimulated control group displayed a significantly greater increase in percent body fat.

As shown in FIG. 45, food intake was decreased during the experimental period. In addition, a fluctuation in food intake between a maximum of 345 g per day and a minimum of 190 g per day was observed. The results also suggest that the effect of simulation on food intake results in a lower food intake soon after commencement of the frequency modulated stimulation pattern. The lowest food intake of the entire 30 days treatment occurred at about day six, coincident with the first increase in stimulation current. Each succeeding nadir in food intake during the experiment also appeared to be temporally linked to increased current when using this frequency modulated stimulation pattern. As shown in FIG. 46, the average relative body weight of the five subjects decreased during the first 10 days of the experiment, stabilizing thereafter at the lower weight.

Embodiments disclosed herein show that food intake, and accordingly weight loss, can be regulated by stimulation of the nervous system, and in particular, by stimulation of the splanchnic nerve. Additionally, in some embodiments, the stimulation frequency is modulated; the stimulation intensity may be increased at regular intervals and may then be reduced. In some embodiments, the stimulation intensity may be reduced to a level of about 0.5 mA. In other embodiments, the stimulation intensity may be reduced to a level of about zero. In some embodiments the stimulation intensity can be increased to about 2.5 mA, to about 3.5 mA, or to about 5 mA. A pattern of increasing the stimulation intensity and then decreasing the intensity can be repeated at defined intervals. This pattern can be repeated indefinitely.

In addition to a stimulation intensity pattern, the electrical signal applied to the nerve can be configured to comprise a stimulation frequency pattern. In some embodiments, stimulation occurs at a frequency of about 10 Hz during the morning; at about 20 Hz during the late morning or afternoon; and at about 30 Hz in the late afternoon and evening, with the stimulation frequency being returned to about 10 Hz overnight, wherein the cycle repeats again the next day. In some embodiments, the frequency pattern is repeated daily for at least 30 days or longer.

The stimulation frequency can be dynamically modulated by ramping the frequency from one frequency to another frequency, over a period of time. In some embodiments, ramping comprises an incremental change in frequency from one frequency to another. In some embodiments, the size of each increment is in a range from about 1 Hz to about 10 Hz, and the time between each successive incremental change in frequency is in a range from about 1 minute to about 5 minutes. The frequency can then be ramped back down to about 10 Hz, using similar, or different increments, wherein the cycle can be repeated.

Figure 47A:
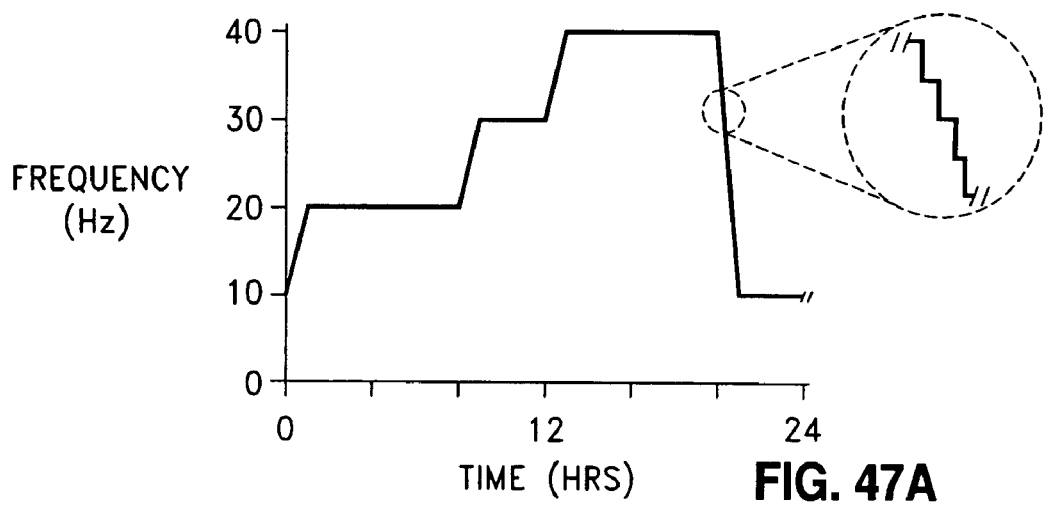
FIG. 47A-C are exemplary graphic representations of embodiments of a frequency modulated stimulation pattern.

In some embodiments, frequency changes can be discrete, while in some embodiments, frequency changes continuously according to the pattern configuration dictated by the device programming, or in response to input from sensors that measure physiological parameters. A number of frequency patterns are possible, of which FIGS. 47A-C provides some examples.

In some embodiments, after ramping to a frequency, the frequency is maintained for a period of time such that the frequency pattern takes on the appearance of a series of rises and plateaus. An example this type of pattern is illustrated in FIG. 47A. Here frequency changes from one frequency to the next over a time period, and then the frequency is relatively constant for an additional time period. The change from one frequency to the next can be continuous, or as shown in the inset of FIG. 47A, frequency changes can occur by incremental steps. In FIG. 47A, the inset shows a decremental stepwise frequency change, although those skilled in the art will readily appreciate that both increases and decreases in frequency can be done in a step-wise manner.

Figure 47B:
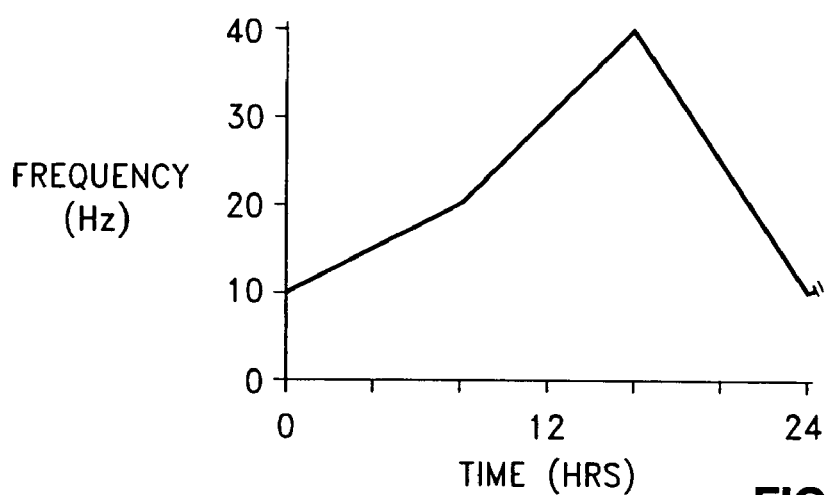
Figure 47C:
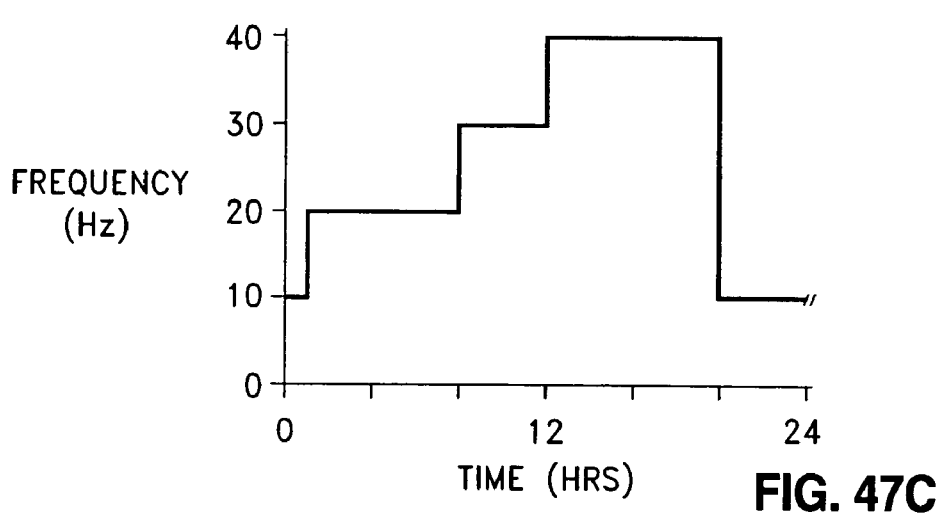

In some embodiments, as shown in FIG. 47B, frequency can be varied in a continuous manner from one frequency to the next. As with the embodiment illustrated in FIG. 47A, the change in frequency can be continuous or by way of incremental increase and decreases. In some embodiments, the change in frequency can be performed in a discrete, stepwise fashion, as shown in FIG. 47C.

It is also not required that each succeeding cycle be identical to those that precede it. For example, the time taken to change from one frequency to the next, the time spent at a particular frequency, and the actual stimulation frequencies can be varied from one iteration of the cycle to the next. In some embodiments, a cycle may be divided into equal time intervals where the time spent at each frequency is substantially the same. In some embodiments, the time period spent at one frequency may be different from the time period at one or more of the other frequencies. In some embodiments, the time taken to change from one frequency to the next in the cycle can be the same or different. The cycle can be repeated once per day, or the cycle can be repeated more or less often.

In some embodiments, the interval of changing the stimulation intensity is daily. In some embodiments, the interval of the stimulation intensity is changed daily, and the stimulation frequency is also changed daily. In certain embodiments, the frequency is increased throughout the daily interval by increasing from about 10 Hz in the morning, to about 20 Hz in the late morning or afternoon, to about 30 Hz in the evening or late afternoon, and then returned to about 10 Hz overnight. In some embodiments, a further increase to about 40 Hz is included prior to returning to about 10 Hz.

In certain embodiments, the pattern is repeated on successive days. In certain embodiments the interval for frequency modulation can be varied over a period other than daily, for example, the pattern can repeated more than one time during the course of a day, or the period may be repeated, without limitation at other intervals, including period greater than 24 hours. In addition, the repeated interval for frequency modulation need not be the same from one iteration to the next, but can also be varied.

In some embodiments, the pattern of frequency changes and stimulation intensity interval changes may be repeated indefinitely. The frequency change pattern may also be repeated during constant stimulation at a static stimulation intensity. Alternatively, the frequency pattern may occur several times daily (for instance, in the morning, afternoon, and evening). As a result, the overall simulation pattern will comprise a "layering" of several factors including duration, voltage, current, and frequency of the stimulus.

The frequency changes may occur in response to a physiological parameter. In some embodiments, the physiological parameter includes, without limitation, eating, blood glucose level, blood insulin level, blood cholesterol level, blood HDL level, blood LDL level, ghrelin levels, leptin levels, catecholamine levels, adipokine levels, and mean arterial blood pressure.

In some embodiments, directing an implantable device to deliver the configured electrical signal could be performed manually. For example, a patient could be instructed to administer a stimulation sequence by directing a command signal to the IPG, such as when feeling hungry or prior to a meal, in order to induce the satiety response prior to eating. This would result in the patient feeling full either before eating or at a point earlier in the meal. This would be effective to reduce food intake, in turn resulting in weight loss.

In cases where the IPG responds to a sensor, the IPG could be programmed to be self-homeostatic, using sensor measurements of physiological parameters as triggers to alter the ramp-cycling and/or frequency modulation parameters. Again this will enhance the rate of weight loss or aid in maintaining a target weight once that has been achieved.

While certain aspects and embodiments of the disclosure have been described, these have been presented by way of example only and are not intended to limit the scope of the disclosure. Indeed, the novel methods and systems described herein may be embodied in a variety of other forms without departing from the spirit thereof. The accompanying claims and their equivalents are intended to cover some forms or modifications as would fall within the scope and spirit of the disclosure.

What is claimed is:

1. An implantable medical device that outputs a configured electrical signal effective to modulate a nerve in a mammal;
    wherein the electrical signal comprises:
    a stimulation intensity pattern that varies at least one of a current amplitude and a pulse width in the signal; and
    a stimulation frequency pattern that varies frequency in the signal;
    wherein the combination of the stimulation intensity pattern and the stimulation frequency pattern in the electrical signal, as applied to a nerve in the mammal, is effective to result in at least one of a loss of fat mass and a gain in lean mass of the mammal.

2. The device of claim 1, wherein the stimulation intensity pattern and stimulation frequency pattern are varied over time, independently of each other.

3. The device of claim 1, wherein the stimulation intensity pattern comprises:
    stimulating at a first intensity during at least a portion of a first interval;
    stimulating at a second intensity during at least a portion of a second interval.

4. The device of claim 1, wherein the device is configured to deliver the stimulation intensity pattern at least once in a 24 hour period.

5. The device of claim 3, wherein the first intensity comprises a current of about 2.5 mA to about 5.0 mA.

6. The device of claim 3, wherein the second intensity comprises a current of about 0 mA to about 1.0 mA.

7. The device of claim 3, wherein the first intensity comprises a current of about 3.5 mA and the second intensity comprises a current of about 0.5 mA.

8. The device of claim 1, wherein the stimulation frequency pattern comprises at least one change in frequency.

9. The device of claim 8, wherein the at least one change in frequency occurs at a constant rate.

10. The device of claim 9, wherein the at least one change in frequency occurs by at least one increment.

11. The device of claim 10, where the at least one increment of about 1 Hz to about 20 Hz.

12. The device of claim 10, where the at least one increment of about 2 Hz to about 10 Hz.

13. The device of claim 1, wherein the stimulation frequency pattern comprises:
    a first stimulation frequency applied during a first portion of the stimulation frequency pattern;
    a second stimulation frequency applied during a second portion of the stimulation frequency pattern; and
    a third stimulation frequency applied during a third portion of the stimulation frequency pattern.

14. The device of claim 13, wherein the first stimulation frequency is about 10 Hz, the second stimulation frequency is about 20 Hz, and the third stimulation frequency is about 30 Hz.

15. The device of claim 14, wherein the stimulation frequency pattern further comprises a fourth stimulation frequency applied during a fourth portion of the stimulation frequency pattern.

16. The device of claim 15, wherein the fourth stimulation frequency is about 40 Hz.

17. The device of claim 1, further configured to deliver the stimulation frequency pattern at least once in a 24 hour period.

18. The device of claim 1, further configured to modulate a sympathetic nerve.

19. The device of claim 1, further configured to modulate a splanchnic nerve, wherein the splanchnic nerve comprises at least one of a greater splanchnic nerve, a lesser splanchnic nerve, and a least splanchnic nerve.

20. The device of claim 1, wherein the nerve comprises a parasympathetic nerve.

21. The device of claim 1, wherein the nerve comprises a vagus nerve.

22. The device of claim 1, wherein the device is configured to deliver the electrical signal in response to a physiological parameter.

23. The device of claim 22, wherein the physiological parameter is at least one of eating, a blood glucose level, a blood insulin level, a blood cholesterol level, a blood HDL level, a blood LDL level, a ghrelin level, a leptin level, a catecholamine level, an adipokine level, and an arterial pressure.

24. The device of claim 22, further comprising a sensor configured to measure the physiological parameter, and wherein the device is configured to deliver the electrical signal in response to a signal received from the sensor.

25. The device of claim 24, wherein the sensor is positionable within the body of the mammal.

26. The device of claim 1, configured to be implanted in a human patient.

27. The device of claim 26, configured to deliver the electrical signal in response to a command from the patient.

28. A method of electrically modulating a nerve in a mammal, comprising:
    configuring an electrical signal to comprise:
    a stimulation intensity pattern that varies at least one of a current amplitude and a pulse width in the signal; and
    a stimulation frequency pattern that varies frequency in the signal; and
    applying the electrical signal to a nerve in the mammal;
    wherein the combination of the stimulation intensity pattern and the stimulation frequency pattern in the electrical signal, as applied to a nerve in the mammal, is effective to result in at least one of a loss of fat mass and a gain in lean mass of the mammal.

29. The method of claim 28, wherein the stimulation intensity pattern and stimulation frequency pattern are varied over time, independently of each other.

30. The method of claim 28, wherein the stimulation intensity pattern comprises:
    stimulating at a first intensity during at least a portion of a first interval;

stimulating at a second intensity during at least a portion of a second interval.

31. The method of claim 30, wherein the stimulation intensity pattern is repeated at least once in a 24 hour period.

32. The method of claim 30, wherein the first intensity is about 2.5 mA to about 5 mA.

33. The method of claim 30, wherein the second intensity is about 0 mA to about 1.0 mA.

34. The method of claim 30, wherein the first intensity comprises a current of about 3.5 mA and the second intensity comprises a current of about 0.5 mA.

35. The method of claim 30, wherein the stimulation frequency pattern comprises at least one change in frequency.

36. The method of claim 35, wherein the at least one change in frequency occurs at a constant rate.

37. The method of claim 36, wherein the at least one change in frequency occurs by at least one increment.

38. The method of claim 37, wherein the at least one increment is about 1 Hz to about 20 Hz.

39. The method of claim 37, wherein the at least one increment is about 2 Hz to about 10 Hz.

40. The method of claim 28, wherein the stimulation frequency pattern comprises:
   applying the electrical signal at a first stimulation frequency during a first portion of the stimulation frequency pattern;
   applying the electrical signal at a second stimulation frequency during a second portion of the stimulation frequency pattern;
   applying the electrical signal at a third stimulation frequency during a third portion of the stimulation frequency pattern.

41. The method of claim 35, wherein the first stimulation frequency is about 10 Hz, the second stimulation frequency is about 20 Hz, and the third stimulation frequency is about 30 Hz.

42. The method of claim 35, further comprising applying the electrical signal at a fourth stimulation frequency during a fourth portion of the stimulation frequency pattern.

43. The method of claim 42, wherein the fourth frequency is about 40 Hz.

44. The method of claim 35, wherein the stimulation frequency pattern is repeated at least once in a 24 hour period.

45. The method of claim 28, wherein the nerve comprises a sympathetic nerve.

46. The method of claim 28, wherein the nerve comprises a splanchnic nerve, wherein the splanchnic nerve comprises at least one of a greater splanchnic nerve, a lesser splanchnic nerve, and a least splanchnic nerve.

47. The method of claim 28, wherein the nerve comprises a parasympathetic nerve.

48. The method of claim 28, wherein the nerve comprises a vagus nerve.

49. The method of claim 28, wherein the electrical signal is applied in response to a physiological parameter.

50. The method of claim 49, wherein the physiological parameter comprises at least one of eating, a blood glucose level, a blood insulin level, a blood cholesterol level, a blood HDL level, a blood LDL level, a ghrelin level, a leptin level, a catecholamine level, an adipokine level, and an arterial pressure.

51. The method of claim 49, wherein the electrical signal is applied in response to a signal from a sensor configured to measure the physiological parameter.

52. The method of claim 51, wherein the sensor is positionable within the body of the mammal.

53. The method of claim 28, wherein the mammal is a human patient.

54. The method of claim 53, wherein the electrical signal is applied in response to a command from the patient.

* * * * *